United States Patent
Salem et al.

(10) Patent No.: US 10,314,854 B2
(45) Date of Patent: Jun. 11, 2019

(54) METHODS FOR TREATING TUMORS IN SITU INCLUDING INTRATUMOR INJECTION OF CYTOTOXIC PARTICLES AND IMMUNE CHECKPOINT BLOCKADE THERAPY

(71) Applicant: University of Iowa Research Foundation, Iowa City, IA (US)

(72) Inventors: Aliasger K. Salem, Coralville, IA (US); Amani Makkouk, Iowa City, IA (US); Vijaya B. Joshi, Minneapolis, MN (US); George Weiner, Iowa City, IA (US)

(73) Assignee: University of Iowa Foundation, Iowa City, IA (US)

( * ) Notice: Subject to any disclaimer, the term of this patent is extended or adjusted under 35 U.S.C. 154(b) by 0 days.

(21) Appl. No.: 15/572,347

(22) PCT Filed: May 16, 2016

(86) PCT No.: PCT/US2016/032712
§ 371 (c)(1),
(2) Date: Nov. 7, 2017

(87) PCT Pub. No.: WO2016/187122
PCT Pub. Date: Nov. 24, 2016

(65) Prior Publication Data
US 2018/0147224 A1    May 31, 2018

Related U.S. Application Data

(60) Provisional application No. 62/162,397, filed on May 15, 2015.

(51) Int. Cl.
A61K 31/704 (2006.01)
A61K 9/00 (2006.01)
(Continued)

(52) U.S. Cl.
CPC .......... *A61K 31/704* (2013.01); *A61K 9/0019* (2013.01); *A61K 9/1647* (2013.01);
(Continued)

(58) Field of Classification Search
CPC .. A61K 31/704; A61K 9/1647; A61K 9/0019; A61K 47/34; A61P 35/00; C07K 16/2878; C07K 16/2818
See application file for complete search history.

(56) References Cited

FOREIGN PATENT DOCUMENTS

| WO | 2002054425 A2 | * | 4/2012 | ....... A61K 47/48876 |
| WO | 2012054425 | * | 4/2012 | |
| WO | 20151069770 | * | 5/2015 | |

OTHER PUBLICATIONS

Conde-Estevez D, Mateu-de AJ. Treatment of anthracycline extravasations using dexrazoxane. Clin Transl Oncol Off Publ Fed Span Oncol Soc Natl Cancer Inst Mexico. 2014;16(1):11-7.
(Continued)

*Primary Examiner* — Carlos A Azpuru
(74) *Attorney, Agent, or Firm* — Quarles & Brady LLP

(57) ABSTRACT

Disclosed are compositions, kits, and methods for treating cancer in a subject in need thereof. The compositions, kits, and methods may be used to treat a tumor in a subject in situ. The compositions, kits, and methods comprise or utilize cytotoxic particles, immune checkpoint inhibitors, and/or T-cell stimulatory agents.

20 Claims, 25 Drawing Sheets

(51) Int. Cl.
    A61K 47/34      (2017.01)
    C07K 16/28      (2006.01)
    A61P 35/00      (2006.01)
    A61K 9/16       (2006.01)
    A61K 31/7088    (2006.01)
    A61K 39/39      (2006.01)
    A61K 39/00      (2006.01)

(52) U.S. Cl.
    CPC .......... A61K 31/7088 (2013.01); A61K 47/34
        (2013.01); A61P 35/00 (2018.01); C07K
        16/2818 (2013.01); C07K 16/2878 (2013.01);
        A61K 39/0011 (2013.01); A61K 39/39
        (2013.01); A61K 2039/505 (2013.01); A61K
        2039/507 (2013.01); A61K 2039/54 (2013.01);
        A61K 2039/55561 (2013.01); A61K 2039/585
        (2013.01); C07K 2317/75 (2013.01)

(56)                References Cited

OTHER PUBLICATIONS

Craft N, Bruhn KW, Nguyen BD, Prins R, Liau LM, Collisson EA, et al. Bioluminescent imaging of melanoma in live mice. J Investig Dermatol. 2005;125(1):159-65. doi: 10.1111/j.0022-202X.2005.23759.x.
Crittenden MR, Thanarajasingam U, Vile RG, Gough MJ. Intratumoral immunotherapy: using the tumour against itself. Immunology. 2005;114(1):11-22. doi: 10.1111/j.1365-2567.2004.02001.x.
Danhier F, Ansorena E, Silva JM, Coco R, Le Breton A, Preat V. PLGA-based nanoparticles: an overview of biomedical applications. J Control Release Off J Control Release Soc. 2012;161(2):505-22. doi: 10.1016/j.jconrel.2012.01.043.
Galluzzi L, Senovilla L, Vacchelli E, Eggermont A, Fridman WH, Galon J, et al. Trial watch: dendritic cell-based interventions for cancer therapy. Oncoimmunology. 2012;1(7):1111-34. doi: 10.4161/onci.21494.
Galluzzi L, Vacchelli E, Eggermont A, Fridman WH, Galon J, Sautes-Fridman C, et al. Trial watch: adoptive cell transfer immunotherapy. Oncoimmunology. 2012;1(3):306-15. doi: 10.4161/onci.19549.
Galluzzi L, Vacchelli E, Eggermont A, Fridman WH, Galon J, Sautes-Fridman C, et al. Trial watch: experimental toll-like receptor agonists for cancer therapy. Oncoimmunology. 2012;1(5):699-716. doi: 10.4161/onci.20696.
Geary SM, Krishnamachari Y, Lemke C, Salem AK, Weiner GJ. Biodegradable particulate formulations. Google Patents; 2012.
Hortobagyi GN. Anthracyclines in the treatment of cancer. An overview. Drugs. 1997;54(Suppl 4):1-7. doi: 10.2165/00003495-199700544-00003.
Houot R, Levy R. T-cell modulation combined with intratumoral CpG cures lymphoma in a mouse model without the need for chemotherapy. Blood. 2009;113(15):3546-52. doi: 10.1182/blood-2008-07-170274.
Krieg AM. From A to Z on CpG. Trends Immunol. 2002;23(2):64-5. doi: 10.1016/S1471-4906(01)02150-0.
Mellman I, Coukos G, Dranoff G. Cancer immunotherapy comes of age. Nature. 2011;480(7378):480-9. doi: 10.1038/nature10673.
Mizuno Y, Naoi T, Nishikawa M, Rattanakiat S, Hamaguchi N, Hashida M, et al. Simultaneous delivery of doxorubicin and immunostimulatory CpG motif to tumors using a plasmid DNA/doxorubicin complex in mice. J Control Release Off J Control Release Soc. 2010;141(2):252-9. doi: 10.1016/j.jconrel.2009.09.014.
Sharp FA, Ruane D, Claass B, Creagh E, Harris J, Malyala P, et al. Uptake of particulate vaccine adjuvants by dendritic cells activates the NALP3 inflammasome. Proc Natl Acad Sci U S A. 2009;106(3):870-5. doi: 10.1073/pnas.0804897106.
Topalian SL, Weiner GJ, Pardoll DM. Cancer immunotherapy comes of age. J. Clin.Oncol Off J Am Soc Clin Oncol. 2011;29(36)4828-36. doi: 10.1200/JCO.2011.38.0899.
Vacchelli E, Galluzzi L, Fridman WH, Galon J, Sautes-Fridman C, Tartour E, et al. Trial watch: chemotherapy with immunogenic cell death inducers. Oncoimmunology. 2012;1(2):179-88. doi: 10.4161/onci.1.2.19026.
Vacchelli E, Martins I, Eggermont A, Fridman WH, Galon J, Sautes-Fridman C, et al. Trial watch: peptide vaccines in aancer therapy. Oncoimmunology. 2012;1(9):1557-76. doi: 10.4161/onci.22428.
Wolchok JD, Yang AS, Weber JS. Immune regulatory antibodies: are they the next advance? Cancer J. 2010;16 (4):311-7. doi: 10.1097/PPO.0b013e3181eb3381.
Yoshida M, Babensee JE. Poly(lactic-co-glycolic acid) enhances maturation of human monocyte-derived dendritic cells. J Biomed Mater Res A. 2004;71(1):45-54. doi: 10.1002/jbm.a.30131.
Zang H, Liu L, Yu D, Kandimalla ER, Sun HB, Agrawal S, et al. An in situ autologous tumor vaccination with combined radiation therapy and TLR9 agonist therapy. PLoS One. 2012;7(5):e38111. doi: 10.1371/journal.pone.0038111.
ACR Cancer Progress Report Writing Committee, Sawyers CL, Abate-Shen C, et al. AACR cancer progress report 2013. Clin Cancer Res. 2013;19(20 Suppl):S4-98.
Aguilar LK, Guzik BW, Aguilar-Cordova E. Cytotoxic immunotherapy strategies for cancer: Mechanisms and clinical development. J Cell Biochem. 2011;112(8):1969-1977.
Bielcaid Z, Phallen JA, Zeng J, et al. Focal radiation therapy combined with 4-1BB activation and CTLA-4 blockade yields long-term survival and a protective antigen-specific memory response in a murine glioma model. PLoS One. 2014;9(7):e101764.
Benichou A, Garti N. Double emulsions for controlled-release applications—progress and trends. In: CRC Press; 2001:409-442. http://dx.doi.org.proxy.lib.uiowa.edu/10.1201/9781420029581.ch17. doi:10.1201/9781420029581.ch17.
Casares N, Pequignot MO, Tesniere A, et al. Caspase-dependent immunogenicity of doxorubicin-induced tumor cell death. J Exp Med. 2005;202(12):1691-1701.
Chakravarthi SS, De S, Miller DW, Robinson DH. Comparison of anti-tumor efficacy of paclitaxel delivered in nano- and microparticles. Int J Pharm. 2010;383(1-2):37-44.
Farazuddin M, Dua B, Zia Q, Khan AA, Joshi B, Owais M. Chemotherapeutic potential of curcumin-bearing microcells against hepatocellular carcinoma in model animals. Int J Nanomedicine. 2014;9:1139-1152.
Ghiringhelli F, Apetoh L, Tesniere A, et al. Activation of the NLRP3 inflammasome in dendritic cells induces IL-1beta-dependent adaptive immunity against tumors. Nat Med. 2009;15(10):1170-1178.
Grosso JF, Jure-Kunkel MN. CTLA-4 blockade in tumor models: An overview of preclinical and translational research. Cancer Immun. 2013;13:5.
Hempel G, Flege S, Wurthwein G, Boos J. Peak plasma concentrations of doxorubicin in children with acute lymphoblastic leukemia or non-hodgkin lymphoma. Cancer Chemother Pharmacol. 2002;49(2):133-141.
Hollander N. Immunotherapy for B-cell lymphoma: Current status and prospective advances. Front Immunol. 2012;3:3.
International Preliminary Report on Patentability for PCT/US2016/032712 dated Nov. 30, 2017.
Jahrsdorfer B, Blackwell SE, Wooldridge JE, et al. B-chronic lymphocytic leukemia cells and other B cells can produce granzyme B and gain cytotoxic potential after interleukin-21-based activation. Blood. 2006;108(8):2712-2719.
Locher C, Conforti R, Aymeric L, et al. Desirable cell death during anticancer chemotherapy. Ann N Y Acad Sci. 2010;1209:99-108.
Obeid M, Tesniere A, Ghiringhelli F, et al. Calreticulin exposure dictates the immunogenicity of cancer cell death. Nat Med. 2007;13(1):54-61.
Oyewumi MO, Kumar A, Cui Z. Nano-microparticles as immune adjuvants: Correlating particle sizes and the resultant immune responses. Expert Rev Vaccines. 2010;9(9):1095-1107.
Pardoll DM. The blockade of immune checkpoints in cancer immunotherapy. Nat Rev Cancer. 2012;12(4):252-264.

(56) References Cited

OTHER PUBLICATIONS

Sheng Sow H, Mattarollo SR. Combining low-dose or metronomic chemotherapy with anticancer vaccines: A therapeutic opportunity for lymphomas. Oncoimmunology. 2013;2(12):e27058.

Shurin GV, Tourkova IL, Shurin MR. Low-dose chemotherapeutic agents regulate small rho GTPase activity in dendritic cells. J Immunother. 2008;31(5):491-499.

Silva JM, Videira M, Gaspar R, Preat V, Florindo HF. Immune system targeting by biodegradable nanoparticles for cancer vaccines. J Control Release. 2013;168(2):179-199.

Timar J, Ladanyi A, Forster-Horvath C, et al. Neoadjuvant immunotherapy of oral squamous cell carcinoma modulates intratumoral CD4/CD8 ratio and tumor microenvironment: A multicenter phase II clinical trial. J Clin Oncol. 2005;23(15):3421-3432.

Tosato G, Cohen JI. Generation of epstein-barr virus (EBV)-immortalized B cell lines. Curr Protoc Immunol. 2007; chapter 7:Unit 7.22.

Visani G, Isidori A. Doxorubicin variants for hematological malignancies. Nanomedicine (Lond). 2011;6(2):303-306.

Waeckerle-Men Y, Groettrup M. PLGA microspheres for improved antigen delivery to dendritic cells as cellular amines. Adv Drug Deliv Rev. 2005;57(3):475-482.

Written Opinion and International Search Report for PCT/US2016/032712 dated Sep. 8, 2016.

Yoo HS, Lee KH, Oh JE, Park TG. In vitro and in vivo anti-tumor activities of nanoparticles based on doxorubicin-PLGA conjugates. J Control Release. 2000;68(3):419-431.

Makkouk, et al., "Biodegradable Microparticles Loaded with Doxorubicin and CpG ODN for In Situ Immunization Against Cancer", AAPS, 2015, 17(1): 184-193.

Makkouk, et al., "Three Steps to Breaking Immune tolerance to Lymphoma: A Microparticle Approach", AACR, 2015, 3(4): 389-398.

* cited by examiner

METHODS FOR TREATING TUMORS IN SITU INCLUDING INTRATUMOR INJECTION OF CYTOTOXIC PARTICLES AND IMMUNE CHECKPOINT BLOCKADE THERAPY

CROSS-REFERENCE TO RELATED PATENT APPLICATIONS

The present application is a U.S. National Phase application of International Application No. PCT/CA2016/050439, filed on Apr. 15, 2016, which claims the benefit of priority under 35 U.S.C. § 119(e) to U.S. Provisional Patent Application No. 62/162,397, filed on May 15, 2015, the contents of which are incorporated herein by reference in their entireties.

STATEMENT REGARDING FEDERALLY SPONSORED RESEARCH OR DEVELOPMENT

This invention was made with government support under grant number CA097274 awarded by the National Institutes of Health. The government has certain rights in the invention.

BACKGROUND

The field of the invention relates to compositions, kits, and methods for treating cancer in a subject. In particular, the compositions, kits, and methods relate to treating cancer in a subject having a solid tumor via inducing an immune response against the tumor.

In situ immunization is based on the concept that it is possible to break immune tolerance by inducing tumor cell death in situ in a manner that provides antigen-presenting cells such as dendritic cells (DCs) with a wide selection of tumor antigens that can then be presented to the immune system and result in a therapeutic anticancer immune response. Here, we describe an approach for in situ immunization. The described approach typically includes a step of inducing immunogenic tumor cell death via intratumoral injection with a chemotherapeutic drug formulated in biodegradable particles. The described approach further may include enhancing antigen presentation and T cell activation by administering a T-cell stimulatory agent, and/or sustaining T cell responses by administering an immune checkpoint inhibitor. The described approach provides new therapeutic methods for treating cancers characterized by solid tumors.

SUMMARY

Disclosed are compositions, kits, and methods for treating cancer in a subject in need thereof. In particular, the compositions, kits, and methods may be used to treat solid tumors in a subject in need thereof. The compositions, kits, and methods comprise or utilize one or more more of cytotoxic particles, immune checkpoint inhibitors, and/or T-cell stimulatory agents.

In the disclosed methods, a subject having a solid tumor may be treated by injecting the tumor with cytotoxic particles, which optionally may be formulated as a suspension. The cytotoxic particles typically comprise a biodegradable polymer and a cytotoxic agent and optionally may include a T-cell stimulatory agent. The cytotoxic particles are relatively small and typically have an average effective diameter of 0.5-10 microns.

In the disclosed methods, treating the subject further may include administering to the subject an immune checkpoint inhibitor. The immune checkpoint inhibitor may be administered parenterally, for example via intravenous or intraperitoneal delivery. The immune checkpoint inhibitor may be administered before, concurrently with, or after a tumor of the subject is injected with the cytotoxic particles.

In the disclosed methods, treating the subject further may include administering to the subject a T-cell stimulatory agent. The T-cell stimulatory agent may be administered before, concurrently with, or after the tumor of a subject is injected with the cytotoxic particles or before, concurrently with, or after the subject is administered an immune checkpoint inhibitor. The cytotoxic particles, in addition to comprising a biodegradable polymer and a cytotoxic agent, further may comprise the T-cell stimulatory agent.

In the disclosed methods, after the patient is administered the cytotoxic particles, the immune checkpoint inhibitor, and/or the T-cell stimulatory agent, the subject may develop an immune response against the tumor such as a T-cell response. As such, the disclosed methods may be practiced in order to break immune tolerance in the subject.

Also disclosed herein are compositions and kits for treating cancer in a subject in need thereof. The compositions and kits may be used for performing the disclosed methods for treating cancer in a subject in need thereof. The disclosed compositions and kits may include cytotoxic particles as disclosed herein or components for preparing the cytotoxic particles as disclosed herein. As such, also disclosed herein are methods for preparing the cytotoxic particles as disclosed herein. The disclosed compositions and kits for treating cancer in a subject in need thereof also may include immune checkpoint inhibitors as disclosed herein and/or T-cell stimulatory agents as disclosed herein.

DETAILED DESCRIPTION

Figure 1:
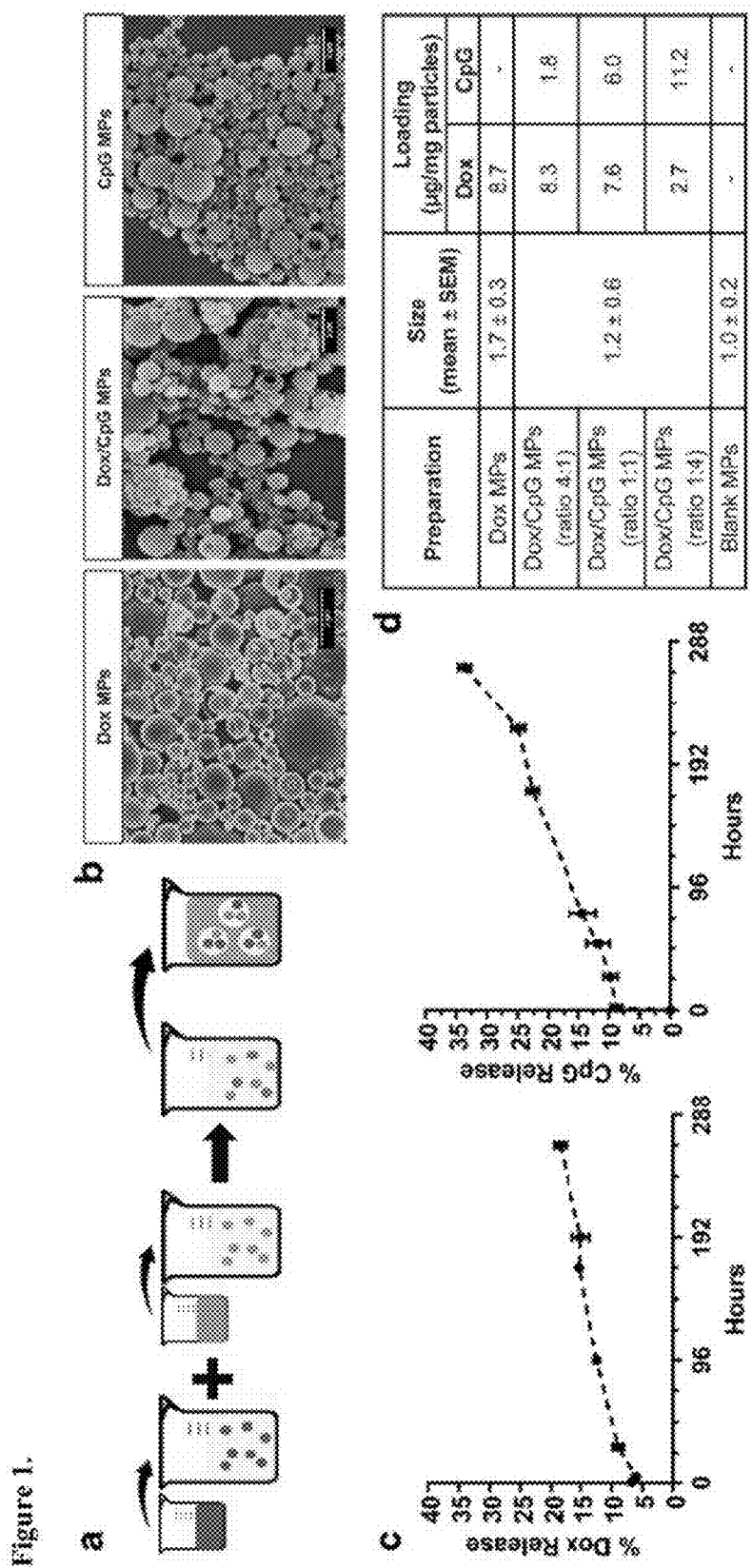
FIG. 1. Fabrication and characterization of PLGA particles. a. Modified double emulsion solvent evaporation procedure used for the preparation of Dox/CpG MPs. Dox and CpG solutions were emulsified separately in PLGA dissolved in dichloromethane forming w/o emulsions. The two emulsions were combined and w/o/w emulsion was prepared to obtain PLGA particles co-loaded with Dox and CpG. b. SEM microphotographs of Dox, Dox/CpG, and CpG PLGA MPs. The scale bar on the lower right represents 2 μm length. c. Percentage Dox and CpG release in PBS (pH 7.4) at 37° C. from Dox/CpG MPs (mean±SEM). Groups were compared using the paired t test (n=3). d Table representing an average size (diameter) and an average loading (μg/mg particles) of Dox and CpG in different MPs FIG. 2. Dox/CpG MPs are efficient at killing tumor cells. A20 a and EL4 b cells were incubated with soluble Dox or Dox/CpG MPs (4:1 loading) in 96-well plates for 24, 48, and 72 h at a final Dox concentration of 4.5 μg/mL. Media or blank MPs at equivalent weights were used as negative controls. Viability was assessed by the MTS assay. Results are mean±SEM (n=4). Comparisons are summarized in the tables. **$p<0.0001$; $p<0.01$; * $p<0.05$; n.s. not significant FIG. 3. Dox/CpG MPs are less toxic to BMDCs. A20, EL4, and BMDCs were incubated for 24 h with Dox/CpG MPs (1:1 loading) at final Dox concentrations ranging 0.28125-4.5 μg/mL. Media or blank MPs (average equivalent weight for highest and lowest concentrations) were used as control. Viability was assessed by the MTS assay. Results are mean±SEM (n=4). ***$p<0.001$; n.s. not significant FIG. 4. Low doses of Dox/CpG MPs are more efficient at reducing A20 tumor burdens. Nine million A20 tumor cells were injected subcutaneously in the right and left flanks of BALB/c mice. After 10 days, mice received PBS as control or Dox/CpG MPs (2 or 10 μg Dox; 4:1 loading) in the left tumor and six intraperitoneal doses of anti-CTLA-4 (50 μg) given every 3-4 days. Mice were monitored for tumor growth of both injected and distant tumors and survival. Tumor areas are mean±SEM FIG. 5. Dox/CpG MPs combined with Ab generate systemic immune responses that eradicate distant tumors. Seven million A20 tumor cells were injected subcutaneously in the right and left flanks of BALB/c mice. Treatment began when tumors reached 5-7 mm in largest diameter, which typically occurred at days 9-10 after tumor inoculation. Mice received PBS as control, Dox MPs (2 μg Dox), CpG MPs (1.5 μg CpG), or Dox/CpG MPs (2 μg Dox and 1.5 μg CpG; 1:1 loading) in the left tumor and three intraperitoneal doses of anti-CTLA-4 (50 μg) and anti-OX40 (200 μg) given every 3-4 days. Mice were monitored for tumor growth of both injected and distant tumors and survival. Tumor areas are mean±SEM. Results shown are pooled from two experiments (15-20 mice/group)

Disclosed are compositions, kits, and methods for treating cancer in a subject in need thereof, in particular in a subject having a cancer characterized by solid tumors. The compositions, kits, and methods may be further described as follows.

Unless otherwise specified or indicated by context, the terms "a", "an", and "the" mean "one or more." In addition, singular nouns such as "cytotoxic agent," "immune checkpoint inhibitor," and "T-cell stimulatory agent" should be interpreted to mean "one or more cytotoxic agent," "one or more cytotoxic agent," and "one or more T-cell stimulatory agent," respectively, unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The terms "subject," "patient," or "host" may be used interchangeably herein and may refer to human or non-human animals. Non-human animals may include, but are not limited to non-human primates, dogs, cats, horses, or other non-human animals.

The terms "subject," "patient," or "individual" may be used to refer to a human or non-human animal having or at risk for acquiring a cell proliferative disease or disorder. Subjects who are treated with the compositions disclosed herein may be at risk for cancer or may have already acquired cancer including cancers characterized by solid tumors. Cancers characterized by solid tumors may include, but are not limited to adenocarcinoma, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

The compositions, kits, and methods disclosed herein may comprise or utilize cytotoxic particles. The cytotoxic particles typically are relatively small and may have an effective average diameter of 0.01-500 μm, preferably 0.1-20 μm, and more preferably 0.5-10 μm. The cytotoxic particles may be referred to herein as "microparticles" and/or "nanoparticles."

The cytotoxic particles disclosed herein typically include a cytotoxic agent. Suitable cytotoxic agents include drugs using in chemotherapy for treating cancer. In some embodiments, the cytotoxic agent is selected from a group consisting of Abiraterone Acetate, Abitrexate (Methotrexate), Adriamycin (Doxorubicin Hydrochloride), Adrucil (Fluorouracil), Afatinib Dimaleate, Afinitor (Everolimus), Aldesleukin, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, aredia (Pamidronate Disodium), Arimidex (Anastrozole), Aromasin (Exemestane), Arranon (Nelarabine), Arsenic Trioxide, Asparaginase Erwinia chrysanthemi, Axitinib, Azacitidine, Becenum (Carmustine), Beleodaq (Belinostat), Belinostat, Bendamustine Hydrochloride, Bexarotene, Bicalutamide, BiCNU (Carmustine), Bleomycin, Bortezomib, Bosulif (Bosutinib), Bosutinib, Busulfan, Busulfex (Busulfan), Cabazitaxel, Cabozantinib-S-Malate, Camptosar (Irinotecan Hydrochloride), Capecitabine, Carboplatin, CARBOPLATIN-TAXOL, Carfilzomib, Carmubris (Carmustine), Carmustine, Casodex (Bicalutamide), CeeNU (Lomustine), Ceritinib, Cerubidine (Daunorubicin Hydrochloride), Chlorambucil, CHLORAMBUCIL-PREDNIS ONE, Cisplatin, Clafen (Cyclophosphamide), Clofarabine, Clofarex (Clofarabine), Clolar (Clofarabine), Cometriq (Cabozantinib-S-Malate), Cosmegen (Dactinomycin), Crizotinib, Cyclophosphamide, Cyfos (Ifosfamide), Cytarabine, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Dexrazoxane Hydrochloride, Docetaxel, Doxorubicin Hydrochloride, DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Everolimus, Evista (Raloxifene Hydrochloride), Exemestane, Fareston (Toremifene), Farydak (Panobinostat), Faslodex (Fulvestrant), Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRINOX, FOLFOX, Folotyn (Pralatrexate), Fulvestrant, Gefitinib, Gemcitabine Hydrochloride, GEMCITABINE-CISPLATIN, GEMCITABINE-OXALIPLATIN, Gemzar (Gemcitabine Hydrochloride), Gilotrif (Afatinib Dimaleate), Gleevec (Imatinib Mesylate), Gliadel (Carmustine Implant), Glucarpidase, Goserelin Acetate, Halaven (Eribulin Mesylate), Hycamtin (Topotecan Hydrochloride), Ibrance (Palbociclib), Ibrutinib, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Inlyta (Axitinib), Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), Lomustine, Lupron (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), Mozobil (Plerixafor), Mustargen (Mechlorethamine Hydrochloride), Mutamycin (Mitomycin C), Myleran (Busulfan), Mylosar (Azacitidine), Navelbine (Vinorelbine Tartrate), Nelarabine, Neosar (Cyclophosphamide), Nexavar (Sorafenib Tosylate), Nilotinib, Nolvadex (Tamoxifen Citrate), Nplate (Romiplostim), Olaparib, Omacetaxine Mepesuccinate, Ontak (Denileukin Diftitox), Oxaliplatin, Paclitaxel, Palbociclib, Palonosetron Hydrochloride, Pamidronate Disodium, Panobinostat, Paraplat (Carboplatin), Paraplatin (Carboplatin), Pazopanib Hydrochloride, Pemetrexed Disodium, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Promacta (Eltrombopag Olamine), Purinethol (Mercaptopurine), Purixan (Mercaptopurine), Radium 223 Dichloride, Raloxifene Hydrochloride, Regorafenib, Revlimid (Lenalidomide), Rheumatrex (Methotrexate), Romidepsin, Romiplostim, Rubidomycin (Daunorubicin Hydrochloride), Ruxolitinib Phosphate, Sorafenib Tosylate, Sprycel (Dasatinib), Stivarga (Regorafenib), Sunitinib Malate, Sutent (Sunitinib Malate), Synovir (Thalidomide), Synribo (Omacetaxine Mepesuccinate), Tafinlar (Dabrafenib), Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Totect (Dexrazoxane Hydrochloride), Trametinib, Treanda (Bendamustine Hydrochloride), Trisenox (Arsenic Trioxide), Tykerb (Lapatinib Ditosylate), Vandetanib, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vinorelbine Tartrate, Vismodegib, Vorinostat, Votrient (Pazopanib Hydrochloride), Wellcovorin (Leucovorin Calcium), Xalkori (Crizotinib), Xeloda (Capecitabine), Xofigo (Radium 223 Dichloride), Xtandi (Enzalutamide), Zaltrap (Ziv-Aflibercept), Zelboraf (Vemurafenib), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and combinations thereof.

The cytotoxic particles may comprise a suitable concentration of the cytotoxic agent for treating a tumor in situ. In some embodiments, the cytotoxic particles may comprise the cytotoxic agent at concentration value of at least about 0.01, 0.02, 0.05, 0.1, 0.2, 0.5, 1.0, 2.0, 5.0, 10.0, 20.0, or 50.0 µg/mg; or the cytotoxic particles may comprise the cytotoxic agent at a concentration value of no more than about 50.0, 20.0, 10.0, 5.0, 2.0, 1.0, 0.5, 0.2, 0.1, 0.05, 0.02 µg/mg cytotoxic agent; or the cytotoxic particles may comprise the cytotoxic agent within a concentration range bounded by any two of the preceding concentration values.

The cytotoxic particles disclosed herein comprise a biodegradable polymer as would be understood in the art. The term "biodegradable" describes a material that is capable of being degraded in a physiological environment into smaller basic components such as organic polymers. Preferably, the smaller basic components are innocuous. For example, a biodegradable polymer may be degraded into basic components that include, but are not limited to, water, carbon dioxide, sugars, organic acids (e.g., tricarboxylic or amino acids), and alcohols (e.g., glycerol or polyethylene glycol). Biodegradable polymers that may be utilized to prepare the particles contemplated herein may include materials disclosed in U.S. Pat. Nos. 7,470,283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018948; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated herein by reference in their entireties. Typically, the cytotoxic particles disclosed herein are degraded in vivo at a degradation rate such that the cytotoxic particles lose greater than about 50%, 60%, 70%, 80%, 90%, 95%, or 99% of their initial mass after about 4, 5, 6, 7, or 8 weeks post-administration to a tumor via one or more of: degradation of the biodegradable polymers of the cytotoxic particles to monomers: degradation of the biodegradable polymers of the cytotoxic particles to water, carbon dioxide, sugars, organic acids (e.g., tricarboxylic or amino acids), and alcohols (e.g., glycerol or polyethylene glycol); and degradation of the cytotoxic particles to release the cytotoxic agent of the particles or any other active agent of the particles such as T-cell stimulatory agent present in the cytotoxic particles.

Suitable polymers for preparing the cytotoxic particles may include, but are not limited to, polymers such as polylactides (PLA), including polylactic acid, for example, polyglycolides (PGA), including polyglycolic acid, and co-polymers of PLA and PGA (i.e., PLGA). Other suitable polymers may include, but are not limited to, polycaprolactone (PCL), poly(dioxanone) (PDO), collagen, renatured collagen, gelatin, renatured gelatin, crosslinked gelatin, and their co-polymers. The selected polymer(s) may be of any suitable molecular weight. The polymer of the cytotoxic particles may be designed to degrade as a result of hydrolysis of polymer chains into biologically acceptable and progressively smaller components (e.g., such as polylactides, polyglycolides, and their copolymers, which may break down eventually into lactic and glycolic acid, enter the Kreb's cycle, be broken down into carbon dioxide and water, and excreted).

The disclosed cytotoxic particles may be prepared by methods known in the art. In some embodiments, the cytotoxic particles may be formed from a solution or suspension of a biodegradable polymer in the presence of one or more cytotoxic agents and optionally a T-cell stimulatory agent. As such, the cytotoxic particles comprise a biodegradable polymer, a cytotoxic agent, and optionally may comprise one or more additional agents such as a T-cell stimulatory agent.

The disclosed compositions, kits, and methods may include or utilize an immune checkpoint inhibitor. In the disclosed methods, a subject having cancer may be treated by injected a tumor of the subject with the aforementioned cytotoxic particles. The methods further may include administering to the subject an immune checkpoint inhibitor, wherein the immune checkpoint inhibitor is administered before, concurrently with, or after the tumor of the subject is injected with the cytotoxic particles. Suitable immune checkpoint inhibitors are known in the art. In some embodiments, the immune checkpoint inhibitor is selected from the group consisting of, but not limited to, an anti CTLA-4 antibody (e.g., Ipilimumab or Tremelimumab), an anti PD-1 antibody (MDX-1106, BMS-936558, MK3475, CT-011, AMP-224), an anti PD-L1 antibody (e.g., MDX-1105), an anti IDO-1 antibody, and anti IDO-2 antibody, an anti KIR antibody, an anti CD70 antibody, an anti LAG-3 antibody (e.g., IMP321), an anti B7-H3 antibody (e.g., MGA271), and anti B7-H4 antibody, an anti TIM3 antibody, and combinations thereof.

The disclosed compositions, kits, and methods may include or utilize a T-cell stimulatory agent. In the disclosed methods, a subject having cancer may be treated by injected a tumor of the subject with the aforementioned cytotoxic particles and optionally the immune checkpoint inhibitor. The methods further may include administering to the subject a T-cell stimulatory agent, wherein the T-cell stimulatory agent is administered before, concurrently with, or after the tumor of the subject is injected with the cytotoxic particles and/or before, concurrently with, or after the subject is administered the immune checkpoint inhibitor.

Suitable T-cell stimulatory agents for the disclosed compositions, kits, and methods may include, but are not limited to T-cell stimulatory agents that target TNFR costimulatory molecules (e.g., an anti OX40 agonist antibody, an anti CD40 agonist antibody, or an anti CD137 agonist antibody) and T-cell stimulatory agents that are TLR agonists (e.g., CpG dinucleotide (CpG-ODN), polyribosinic:polyribocytidic acid (Poly I:C), polyadenosine-polyruridylilc acid (poly AU), polyinosinic-polycytidylic acid stabilized with poly-L-lysine and carboxymethylcellulose (Poly-ICLC), bacterial lipopolysaccharides (e.g., monophosphoryl lipid A (MPL)), MUC1 mucin (e.g., Sialyl-Tn (STn)), and imidazoquinolines (e.g., imiquimod and resiquimod)).

In some embodiments, the cytotoxic particles, in addition to comprising a biodegradable polymer and a cytotoxic agent, further may comprise the T-cell stimultatory agent, for example, in methods in which the cytotoxic particles are used to administer a cytotoxic agent a T-cell stimulatory agent simultaneously in situ to a tumor. The cytotoxic particles may comprise a suitable concentration of the T-cell stimulatory agent for stimulating a T-cell response after the cytotoxic particles are administered in situ to a tumor. In some embodiments, the cytotoxic particles may comprise the T-cell stimulatory agent at concentration value of at least about 0.01, 0.02, 0.05, 0.1, 0.2, 0.5, 1.0, 2.0, 5.0, 10.0, 20.0, or 50.0 µg/mg; or the cytotoxic particles may comprise the T-cell stimulatory agent at a concentration value of no more than about 50.0, 20.0, 10.0, 5.0, 2.0, 1.0, 0.5, 0.2, 0.1, 0.05, 0.02 µg/mg cytotoxic agent; or the cytotoxic particles may comprise the T-cell stimulatory agent within a concentration range bounded by any two of the preceding concentration values. The cytotoxic agent and the T-cell stimulatory agent may be present in the cytotoxic particles at a suitable concentration ratio (e.g., mass:mass ratio), such as 50:1, 20:1, 10:1, 5:1, 4:1, 3:1, 2:1, 1:1, 1:2, 1:3, 1:4, 1:5, 1:10, 1:20, or 50:1, or at a suitable concentration ratio range bounded by any two of the preceding values (e.g., at a concentration ratio range of 20:1-1:1).

As contemplated herein, the disclosed cytotoxic particles, immune checkpoint inhibitors, and T-cell stimulatory agents may be formulated in one or more pharmaceutical compositions. For example, a single pharmaceutical composition may comprise each of the disclosed cytotoxic particles, immune checkpoint inhibitors, and T-cell stimulatory agents and/or the disclosed cytotoxic particles, immune checkpoint inhibitors, and T-cell stimulatory agents may be present in two or more pharmaceutical compositions. Kits comprising the disclosed cytotoxic particles, immune checkpoint inhibitors, and T-cell stimulatory agents, as present in one or more pharmaceutical compositions also are contemplated. Furthermore, in some embodiments, the disclosed cytotoxic particles may comprise not only a biodegradable polymer and a cytotoxic agent but also the T-cell stimulatory agent, particularly when the T-cell stimulatory agent is a non-proteinaceous T-cell stimulatory agent.

The compositions disclosed herein may include pharmaceutical compositions that are administered to a subject having cancer in order to induce a therapeutic immune response against a solid tumor in the subject and potentially break immunology tolerance to the tumor in the subject. Inducing a therapeutic immune response may include inducing a response to one or more epitopes of an antigen associated with the tumor, including a T-cell response against one or more epitopes of an antigen associated with the tumor.

The presently disclosed methods may be utilized for inducing a therapeutic immune response against cancer by administering the pharmaceutical compositions disclosed herein to a subject in need thereof. The methods may include administering a first pharmaceutical composition (e.g., a first composition comprising cytotoxic particles, the cytotoxic particles comprising a cytotoxic agent and the cytotoxic particles optionally comprising a T-cell stimulatory agent) to a tumor mass of a subject in need thereof and optionally may include administering a second pharmaceutical composition (e.g., a second composition comprising an immune checkpoint inhibitor and/or a T-cell stimulatory agent) to the subject in order to augment or boost an immunogenic response induced by the first pharmaceutical composition. The administered second pharmaceutical composition may be administered prior to, concurrently with, or after administering the first pharmaceutical composition. In some embodiments, the first composition is administered and then the second composition is administered after waiting at least about 4, 5, or 6 weeks. The first composition (and the second composition) may be administered one or more times.

The presently disclosed compositions, kits, and methods also may be utilized to treat cancers or hyperproliferative disorders that are susceptible to cell-mediated immune responses in the host. Hyperproliferative disorders may include cancers, which may include, but are not limited to adenocarcinoma, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

The presently disclosed compositions may be administered to potentiate or enhance an immune response. As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth"). Preferably, a 5-fold, or more preferably a 10-fold or greater, enhancement in T-cell responses may be obtained by administering the pharmaceutical composition disclosed herein.

The presently disclosed compositions, kits, and methods may be utilized to induce an immune response, including, but not limited to a cellular immune response such as a T-cell response, which may be characterized by cytokine production such as interferons (e.g., IFN-γ), tumor necrosis factor (e.g., TNF-β), and interleukins (e.g., IL-2). A T-cell response also may be characterized by an increased killing efficiency of dendritic cells to killing cancer cells and the proliferation of cytotoxic $CD8^+$ cells against the cancer cells.

The compositions disclosed herein may be formulated as pharmaceutical composition for administration to a subject in need thereof. Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants as known in the art. Further, the compositions may include preservatives. The compositions also may include buffering agents.

The pharmaceutical compositions may be administered therapeutically. In therapeutic applications, the pharmaceutical compositions are administered to a patient in an amount sufficient to elicit a therapeutic effect (e.g., an immune response to a tumor, which eradicates or at least partially arrests or slows growth of the tumor (i.e., a "therapeutically effective dose")).

The compositions disclosed herein may be delivered via a variety of routes. Typical delivery routes include parenteral administration (e.g., intratumoral, intravenous, intraperitoneal or otherwise). Formulations of the pharmaceutical compositions may include liquids (e.g., solutions and emulsions). The compositions disclosed herein may be co-administered or sequentially administered with other immunological, antigenic or vaccine or therapeutic compositions, including an adjuvant, or a chemical or biological agent given in combination with an antigen to enhance immunogenicity of the antigen. Additional therapeutic agents may include, but are not limited to, cytokines such as interferons (e.g., IFN-γ) and interleukins (e.g., IL-2).

EXAMPLES

The following examples are illustrative and are not intended to limit the disclosed and claimed subject matter.

Example 1

Reference is made to Makkouk et al., "Biodegradable Microparticles Loaded with Doxorubicin and CpG ODN for In Situ Immunization Against Cancer," AAPS Journal, Vol. 17, No. 1, January 2015 (published online Oct. 18, 2014), which is incorporated herein by reference in its entirety.

Abstract

In situ immunization is based on the concept that it is possible to break immune tolerance by inducing tumor cell death in situ in a manner that provides antigen-presenting cells such as dendritic cells (DCs) with a wide selection of tumor antigens that can then be presented to the immune system and result in a therapeutic anticancer immune response. We designed a comprehensive approach to in situ immunization using poly(lactic-co-glycolic acid) (PLGA)-biodegradable microparticles (MPs) loaded with doxorubicin (Dox) and CpG oligodeoxynucleotides (CpG) that deliver Dox (chemotherapy) and CpG (immunotherapy) in a sustained-release fashion when injected intratumorally. Dox induces immunogenic tumor cell death while CpG enhances tumor antigen presentation by DCs. PLGA MPs allow their safe co-delivery while evading the vesicant action of Dox. In vitro, we show that Dox/CpG MPs can kill B and T lymphoma cells and are less toxic to DCs. In vivo, Dox/CpG MPs combined with antibody therapy to enhance and maintain the T cell response generated systemic immune responses that suppressed injected and distant tumors in a murine B lymphoma model, leading to tumor-free mice. The combination regimen was also effective at reducing T cell lymphoma and melanoma tumor burdens. In conclusion, Dox/CpG MPs represent an efficient and safe tool for in situ immunization that could provide a promising component of immunotherapy for patients with a variety of types of cancer.

INTRODUCTION

Therapeutic cancer vaccination aims at overcoming immune tolerance to tumor-associated antigens (TAAs) and generating potent antitumor immune responses, most commonly in the form of effector T cells (1,2). This can be achieved via different approaches that include using TAAs mixed with adjuvants and using dendritic cells (DCs) loaded with tumor lysates (DC vaccination). However, the heterogenous expression of TAAs by tumors, suboptimal preparation conditions of tumor lysates for DC loading, inefficient migration of DCs to tumor sites post-infusion, and immunosuppressive mechanisms employed by tumors are major barriers against the establishment of long-lived robust immune responses (3-5).

In situ immunization is designed to overcome these challenges. It involves utilizing the patient's own tumor antigens by inducing tumor cell death in situ via intratumoral injection of cytotoxic agents. This potentially provides antigen-presenting cells such as DCs with a wide selection of tumor antigens (3). Moreover, the local delivery of cytotoxic agents assures a high concentration at the tumor environment and reduces systemic toxicity. An ideal in situ immunization design would include agents that not only kill tumor cells but also enhance DC maturation to ensure proper activation of antigen-specific T cells. To achieve this, we chose the combination of doxorubicin and unmethylated cytosine-phosphate-guanosine dinucleotides (CpG). Doxorubicin (Dox), a weak base with pKa 8.2, is a member of the anthracycline family of DNA-intercalating agents (6). It induces immunogenic tumor cell death by enhancing the expression of "eat-me" signals by tumor cells (most notably calreticulin), thus facilitating phagocytosis by DCs (7). Its dose-limiting cardiotoxicity, a major side effect of systemic administration (6), further strengthens the argument for its local delivery. In addition to immunogenic tumor cell death induced by Dox, administration of an adjuvant like CpG can further assist in the stimulation of a robust immune response. CpG mimics sequences found in bacterial DNA (8). It is a potent agonist of Toll-like receptor 9 (TLR9) that is expressed by B cells, monocytes, macrophages, and plasmacytoid DCs (pDCs). TLR9 stimulation induces DC maturation including upregulation of co-stimulatory molecules CD80 and CD86, allowing DCs to present tumor-derived antigens to T cells in an immunogenic instead of a tolerogenic context (9,10).

A major limitation for co-delivery of Dox and CpG is their opposite charges at physiological pH, which readily allow their aggregation in solution (11). This necessitates the development of a delivery system that can prevent the aggregation of Dox and CpG during co-administration. A recent attempt at developing a formulation for co-delivery of Dox and CpG included the complexation of Dox with a plasmid containing CpG motifs (12). Vaccination of mice carrying luciferase-expressing murine adenocarcinoma with Dox-CpG plasmid complexes showed reduced tumor proliferation as compared to mice treated with the Dox solution. However, this formulation failed to provide sustained release of Dox and CpG. Given the high potential for skin blistering (vesication) associated with local delivery of Dox (13), the development of a sustained-release delivery system is crucial to avoid this complication.

Biodegradable polymer particles are promising delivery systems for the development of injectable sustained-release formulations. Poly(lactic-co-glycolic acid) (PLGA) is one of the most successfully used biodegradable polymers. It is approved by the US FDA and European Medicine Agency (EMA) for various drug delivery systems in humans (14). Microparticles made of PLGA can be loaded with both Dox and CpG (Dox/CpG MPs) for efficient, intratumoral delivery of the two drugs without the risk of their precipitation. Moreover, the sustained release of Dox from PLGA particles should limit or eliminate vesication. Additionally, the immune adjuvant effect of PLGA itself has been shown in a number of reports (15). A size of 1 μm was selected for the MPs since it was reported to induce optimal NLRP3 inflammasome activation in DCs, which enhances cell-mediated immunity (16).

The in situ immunization approach utilized in this report is thus built to optimize intratumoral delivery of Dox/CpG MPs with the goal of breaking immune tolerance to tumor antigens and inducing an antitumor immune response. To maintain an activated T cell response, we also incorporated monoclonal antibodies that enhance T cell activation (anti-OX40) and overcome immunosuppression (anti-CTLA-4) in a comprehensive immunotherapy design that was tested both in vitro and in vivo.

Materials and Methods

Fabrication of PLGA Particles Encapsulating Dox and CpG (Dox/CpG MPs).

One to three milligrams of Dox (Sigma, Allentown, Pa.) was dissolved in 75 μL of 1% poly(vinyl alcohol) (PVA; Mowiol®; Sigma, Allentown, Pa.) solution. The primary emulsion was prepared by emulsifying this solution in 750 μL of dichloromethane (DCM) containing 100 mg of PLGA (Resomer® RG 503; Boehringer Ingelheim KG, Germany) using Sonic Dismembrator (Model FB 120 equipped with an ultrasonic converter probe CL-18; Fisher Scientific, Pittsburgh, Pa.) at 40% amplitude for 30 s. Similarly, 1 to 4 mg of endotoxin-free CpG oligodeoxynucleotides (CpG ODN) (5'-TCCATGACGTTCCTGACGTT-3', Integrated DNA Technologies, Coralville, Iowa) was dissolved in 75 μL of 1% PVA which was sonicated using the same conditions in 750 μL of DCM containing 100 mg of PLGA. The two primary emulsions were combined to get a compound primary emulsion, which was emulsified using the same settings in the Sonic Dismembrator into 8 mL of 1% PVA in 0.1 M ammonium acetate buffer (pH 8.4). This secondary emulsion was added to 22 mL of 1% PVA in 0.1 M ammonium acetate buffer (pH 8.4), which was stirred in the hood for 2 h for DCM to evaporate. Suspended particles were collected by centrifugation using Eppendorf Centrifuge 5804 R (Eppendorf, Westbury, N.Y.) at 5,000 rpm (4,500×g) for 5 min, resuspended in 30 mL of nanopure water, and washed twice with nanopure water. Particles were then suspended in 5 mL of nanopure water which was frozen at −20° C. for 4 h and lyophilized for 18 h with LABCONCO freeze dry system (FreeZone® 4.5 1, Model 7750020; Labconco Corporation, Kansas City, Mo.) at collector temperature of −53° C. and 0.08 mBar pressure. The initial amount of Dox or CpG required for the preparation was varied to obtain Dox/CpG MPs with different ratios of Dox and CpG encapsulated in PLGA particles.

PLGA particles encapsulating Dox (Dox MPs) were prepared as mentioned above except that the primary emulsion was prepared by sonication of 150 μL of 1% PVA containing Dox into 1.5 mL of DCM containing 200 mg of PLGA. In addition, the procedure for the preparation of Dox MPs was used to prepare blank PLGA particles (blank MPs) without the drug.

Characterization of MPs.

The morphology of the particles was examined using scanning electron microscope (SEM). Briefly, particle suspensions were placed on a silicon wafer mounted on SEM stubs. They were then coated with the gold-palladium by an argon beam K550 sputter coater (Emitech Ltd., Kent, England). Images were captured using the Hitachi S-4800 SEM at 5 kV accelerating voltage. The average size of particles was calculated from SEM images using ImageJ software (US National Institutes of Health, Md., USA) with n≥100. Powder X-ray diffraction (XRD) patterns of PLGA particles were obtained using a Bruker D-5000 diffractometer (Bruker AXS, Karlsruhe, Germany). Differential scanning calorimetry (DSC) analysis was performed using PerkinElmer DSC 7 (Alameda, Calif.) to study the physical state of lyophilized particles.

Quantification of Dox in Dox MPs and Dox/CpG MPs.

Quantification of Dox was performed using fluorescence spectroscopy. Briefly, different dilutions of Dox with known concentrations were prepared in DMSO. 100 μL of these standard solutions and samples were added to a 96-well plate. Fluorescence was measured at $\lambda_{ex}$ 470 nm and $\lambda_{em}$ 585 nm using SpectraMax® M5 multi-mode microplate reader (Molecular Devices, Sunnyvale, Calif.). A standard curve of Dox was used to estimate the concentration of Dox in samples.

Quantification of CpG in Dox/CpG MPs.

Quant-iT™ OliGreen® ssDNA Assay Kit (Invitrogen, Carlsbad, Calif.) was used according to the manufacturer's protocol to quantify CpG. Briefly, in a 96-well plate 100 μL of working reagent was added to 100 μL of standard CpG solutions of different concentrations and samples with unknown CpG concentration. The plate was then incubated at room temperature for 5 min in the dark. Fluorescence was measured at $\lambda_{ex}$ 480 nm and $\lambda_{em}$ 520 nm using a SpectraMax® M5 multi-mode microplate reader (Molecular Devices, Sunnyvale, Calif.). A standard curve of CpG was used to estimate the concentration of CpG in samples from the loading and release studies.

Loading of Dox and CpG in MPs.

For estimation of Dox loading, 10 mg of particles from each batch was dissolved in 1 mL of DMSO. The concentration of Dox was estimated as described above. For estimation of CpG loading, 20 mg of particles from each batch was treated with 0.2 N NaOH for 12 h. Once a clear solution was obtained, it was neutralized using 0.2 N HCl. The concentration of CpG was estimated as described above. Loading was calculated using Eq. 1. Multiple batches of Dox/CpG MPs were combined, and weight average of loading (Eq. 2) was calculated to obtain 4:1, 1:1, and 1:4 ratios of Dox/CpG in Dox/CpG MPs.

Eq. 1: Loading (µg/mg of MPs)=[Conc.×Vol.]/weight of MPs (mg) where, Conc.: Concentration of drug in samples (µg/mL) as calculated from the standard curve; Vol.: Volume of sample during the estimation of drug loading.

Eq. 2: Loading of drug=[(Weight$_{Batch1}$×Loading$_{Batch1}$)+(Weight$_{Batch2}$×Loading$_{Batch2}$)]/(Weight$_{Batch1}$+Weight$_{Batch2}$) where, Weight$_{Batch1}$ and Weight$_{Batch2}$ The weight of Dox/CpG MPs from batch 1 and batch 2, respectively Loading-$_{Batch1}$ and Loading$_{Batch2}$ Loading (µg/mg) of the drug in MPs from batch 1 and batch 2, respectively.

In Vitro Release of Dox and CpG from MPs.

Release studies were performed in phosphate-buffered saline (PBS) at pH 7.4 in a 37° C. incubator shaker at a speed of 200 rpm/min. Fifty milligrams of particles was added to 3 mL of PBS (optimal volume for performing repeated measurements of Dox and CpG release). Samples were collected at predetermined time points and the volumes removed were replaced by fresh PBS. Concentrations of Dox and CpG in samples were estimated as described above. At the end of the release study, the remaining drug in the PLGA particle matrix was extracted. The percentage released was calculated by normalizing the amount of drug released at each time point with the sum of the amount of drug release during the study and the amount of drug extracted from the particles at the end of the study. Percentage cumulative release of Dox and CpG was plotted with respect to time.

Evaluating the Cytotoxicity of Dox/CpG MPs in Tumor Cells and DCs In Vitro

Cell Lines.

The A20 cell line (a BALB/c B cell lymphoma) and the EL4 cell line (a C57BL/6 T cell lymphoma) were purchased from ATCC (Manassas, Va.). Tumor cells were cultured in RPMI-1640 medium (Gibco, Carlsbad, Calif.) supplemented with 10% heat-inactivated FCS (HyClone, Logan, Utah), 100 U/mL penicillin, 100 µg/mL streptomycin, and 50 µM 2-ME (All from Gibco), as complete medium.

To generate bone marrow-derived DCs (BMDCs), bone marrow cells were flushed from the tibias and femurs of BALB/c mice with complete medium, and mononuclear cells were isolated using Ficoll gradient separation (Fico/Lite-LM, Atlanta Biologicals, Flowery Branch, Ga.). Cells were cultured in McCoy's medium (Gibco) supplemented with 5 mL each Glutamax, MEM, and sodium pyruvate (all from Gibco) and 20 ng/mL each GM-CSF and IL-4 (PeproTech, Rocky Hill, N.J.) for 7 days to enrich for DCs. After 7 days, the nonadherent cells were harvested and used. Cells were >70% DCs as determined by CD11c staining by flow cytometry.

Viability Assay.

To determine the cytotoxic activity of MPs against A20 and EL4, the 3-(4,5 dimethylthiazol-2-yl)-5-(3-carboxymethoxyphenyl-2-(4-sulfophenyl)-2H-tetrazolium (MTS) assay for viability was conducted using CellTiter 96® AQueous Non-Radioactive Cell Proliferation Assay (Promega, Madison, Wis.). Five thousand A20 and EL4 cells were separately incubated with soluble Dox or Dox/CpG MPs (4:1 loading) in 96-well plates for 24, 48, and 72 h (four wells per group) at a final Dox concentration of 4.5 µg/mL. Media or blank MPs at equivalent weights were used as negative controls. The MTS/PMS reagent was then added for 4 h at 37° C. Following centrifugation, 80 µL of supernatant was removed to another 96-well plate. Absorbance was read at 490 nm using Thermomax Microplate Reader (Molecular Devices, Sunnyvale, Calif.). To directly compare the viability of A20, EL4, and BMDCs, cells were separately incubated for 24 h as described with Dox/CpG MPs (1:1 loading) at final Dox concentrations ranging from 0.28125 to 4.5 µg/mL. Media or blank MPs (average equivalent weight for highest and lowest concentrations) were used as control. Viability was assessed as before.

Percent survival was expressed as the ratio of absorbance of treated cells relative to that of untreated cells in media group (after subtracting the absorbance of the blank from each) multiplied by 100. Wells with equivalent drug or MP concentrations in absence of cells were used as blanks.

Evaluating the Efficacy of Dox/CpG MPs in Murine Tumor Models

Mice.

Mice (BALB/c and C57BL/six females, 6-8 weeks old) were purchased from Harlan Laboratories (Indianapolis, Ind.). All animal protocols used in these studies were approved by the Institutional Animal Care and Use Committee at the University of Iowa and complied with NIH Guidelines.

Tumor Models.

To examine local and systemic tumor regression following in situ immunization, the two-tumor A20 lymphoma model was used in BALB/c mice (17). Tumor cells were injected subcutaneously on opposite sides of the animal, with one tumor used for in situ immunization (injection of Dox/CpG MPs) and the contralateral tumor observed to assess systemic immune responses.

Seven to nine million A20 tumor cells in 100 µL sterile PBS were injected subcutaneously in the right and left flanks. Treatment began when tumors reached 5-7 mm in largest diameter, which typically occurred at days 9-10 after tumor inoculation. Two treatment protocols were assessed. In one protocol, mice received PBS (100 µL) or Dox/CpG MPs (2 or 10 µg Dox; 4:1 loading) in the left tumor and six intraperitoneal doses of anti-CTLA-4 (50 µg) given every 3-4 days. In another protocol, mice received PBS (100 µL) or Dox/CpG MPs (2 µg Dox and 1.5 µg CpG; 1:1 loading) in the left tumor and four intraperitoneal doses of anti-CTLA-4 (50 µg) and anti-OX40 (200 µg) given every 3-4 days. Anti-CTLA4 (hamster IgG, clone UC10-4F10-11) and anti-OX40 (rat IgG1, clone OX86) were purchased from BioXCell (West Lebanon, N.H.). The doses used are 50% of the conventional published dose (17) to reduce systemic toxicity.

To examine the efficacy of Dox/CpG MPs at reducing tumor burdens, the EL4 T lymphoma and the B16F10 melanoma single-tumor models were used. Dox/CpG MPs were administered as part of a therapy regimen that also included anti-CTLA-4 and anti-OX40 antibodies.

For the EL4 model, C57BL/6 mice were subcutaneously inoculated with EL4 at a dose of one million cells in 100 µL sterile PBS in the right flank. On day 4 post-inoculation, Dox/CpG MPs (4:1 loading) in 100 µL PBS were injected into the tumor site at a Dox dose of 2, 10, 50, or 100 µg. PBS (100 µL) was given to control groups. Antibodies were administered as detailed for the A20 tumor model.

B16-fLUC cells (a luciferase-expressing B16 cell line) were a generous gift from Noah Craft (University of California, Los Angeles) and were used as previously described (18). C57BL/6 mice were subcutaneously inoculated with 5×10$^4$ B16-fLUC cells in 100 µL of a 1:1 PBS/Matrigel mixture in the right flank. Treatment was started when tumor growth was noted using bioluminescent imaging. Briefly, mice were shaved and depilated (Nair®, Church & Dwight Co., Ewing, N.J.) one day prior to imaging. On the day of imaging, mice were injected intraperitoneally with 100 µL of 10 mg/mL of the luciferase substrate, d-luciferin (GoldBio.com, St. Louis, Mo.) in PBS, anesthetized via inhalation of oxygenated isoflurane, and imaged after 10 min using IVIS 200 (Caliper Life Sciences, Hopkinton, Mass.) with 4-min acquisition times using Living Image version 4.2 software (Caliper Life Sciences). Once tumors were established (~day 6 post-inoculation), Dox/CpG MPs (70 µg Dox and 288 µg CpG; 1:4 loading) in 100 µL PBS were injected into the tumor site. Abs were administered as previously described except that the full dose was used (100 µg for anti-CTLA-4 and 400 µg for anti-OX40).

In all tumor models, tumor growth was monitored by calipers and expressed as tumor area (length by width in square millimeters; $mm^2$). Mice were euthanized when tumors reached 20 mm in diameter in any direction.

Statistical Analysis.

All statistical analyses were performed using GraphPad Prism software, version 6.00 (San Diego, Calif.). Data were analyzed using paired or unpaired two-tailed Student's t tests, where appropriate. Comparisons of means between more than two groups were done by one- or two-way analysis of variance (with a Bonferroni post hoc test). Significance at $p<0.05$ is indicated by one asterisk; $p<0.01$ is indicated by two asterisks; and $p<0.001$ is indicated by three asterisks.

Results and Discussion

Fabrication and Characterization of Dox/CpG MPs.

A modified double emulsion solvent evaporation method was used for co-encapsulation of Dox and CpG in PLGA particles (FIG. 1a). All MPs demonstrated smooth morphology and a spherical shape (FIG. 1b). Examination of their release profile revealed that MPs showed burst release of encapsulated molecules followed by sustained release (FIG. 1c). PLGA particles with different loading ratios of Dox/CpG did not show differences in the percentage release of the encapsulated molecules for the range of loadings used for this work (data not shown). XRD patterns showed that all MPs are amorphous in nature, while DSC thermograms confirmed that Dox and CpG do not show any interaction with PLGA (data not shown). There was a significant difference in Dox release kinetics from Dox/CpG MPs and Dox MPs ($p<0.001$). In contrast, there was no significant difference in CpG release kinetics from Dox/CpG MPs and CpG MPs. Since Dox and CpG dissolved in water have opposite charges at neutral pH, the delay in the release of Dox from Dox/CpG MPs could be due to the formation of Dox and CpG complexes within the PLGA particle matrix that retard the diffusion of Dox.

Three different loading formulations were prepared (4:1, 1:1, and 1:4 Dox/CpG) (FIG. 1d) and tested in three different tumor models. Loadings were adjusted to the tumor aggressiveness in order to optimize the generated antitumor responses by optimizing the delivered doses of chemotherapy (Dox) and immunotherapy (CpG).

Dox/CpG MPs are Efficient at Killing Tumor Cells and are Less Toxic to BMDCs.

Figure 2:
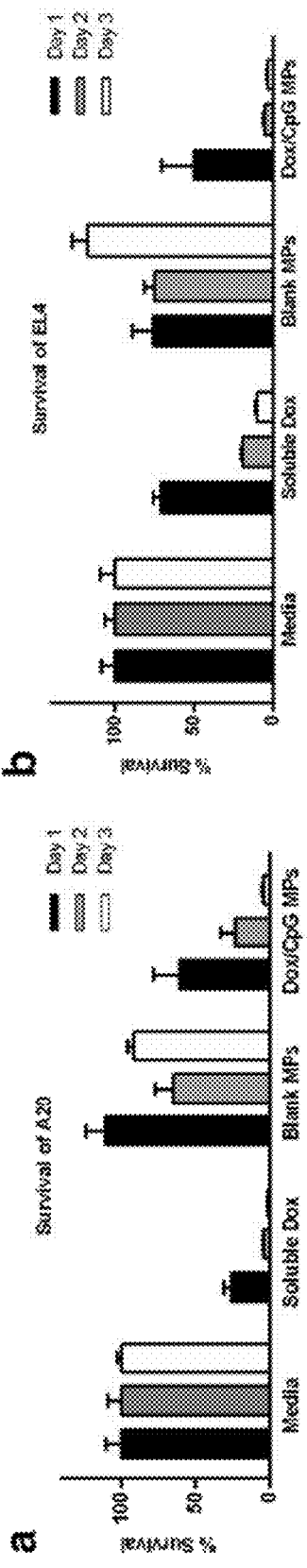

We studied the antitumor activity of Dox/CpG MPs in vitro by examining the viability of B cell (A20) and T cell (EL4) lymphoma cell lines post-exposure to the particles and comparing it to viability following exposure to the soluble drug (soluble Dox). The various statistical comparisons are summarized in FIG. 2. Within 24 h of incubation, A20 cells showed a dramatic decrease in viability in the presence of soluble Dox (FIG. 2a). A less dramatic but significant decrease was seen with Dox/CpG MPs. The sustained release of Dox from Dox/CpG MPs was evident in the slower decrease in viability of A20 incubated with Dox/CpG MPs over time (23% of A20 incubated with Dox/CpG MPs were viable on day 2 versus 61% on day 1; $p<0.05$) which was not seen with soluble Dox (4% of A20 incubated with soluble Dox were viable on day 2 versus 26% on day 1; not significant). We also observed that blank MPs were nontoxic to tumor cells over the 3-day incubation period (FIG. 2a). Similar results were seen with EL4 cells (FIG. 2b). More importantly, Dox/CpG MPs were as efficient as soluble Dox in inducing tumor cell death of both A20 (FIG. 2a) and EL4 (FIG. 2b). Collectively, these data indicate that Dox/CpG MPs are fully capable of substituting for soluble Dox for inducing tumor cell death.

Figure 3:
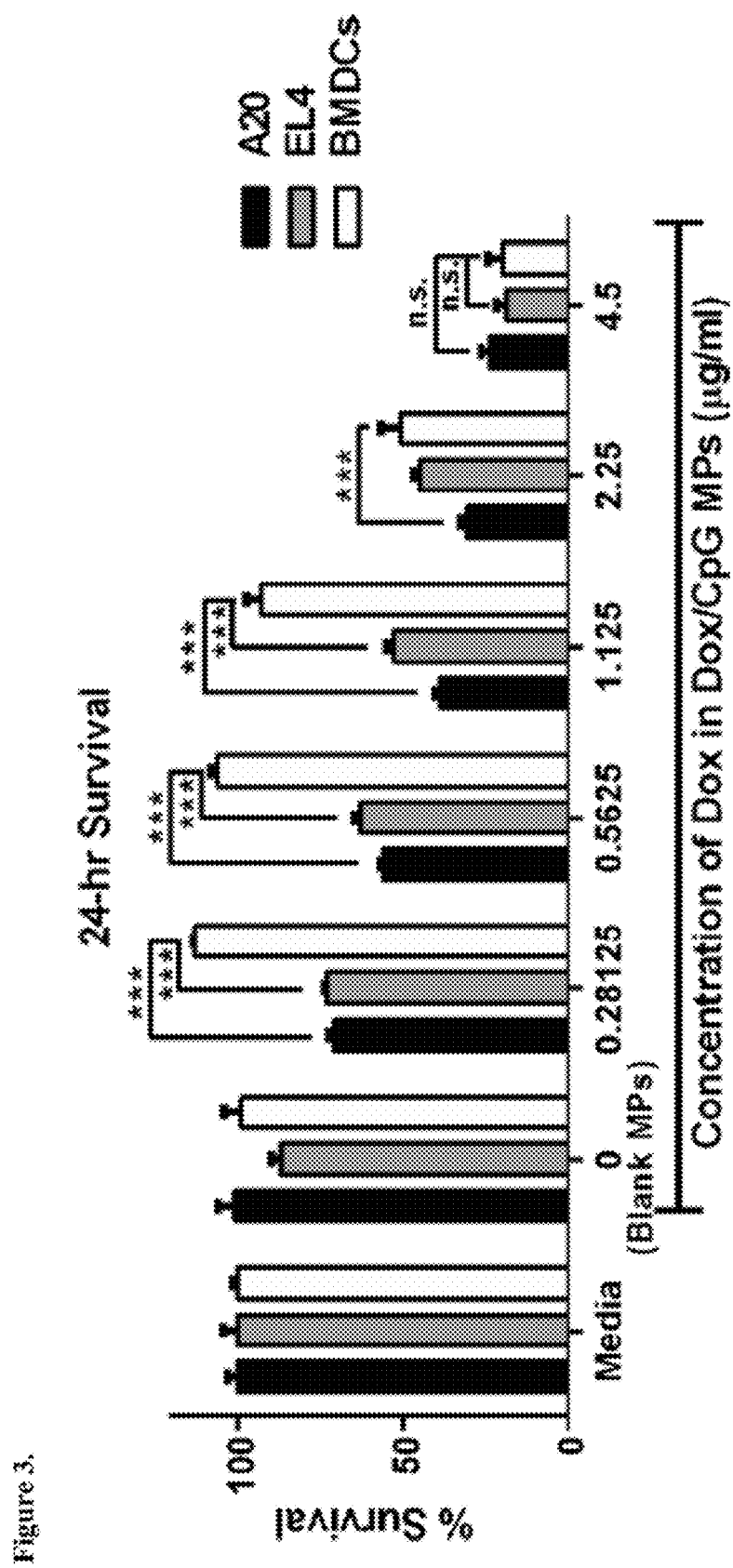

Given that Dox/CpG MPs are intended for delivery into the tumor which harbors tumor cells as well as infiltrating immune cells (most notably DCs), we evaluated the relative toxicity of Dox/CpG MPs to tumor cells and DCs (FIG. 3). Using BMDCs, we directly compared the viability of A20 and EL4 tumor cells to BMDCs over a 24-h incubation period with increasing concentrations of Dox/CpG MPs. Increasing concentrations of Dox/CpG MPs significantly reduced the viability of A20 and EL4 tumor cells (>70% survival at 4.5 µg/mL to <25% at 0.28125 µg/mL for both A20 and EL4; $p<0.0001$). Dox/CpG MPs were less cytotoxic to BMDCs than to A20 or EL4, as reflected by higher percent survival at low to intermediate concentrations (93% survival for BMDCs versus 53% for EL4 and 39% for A20 at 1.125 µg/mL Dox; $p<0.001$ for both). At high concentrations (4.5 µg/mL), Dox/CpG MPs were equally toxic to lymphoma cells and DCs (20% survival for BMDCs versus 19% for EL4 and 24% for A20; not significant for both). This suggests the injected dose and local concentration of Dox/CpG MPs have to be carefully considered, as higher concentrations may be detrimental to DCs that are responsible for initiating the antitumor immune response.

Low Doses of Dox/CpG MPs are More Efficient at Reducing A20 Tumor Burdens.

To validate the efficacy of Dox/CpG MPs in immunotherapy, we utilized Dox/CpG MPs in an in situ immunization regimen that impacts antitumor immune responses at multiple levels. This regimen consisted of intratumoral (i.t.) Dox/CpG MP injection combined with multiple injections of a systemic antibody that blocks CTLA-4 (anti-CTLA-4). Intratumorally, released Dox is expected to induce immunogenic tumor cell death, while released CpG enhances presentation of tumor-derived antigens by DCs. CTLA-4 is a co-inhibitory receptor that is constitutively expressed by regulatory T cells and is upregulated by T cells post-activation. A member of the immunoglobulin superfamily, it suppresses T cell activation and is employed by regulatory T cells to keep immune responses in check (19). As such, systemic anti-CTLA-4 administration can lead to long-lasting antitumor immunity by allowing activated tumor-specific T cells to remain activated longer.

Figure 4:
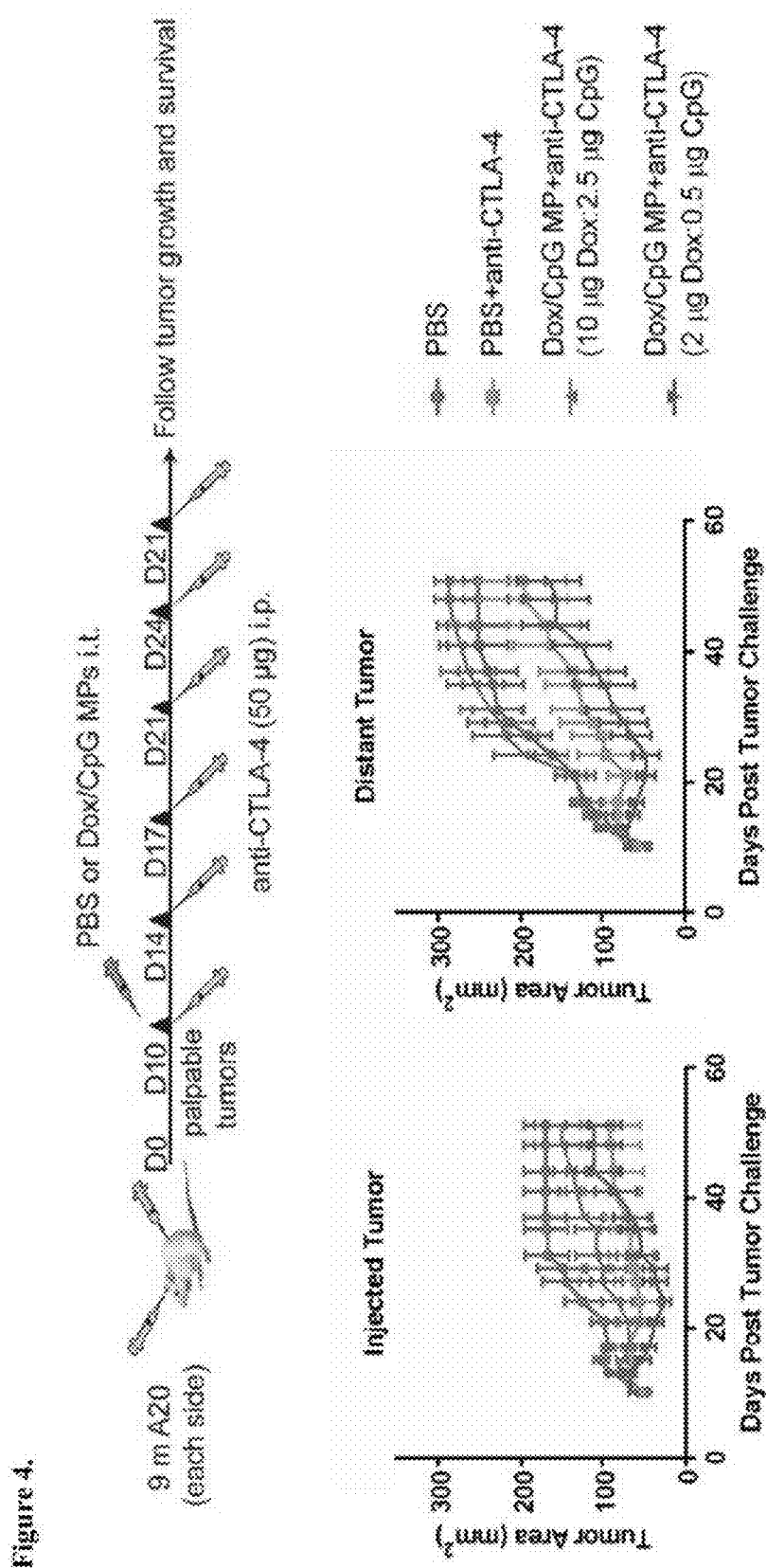

We tested the designed therapy regimen in vivo in BALB/c mice using the previously described two-tumor A20 lymphoma model used for in situ immunization (17) (FIG. 4). Mice were inoculated subcutaneously with A20 tumor cells on both flanks. Once tumors formed, one tumor was used for a single i.t. injection of Dox/CpG MPs in addition to six intraperitoneal (i.p.) injections of anti-CTLA-4 at half the published dose (50 µg) (17). The other (distant) tumor received no therapy and was monitored for signs of regression, which can only be attributed to systemic immune responses generated locally at the injected tumor.

We tested two doses of Dox/CpG MPs that delivered either 2 µg Dox (low-dose therapy) or 10 µg Dox (high-dose therapy) at a (4:1) loading (FIG. 4). Low-dose therapy with Dox/CpG MPs significantly reduced the injected tumor burden (p<0.01; low-dose therapy versus PBS between days 29 and 35 post-tumor challenge). Low-dose therapy also reduced distant tumor burdens (p<0.01; low-dose therapy versus PBS after day 29), suggesting that they are capable of inducing a systemic immune response. On the other hand, high-dose therapy was inefficient at reducing both local and distant tumor burdens. These data are in agreement with our in vitro data (FIG. 3) showing that high doses of Dox/CpG MPs can be lethal to DCs, thus abrogating the generation of an antitumor immune response.

Dox/CpG MPs Combined with Ab Generate Systemic Immune Responses that Eradicate Distant Tumors.

While low-dose therapy was more efficient than high-dose therapy, its beneficial effect was transient as tumors regrew (FIG. 4; low-dose tumors not significantly different from PBS tumors after day 44). This represented a limitation, since the goal was to generate long-lasting antitumor immune responses. Moreover, low-dose therapy was comparable to Ab therapy (PBS+Ab) at reducing both injected and distant tumors (p>0.05; not significant). As such, we sought to optimize our therapy design by increasing the CpG dose delivered to DCs via use of Dox/CpG MPs at the same optimized Dox dose (2 µg) but at (1:1) loading. This increased the delivered CpG dose threefold to 1.5 µg instead of 0.5 µg. We also enhanced the activated T cell immune responses by adding anti-OX40 to anti-CTLA-4. OX40 (CD134) is expressed by activated T cells, whose proliferation and survival can be enhanced using agonistic antibodies to OX40 (anti-OX40) (17). Furthermore, the combination of anti-CTLA-4 and anti-OX40 has been shown to enhance antitumor immune responses in murine lymphoma models (17). Since the activity of anti-CTLA-4 was being augmented by anti-OX40, and since our goal was to illustrate the benefits of local therapy without increasing systemic toxicity, we reduced the number of anti-CTLA-4 doses administered with anti-OX40 to four instead of six.

Figure 5:
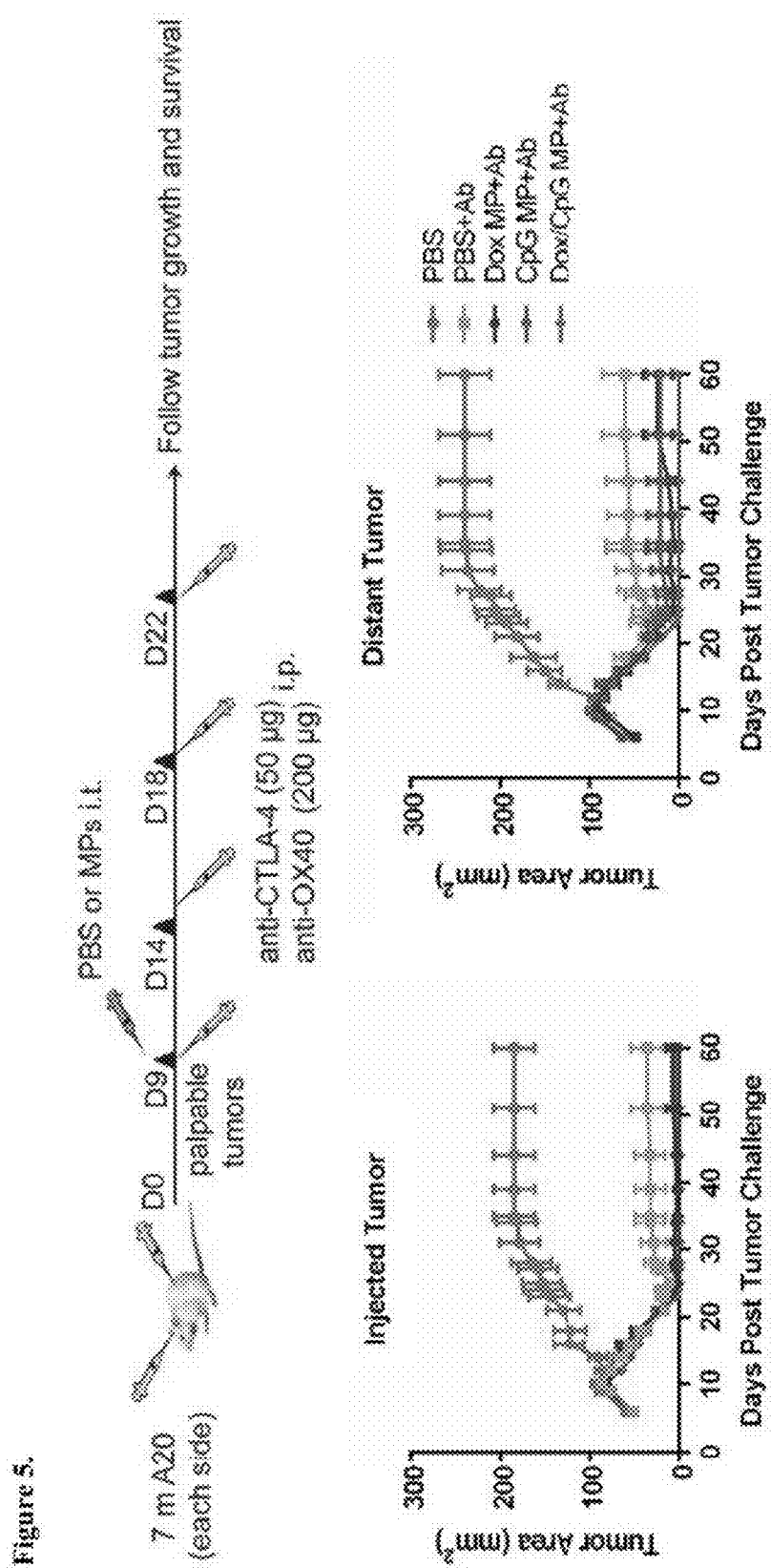

Using the A20 two-tumor model (FIG. 5), our optimized therapy of i.t. Dox/CpG MPs combined with i.p. anti-CTLA-4 and anti-OX40 antibodies (referred to as Ab) resulted in regression of both injected and distant tumors (100% of mice in Dox/CpG MP+Ab group became tumor-free). Ab therapy alone (PBS+Ab) was also capable of inducing regression of the injected tumor, as were Dox/CpG MPs administered with Ab therapy (p<0.0001 for all groups versus PBS starting day 16 post-tumor challenge). These data point to the antibodies (the common denominator in all groups) as the major contributor to the tumor regression seen. Indeed, Dox/CpG MPs administered without Ab therapy were incapable of inducing antitumor immune responses (data not shown).

However, Dox/CpG MP+Ab was significantly better than Ab therapy at eradicating distant tumors (p<0.01 by day 60 post-tumor challenge). This indicates that our optimized combination regimen with Dox/CpG MPs is more efficient than Ab therapy alone at generating long-lasting antitumor responses. Indeed, mice (n=5) that received Dox/CpG MP+Ab and became tumor-free were rechallenged with 10 million A20 tumor cells implanted subcutaneously at a different site from the MP-injected tumor at day 51 post-tumor challenge. None of the mice developed any tumors 22 days later (data not shown).

The combination of anti-CTLA-4 and anti-OX40 was shown by Houot el al. (17) to be effective as part of an in situ immunization regimen that uses multiple injections of soluble CpG i.t. totaling 500 µg. While the Houot therapy regimen similarly led to complete regression of both injected and contralateral tumors, our regimen used only 1.5 µg of CpG, an over 300-fold reduction in the CpG dose that was delivered in just one i.t. injection.

Dox/CpG MPs Combined with Ab are Efficient at Reducing EL4 Tumor Burdens.

Figure 6:
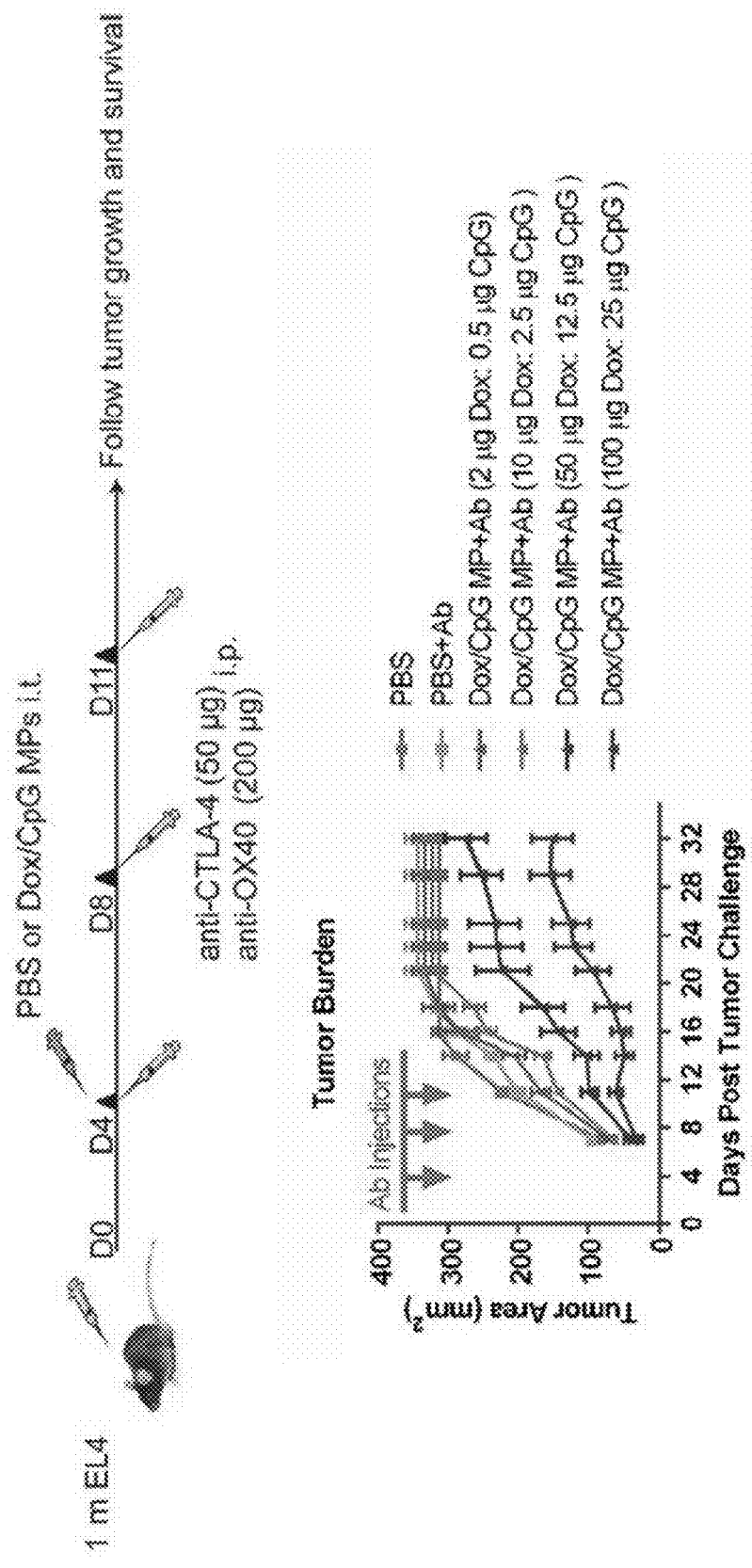
FIG. 6. Dox/CpG MPs combined with Ab are efficient at reducing EL4 tumor burdens. C57BL/6 mice (5-10 mice/group) were subcutaneously inoculated with EL4 at a dose of one million cells in the right flank. On day 4 post-inoculation, Dox/CpG MPs (4:1 loading) were injected into the tumor site at a Dox dose of 2, 10, 50, or 100 μg (corresponding CpG dose of 0.5, 2.5, 12.5, or 25 m). PBS was given to control groups. Anti-CTLA4 (50 μg) and anti-OX40 (200 μg) (collectively referred to as Ab) were administered by intraperitoneal injections of three doses given every 3-4 days, starting from day 1 of treatment. Mice were monitored for tumor growth and survival. Tumor areas are mean±SEM FIG. 7. Dox/CpG MPs combined with Ab are efficient at reducing B16 tumor burdens. C57BL/6 mice (five per group) were subcutaneously inoculated with $5 \times 10^4$ B16-fLUC (stable luciferase-expressing B16 cells) in a 1:1 PBS/Matrigel mixture in the right flank. Treatment was commenced when tumors were established (~day 6 post-inoculation), which was verified using bioluminescent imaging (IVIS). Mice received either no treatment (no Rx) or intratumoral Dox/CpG MPs (70 μg Dox and 288 μg CpG; 1:4 loading). Anti-CTLA-4 (100 μg) and anti-OX40 (400 μg) (collectively referred to as Ab) were administered i.p. in three doses as previously described except that the full dose was used. Mice were monitored for tumor growth and survival. Tumor areas are mean±SEM. *p<0.05; p<0.01; *p<0.001.

To validate the efficiency of Dox/CpG MPs in other tumor models, we tested Dox/CpG MPs in combination with anti-CTLA-4 and anti-OX40 in an EL4 T cell lymphoma tumor model (FIG. 6). Given that EL4 tumors are more aggressive than A20 tumors, higher MP doses (up to 100 µg Dox) were tested. Moreover, a single rather than a two-tumor model was used due to the fast growth rate of the distant tumor that necessitated sacrifice of the mice before the effect of a systemic immune response could be observed (data not shown).

The previously tested doses of Dox/CpG MPs (2 and 10 µg Dox) were inefficient at reducing EL4 tumor burdens, most likely due to the fast tumor progression rate. Using 50 µg Dox/CpG MPs combined with Ab therapy, the tumor burden was significantly reduced (p<0.0001; 50 µg Dox/CpG MP+Ab versus PBS between days 14 and 16 post-tumor challenge). 50 µg Dox/CpG MPs combined with Ab therapy were even more efficient than Ab therapy alone (p<0.0001; 50 µg Dox/CpG MP+Ab versus Ab therapy between days 16 and 18 post-tumor challenge). However, this impact was transient as tumors regrew after day 18. In contrast, using 100 µg Dox/CpG MPs combined with Ab therapy had a longer-lasting antitumor effect (significant differences between 100 µg Dox/CpG MP+Ab and PBS were seen until day 32 post-tumor challenge; p<0.001). 100 µg Dox/CpG MPs combined with Ab therapy was also significantly better than Ab therapy alone at reducing tumor burdens (p<0.0001; 100 µg Dox/CpG MP+Ab versus Ab therapy on day 32 post-tumor challenge) and was also more efficient than 50 µg Dox/CpG MPs (p<0.01; 100 µg Dox/CpG MP+Ab versus 50 µg Dox/CpG MP+Ab on day 32 post-tumor challenge). Collectively, these data indicate that in a more aggressive tumor model, higher doses of Dox/CpG MPs may be needed to control the rapidly dividing tumor cells.

Dox/CpG MPs Combined with Ab are Efficient at Reducing Melanoma Tumor Burdens.

Figure 7:
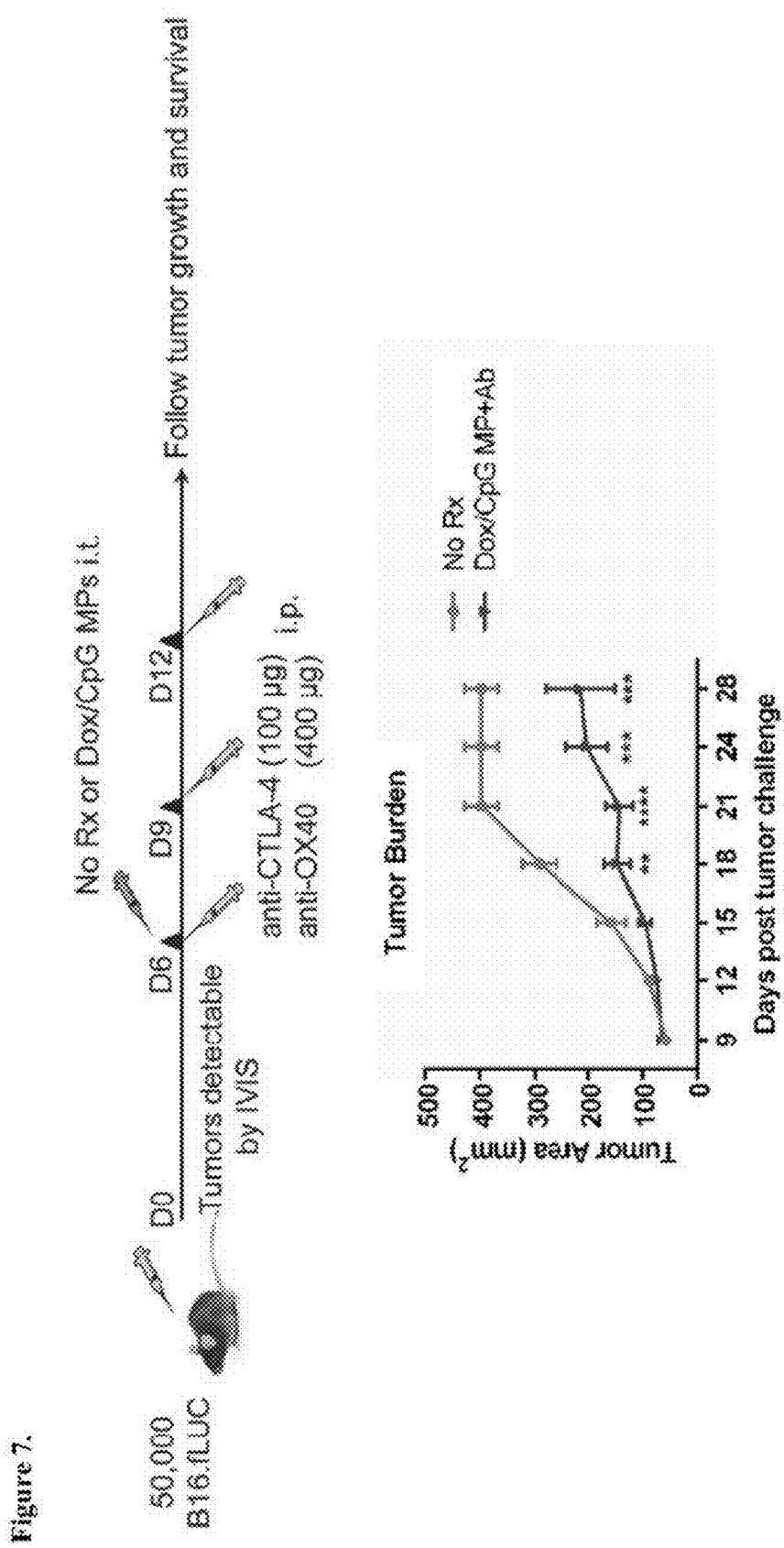

We also tested Dox/CpG MPs in a murine B16 melanoma tumor model (FIG. 7). While doxorubicin is not part of the standard care for melanoma patients as it is for lymphoma patients, our goal was to show that local chemotherapy can be used as part of an immunotherapy regimen to potentiate antitumor immune responses.

Because melanoma is an aggressive tumor, we used a single-tumor model similar to EL4. We also modified our therapy regimen by using 1:4 Dox/CpG MPs delivering a Dox dose of 70 µg and CpG dose of 288 µg and increased the doses of anti-CTLA-4 and anti-OX40 to 100% their published dose rather 50%. These adjustments were made to enhance the generated immune responses by further potentiating DC (via CpG) and T cell (via Ab) responses against the poorly immunogenic melanoma tumors.

Due to limitations of caliper measurements to detect established subcutaneous tumors (a palpable tumor may be measurable only when well over $10^6$ cells are present (18)), we evaluated the potential of our therapy using a B16 tumor line expressing firefly luciferase (B16-fLUC). This allows for verification of tumor establishment by bioluminescent imaging even before the tumor is palpable, which was necessary to confirm before treatment could be commenced.

Similar to the EL4 tumor model, Ab therapy (anti-CTLA-4+anti-OX40) alone tested in pilot experiments was inefficient at reducing tumor burdens at both 50 and 100% conventional dose (data not shown). On the other hand, Dox/CpG MPs combined with Ab therapy significantly reduced B16 tumor burdens as compared to untreated control mice.

CONCLUSION

As we learn more about cancer immunotherapy, and various immune manipulations are found to be effective not only in the laboratory but also in the clinic, studies exploring optimal ways to combine such treatments will be increasingly important. In the current study, we evaluated the potential value of MPs that contain both Dox and CpG as a component of cancer immunotherapy. Pilot studies were conducted to explore a large number of variables including drug doses, drug ratios, loading, polymer size, particle size, timing of exposure, etc. These studies were done in parallel in various systems including in vitro and in vivo evaluation. Given the large number of variables, it was not possible to optimize every parameter individually in every system. The overall goal of these studies was to highlight the feasibility of the overall approach. Once we identified reasonable parameters in each system, additional studies were done in that system using those parameters. Therefore, some of the details, such as loading, varied from model to model. Before this concept is translated to the clinic, additional optimization will need to be done to select the best single approach for each variable.

In vitro, we showed that Dox/CpG MPs are efficient at killing tumor cells and are less toxic to BMDCs. Using a B lymphoma two-tumor model, we found that Dox/CpG MPs combined with Ab therapy (anti-CTLA-4 and anti-OX40) are efficient at eradicating both local and distant tumors. We further validated the antitumor efficacy of this design in T cell lymphoma and melanoma tumor models, demonstrating that Dox/CpG MPs can reduce tumor burdens more efficiently than Ab therapy alone.

In situ immunization is appealing based on reduced systemic toxicity, potential for developing an immune response against a variety of endogenous tumor antigens, and ability to generate antigen-specific responses right at the tumor site (and so evade problems associated with trafficking of immune cells to the tumor). On the other hand, a major limitation is that it requires accessibility to the tumor site (20). It will also be important to assess the efficacy of in situ immunization, and duration of response, in de novo models where the tumors have greater heterogeneity and eventually in clinical trials.

In conclusion, our studies indicate MPs containing both Dox and CpG have promise as a component of in situ immunization and deserve further evaluation as a component of cancer immunotherapy.

REFERENCES

1. Topalian S L, Weiner G J, Pardoll D M. Cancer immunotherapy comes of age. J. Clin. Oncol Off J Am Soc Clin Oncol. 2011; 29(36):4828-36. doi: 10.1200JCO.2011.38.0899.
2. Galluzzi L, Vacchelli E, Eggermont A, Fridman W H, Galon J, Sautes-Fridman C, et al. Trial watch: adoptive cell transfer immunotherapy. Oncoimmunology. 2012; 1(3):306-15. doi: 10.4161/onci.19549.
3. Mellman I, Coukos G, Dranoff G. Cancer immunotherapy comes of age. Nature. 2011; 480(7378):480-9. doi: 10.1038/nature10673.
4. Vacchelli E, Martins I, Eggermont A, Fridman W H, Galon J, Sautes-Fridman C, et al. Trial watch: peptide vaccines in cancer therapy. Oncoimmunology. 2012; 1(9): 1557-76. doi: 10.4161/onci.22428.
5. Galluzzi L, Senovilla L, Vacchelli E, Eggermont A, Fridman W H, Galon J, et al. Trial watch: dendritic cell-based interventions for cancer therapy. Oncoimmunology. 2012; 1(7):1111-34. doi: 10.4161/onci.21494.
6. Hortobagyi G N. Anthracyclines in the treatment of cancer. An overview. Drugs. 1997; 54(Suppl 4):1-7. doi: 10.2165/00003495-199700544-00003.
7. Vacchelli E, Galluzzi L, Fridman W H, Galon J, Sautes-Fridman C, Tartour E, et al. Trial watch: chemotherapy with immunogenic cell death inducers. Oncoimmunology. 2012; 1(2):179-88. doi: 10.4161/onci.1.2.19026.
8. Krieg A M. From A to Z on CpG. Trends Immunol. 2002; 23(2):64-5. doi: 10.1016/S1471-4906(01)02150-0.
9. Galluzzi L, Vacchelli E, Eggermont A, Fridman W H, Galon J, Sautes-Fridman C, et al. Trial watch: experimental toll-like receptor agonists for cancer therapy. Oncoimmunology. 2012; 1(5):699-716. doi: 10.4161/onci.20696.
10. Zhang H, Liu L, Yu D, Kandimalla E R, Sun H B, Agrawal S, et al. An in situ autologous tumor vaccination with combined radiation therapy and TLR9 agonist therapy. PLoS One. 2012; 7(5):e38111. doi: 10.1371/journal.pone.0038111.
11. Geary S M, Krishnamachari Y, Lemke C, Salem A K, Weiner G J. Biodegradable particulate formulations. Google Patents; 2012.
12. Mizuno Y, Naoi T, Nishikawa M, Rattanakiat S, Hamaguchi N, Hashida M, et al. Simultaneous delivery of doxorubicin and immunostimulatory CpG motif to tumors using a plasmid DNA/doxorubicin complex in mice. J Control Release Off J Control Release Soc. 2010; 141(2): 252-9. doi: 10.1016/j.jconrel.2009.09.014.
13. Conde-Estevez D, Mateu-de A J. Treatment of anthracycline extravasations using dexrazoxane. Clin Transl Oncol Off Publ Fed Span Oncol Soc Natl Cancer Inst Mexico. 2014; 16(1):11-7.
14. Danhier F, Ansorena E, Silva J M, Coco R, Le Breton A, Preat V. PLGA-based nanoparticles: an overview of biomedical applications. J Control Release Off J Control Release Soc. 2012; 161(2):505-22. doi: 10.1016/j.jconrel.2012.01.043.
15. Yoshida M, Babensee J E. Poly(lactic-co-glycolic acid) enhances maturation of human monocyte-derived dendritic cells. J Biomed Mater Res A. 2004; 71(1):45-54. doi: 10.1002/jbm.a.30131.
16. Sharp F A, Ruane D, Claass B, Creagh E, Harris J, Malyala P, et al. Uptake of particulate vaccine adjuvants by dendritic cells activates the NALP3 inflammasome. Proc Natl Acad Sci USA. 2009; 106(3):870-5. doi: 10.1073/pnas.0804897106.
17. Houot R, Levy R. T-cell modulation combined with intratumoral CpG cures lymphoma in a mouse model without the need for chemotherapy. Blood. 2009; 113(15): 3546-52. doi: 10.1182/blood-2008-07-170274.
18. Craft N, Bruhn K W, Nguyen B D, Prins R, Liau L M, Collisson E A, et al. Bioluminescent imaging of melanoma in live mice. J Investig Dermatol. 2005; 125(1): 159-65. doi: 10.1111/j.0022-202X.2005.23759.x.
19. Wolchok J D, Yang A S, Weber J S. Immune regulatory antibodies: are they the next advance? Cancer J. 2010; 16(4):311-7. doi: 10.1097/PPO.0b013e3181eb3381.
20. Crittenden M R, Thanarajasingam U, Vile R G, Gough M J. Intratumoral immunotherapy: using the tumour against itself. Immunology. 2005; 114(1):11-22. doi: 10.1111/j.1365-2567.2004.02001.x.

Example 2

Reference is made to Makkouk et al., "Three Steps to Breaking Immune Tolerance to Lymphoma: A Microparticle Approach," Cancer Immunology Research, 2015; 3:389-398 (published online on Jan. 27, 2015), which is incorporated herein by reference in its entirety.

Abstract

In situ immunization aims at generating antitumor immune responses through manipulating the tumor microenvironment. Based on recent advances in the understanding of antitumor immunity, we designed a three-step approach to in situ immunization to lymphoma: (1) Inducing immunogenic tumor cell death with the chemotherapeutic drug Doxorubicin (Dox). Dox enhances the expression of "eat-me" signals by dying tumor cells, facilitating their phagocytosis by dendritic cells (DC). Due to the vesicant activity of Dox, microparticles (MP) made of biodegradable polymer Poly(lactide-co-glycolide or PLGA can safely deliver Dox intratumorally and are effective vaccine adjuvants; (2) Enhancing T-cell activation using anti-OX40; (3) Sustaining T-cell responses by checkpoint blockade using anti-CTLA-4. In vitro, Dox MPs were less cytotoxic to DCs than to B lymphoma cells, did not require internalization by tumor cells, and significantly enhanced phagocytosis of tumor cells by DCs as compared to soluble Dox. In mice, this three-step therapy induced CD4- and CD8-dependent systemic immune responses that enhanced T-cell infiltration into distant tumors leading to their eradication and significantly improving survival. Our findings demonstrate that systemic antitumor immune responses can be generated locally by three-step therapy and merit further investigation as an immunotherapy for lymphoma patients. In vitro, Dox MPs were less cytotoxic to DCs than to B-lymphoma cells, did not require internalization by the lymphoma cells, and significantly enhanced phagocytosis of tumor cells by DCs as compared to soluble Dox. In mice, this three-step therapy induced CD4- and CD8-dependent systemic immune responses that enhanced T cell infiltration into distant tumors leading to their eradication and significantly improving survival. Our findings demonstrate that systemic antitumor immune responses can be generated locally by three-step therapy and merit further investigation as an immunotherapy for lymphoma patients.

INTRODUCTION

The goal of many forms of cancer immunotherapy is to overcome immunologic tolerance to tumor antigens and generate immune responses in the form of effector T cells (1). In situ immunization is attractive because it utilizes the patient's unique tumor antigens by inducing tumor cell death in situ. This limits systemic drug toxicity and provides dendritic cells (DC) with a wide selection of tumor antigens to be presented to antigen-specific T cells (2, 3).

Recent advances in our understanding of antitumor immunity suggest generating a potent, long-lasting antitumor response might benefit from a three step approach. Step One—treatment would be delivered locally to induce tumor cell death and provide tumor antigens to DCs. Step Two—activation of tumor-specific T cells by DCs would be enhanced. Step Three—the activated T-cell response would be maintained so the systemic response can proceed unrestrained (2).

Doxorubicin (Dox) is an excellent candidate drug for enhancing tumor antigen uptake by DCs, and is routinely used for lymphoma (4). Dox induces immunogenic cell death which stimulates an immune response in part by inducing surface expression of calreticulin, an "eat-me" signal that enhances phagocytosis of dying tumor cells by DCs (5-7).

In order for T cells to be activated by DCs, they must also receive a costimulatory signal, which can be supplied by toll-like receptor (TLR) agonists (such as TLR9 agonist CpG), cytokines (such as IL2) and stimulatory antibodies that target members of the tumor necrosis factor receptor (TNFR) superfamily (such as OX40) (8-10). OX40 augments T-cell function and survival (10-12). A stimulatory antibody that activates OX40 (anti-OX40) could thus be used to further activate tumor-specific T cells. We chose to focus on anti-OX40 due to its demonstrated synergistic activity with anti-CTLA-4, which enhances antitumor immune responses in murine lymphoma models (13).

The activity of T cells is tightly regulated by checkpoints that control the magnitude of the immune response, exemplified by cytotoxic T-lymphocyte antigen 4 (CTLA-4). CTLA-4 is upregulated on activated T cells, and signaling via CTLA-4 reduces T-cell proliferation and activity (14). In addition, CTLA-4 plays a central role in the suppressive effect of regulatory T cells (Treg) (15). This provides strong rationale for including checkpoint blockade as a final step of in situ immunization.

While the use of Dox to induce immunogenic cell death is attractive for in situ immunization, an intratumoral injection of the soluble drug is not feasible due to its potent vesicant effects (16). Poly(lactide-co-glycolide) or PLGA is an FDA-approved biodegradable polymer that is clinically used in surgical sutures and for controlled delivery of therapeutic drugs (17). Following intratumoral injection, PLGA microparticles (MP) can provide sustained release of encapsulated molecules (18) into the tumor microenvironment without a vesicant effect. In addition, PLGA MPs are effective vaccine adjuvants. They activate the NALP3 inflammasome in DCs, which leads to IL1β secretion and the enhancement of innate and antigen-specific cellular immune responses (19).

Based on this background, we hypothesized that a three-step approach to in situ immunization (Dox MPs given intratumorally combined with systemic anti-CTLA-4 and anti-OX40) can elicit a systemic curative adaptive immune response.

Materials and Methods

Mice and Cell Lines.

Mice (BALB/c and C57BL/6 females, 6-8 weeks old) were purchased from Harlan Laboratories (Indianapolis, Ind.). All animal protocols were approved by the Institutional Animal Care and Use Committee at the University of Iowa and complied with NIH Guidelines.

A20 (murine BALB/c B-cell lymphoma), Raji (human Burkitt lymphoma B), and EL4 (murine C57BL/6 T-cell lymphoma) were purchased from American Type Culture Collection (ATCC, Manassas, Va.). Epstein-Barr virus (EBV)-transformed B cells were previously generated per standard protocols (20, 21). Subject informed consent was obtained in accordance with the Declaration of Helsinki under protocols approved by the institutional review board. Cells were cultured in RPMI-1640 medium (Gibco, Carlsbad, Calif.) supplemented with 10% heat-inactivated FCS (HyClone, Logan, Utah), 100 U/mL penicillin, 100 µg/mL streptomycin, and 50 µM 2-ME (Gibco). All cell lines used were confirmed to be Mycoplasma free. No additional validation assays were performed.

Therapeutic Antibodies.

Anti-CTLA4 (hamster IgG, clone UC10-4F10-11) and anti-OX40 (rat IgG1, clone OX86) were purchased from BioXCell (West Lebanon, N.H.). A20 were previously shown to lack surface expression of CTLA-4 and OX40 (13).

Generation of DCs.

To generate murine bone-marrow-derived DCs, bone marrow cells were flushed from tibias and femurs of BALB/c mice, and mononuclear cells isolated using Ficoll gradient separation (Fico/Lite-LM, Atlanta Biologicals, Flowery Branch, Ga.). Cells were cultured in medium supplemented with 20 ng/mL each GM-CSF and IL4 (PeproTech, Rocky Hill, N.J.) for 7 days. Non-adherent cells were harvested. Cells were >70% DCs as determined by CD11c staining.

Viability Assays.

The MTS assay for viability was used to determine the cytotoxic activity of Dox MPs against A20 and DCs (Promega, Madison, Wis.). Briefly, $5\times10^3$ A20 cells or DCs were incubated with Dox MPs (8 µg/mg) for 24, 48 or 72 h (4 wells per group) at a range of Dox concentrations. Blank MPs were used as negative controls. MTS was added for 4 h at 37° C. Following centrifugation, 90 µl of supernatant was removed. Absorbance was read at 490 nm using a Thermomax Microplate Reader (Molecular Devices, Sunnyvale, Calif.).

Rhodamine Particle Uptake.

Uptake of particles by A20 and DCs was determined using rhodamine-loaded MPs prepared similarly to Dox MPs. A20 and DCs were incubated for 24 h either alone or in a 1:1 mix with rhodamine-loaded MPs (0.5 µg/mL). Cells were washed and stained for CD11c-APC-Cy7 and CD19-APC (BD Biosciences (BD), San Jose, Calif.). Uptake was assessed by flow cytometry using LSR II flow cytometer (BD) by gating on rhodamine$^+$ DCs (CD11c$^+$) and A20 (CD19$^+$).

Transmission Electron Microscopy.

Uptake of Dox MPs was assessed using transmission electron microscopy (TEM). Briefly, A20 and DCs were incubated for 24 h with Dox MPs (1 µg/mL) or blank MPs (equivalent weight), washed with PBS and fixed in 2.5% glutaraldehyde in 0.1 M sodium cacodylate. Post-fixation was carried out in 1% osmium tetroxide with 1.5% potassium ferrocyanide for 2 hours, 2.5% uranyl acetate for 20 minutes, followed by dehydration in graded ethanol and embedding in Epon resin (Electron Microscopy Sciences, Hatfield, Pa.). Ultrathin sections were counterstained with uranyl acetate and lead citrate. TEM images were taken by JEOL JEM-1230 transmission electron microscope provided with Gatan UltraScan 1000 2 k×2 k CCD camera (JEOL USA, Inc., Peabody, Mass.). Micrographs were processed with ImageJ Software.

Phagocytosis Assay.

A20 phagocytosis was quantified using A20 cells labeled with CellTrace Violet (Invitrogen, Carlsbad, Calif.). Labeled A20 were left untreated or treated with Dox MPs for 48 h (3 wells per group) at various concentrations. Controls included soluble Dox (at the same concentrations) and blank MPs (at equivalent weights). Treated A20 were washed and co-incubated with DCs at a 1:1 ratio for 2 h, stained with anti-CD11c-APC-Cy7 (BD), and analyzed by flow cytometry. The percentage of double-positive cells (CD11c and CellTrace Violet) was determined.

Confocal Microscopy.

MP uptake by A20 cells was visualized by culturing cells for 24 h with Dox MPs at a final Dox concentration of 2.25 µg/mL. Cells were washed, incubated at 37° C. for 2 h with the nucleic acid dye Cyto16 (Invitrogen), washed, fixed, cytospun and mounted on Vectashield (Vector Laboratories, Burlingame, Calif.). DCs cultured on dishes with cover slide bottoms were treated for 3 h together with Cyto-16, then stained with anti-CD11c-APC (BD) for 2 h (4° C.) and visualized. Images were acquired with a Zeiss LSM510 confocal microscope (Carl Zeiss Co., Germany) equipped with a 63× oil-immersion objective and controlled by ZEN 2009 software (Zeiss). Images were processed with ImageJ Software.

In Vivo A20 Tumor Transplantation and Assessment.

BALB/c mice were subcutaneously inoculated with A20 at a dose of $6.7-9\times10^6$ A20 cells in 100 µL sterile PBS on the right and left flanks. Treatment began when tumors reached 5-7 mm in largest diameter (days 6-11 post inoculation). Tumor growth was monitored by calipers and expressed as length by width in square millimeters. Mice were euthanized when either tumor reached 20 mm in any direction or when tumor sites ulcerated.

A20 Tumor Immunotherapy.

Dox MPs (2 µg Dox in 100 µL PBS) or PBS (100 µL) were injected into the left flank tumor. Three doses of anti-CTLA-4 and anti-OX40 (collectively referred to as Ab) were administered by intraperitoneal injections every 3-4 days. Half the published doses were used (13): 50 µg for anti-CTLA-4 and 200 µg for anti-OX40 per injection. Treatment groups included PBS, PBS+anti-CTLA-4, PBS+anti-OX40, Dox MP, Dox MP+anti-CTLA-4, Dox MP+anti-OX40 and Dox MP+anti-CTLA-4+anti-OX40. Mice were treated and monitored as before. Additional studies were done with mice receiving lower doses of Ab.

CD4 and CD8 Depletion.

Anti-CD4 (rat IgG2b, clone GK1.5) and anti-CD8 (rat IgG2b, clone 2.43) were purchased from BioXCell (West Lebanon, N.H.). Rat IgG (MP Biomedicals LLC, Santa Ana, Calif.) was used as isotype control. Antibodies (200 µg per injection) were administered one day before therapy and on Days+1, +4, +8, +12 and +18. CD4 and CD8 T-cell depletion was validated by flow cytometry (>99% depletion).

Flow Cytometric Analysis of Tumors and Lymphoid Tissue.

Tumor and lymph node immune infiltrates were evaluated on Day 5 post therapy. Injected tumors, contralateral tumors and draining lymph nodes were harvested and single-cell suspensions surface stained with CD3-APC, CD4-FITC, CD8-PE-Cy7, IFNγ-PE, CD11b-PE, CD11c-APC-Cy7, CD44-APC, CD62L-PE (BD), Foxp3-APC and Gr-1-FITC (eBioscience, San Diego, Calif.) and fixed using BD Cytofix/Cytoperm.

Statistical Analysis.

GraphPad Prism software, version 6.0 (San Diego, Calif.) was used to analyze tumor growth and to determine differences between groups using unpaired 2-tailed Student t tests or ANOVA (Bonferroni correction) where appropriate. Survival curves were compared using the log-rank (Mantel-Cox) test.

Supplemental Methods

Fabrication of PLGA Particles Encapsulating Dox.

Doxorubicin microparticles (Dox MPs) were prepared using the double emulsion solvent evaporation method. Three to five milligrams of Doxorubicin hydrochloride (Dox) (Sigma, Allentown, Pa.) were dissolved in 150 μL of 1% poly(vinyl alcohol) (PVA; Mowiol®; Sigma) solution. The primary emulsion was prepared by emulsifying this solution in 1.5 mL of dicholromethane (DCM) containing 200 mg of PLGA (Resomer® RG 503; Boehringer Ingelheim KG, Germany) using Sonic Dismembrator (Model FB 120 equipped with an ultrasonic converter probe CL-18; Fisher Scientific, Pittsburgh, Pa.) at 40% amplitude for 30 seconds. This emulsion was again sonicated using the same settings into 8 mL of 1% PVA in 0.1 M ammonium acetate buffer at pH 8.4 (AmAc buffer). The resulting secondary emulsion was added to 22 mL of 1% PVA in AmAc buffer and stirred in the hood for 2 hours to allow for the evaporation of DCM. Suspended particles were collected by centrifugation using Eppendorf Centrifuge 5804 R (Eppendorf, Westbury, N.Y.) at 4500×g for 5 minutes. These particles were resuspended in 30 mL of nanopure water and centrifuged at 4500×g for 5 minutes. This step was repeated to wash PLGA particles. After washing, particles were suspended in 5 mL of nanopure water, frozen at −20° C. for 4 hours, and lyophilized for 18 hours with LABCONCO freeze dry system (FreeZone® 4.5 Liter, Model 7750020; Labconco Corporation, Kansas City, Mo.) at collector temperature of −53° C. and 0.08 mBar pressure. The loading of Dox in PLGA particles was optimized to ensure that the dose of Dox required for in situ immunization can be delivered with less than 200 μg of PLGA particles. The fabrication procedure showed 62.2±11.7% encapsulation efficiency that produced Dox MPs with 12.3±3.6 μg of Dox encapsulated per mg of PLGA particles. Thus, only 163 μg of Dox MPs were required to deliver 2 μg of Dox per mouse for in situ immunization. Blank PLGA particles were prepared using the above mentioned procedure in the absence of Dox.

Characterization of MPs.

The morphology of the particles was examined using Scanning Electron Microscopy (SEM). Briefly, particle suspensions were placed on a silicon wafer mounted on SEM stubs. They were then coated with the gold-palladium by an argon beam K550 sputter coater (Emitech Ltd., Kent, England). Images were captured using the Hitachi S-4800 SEM at 5 kV accelerating voltage. The average size of particles was calculated from SEM images using ImageJ software (U.S. National Institutes of Health, Maryland, USA) with n≥100.

Quantification of Dox in MPs.

Quantification of Dox loading in MPs was performed using fluorescence spectroscopy. Briefly, different dilutions of soluble Dox with known concentrations (in the range of 1-100 ug/mL) were prepared in DMSO. Ten milligrams of particles were dissolved in 1 mL of DMSO. Equal volumes of these standard solutions and samples were added to a 96-well plate. Fluorescence was measured at $\lambda_{ex}$=470 nm and $\lambda_{em}$=585 nm using SpectraMax® M5 multi-mode microplate reader (Molecular Devices, Sunnyvale, Calif.). Loading was calculated using equation 1 and the encapsulation efficiency of the double emulsion solvent evaporation process was calculated using equation 2.

Loading (μg/mg of MPs)=[Concentration of Dox in sample×Volume of sample]/weight of MPs used for the assay (mg)  Equation 1

Encapsulation Efficiency=[Weight of MPs (mg)× Loading (μg/mg)×100]/Initial weight of Dox used for the preparation (μg)  Equation 2:

In-Vitro Release of Dox from MPs.

Kinetic release studies were performed in phosphate buffer saline (PBS) at pH 7.4 in a 37° C. incubator shaker at a speed of 200 rpm. 50 mg of particles was added to 3 mL of PBS. Samples were collected at predetermined time points and the volumes removed were replaced by fresh PBS. Concentrations of Dox in samples were estimated as described above except that the standard solution of Dox was prepared in PBS. Percentage cumulative release of Dox was plotted with respect to time.

Generation of MDDCs.

To generate human monocyte-derived dendritic cells (MDDCs), monocytes were isolated from peripheral blood mononuclear cells (PBMCs) of healthy volunteers by MACS negative selection using the human Monocyte Isolation Kit II (Miltenyi Biotec, Auburn, Calif.). MDDCs were prepared from the same donor of EBV-transformed B cells to maintain an autologous system. Freshly isolated monocytes were incubated with 1000 U/mL GM-CSF and 500 U/mL IL-4 (both from PeproTech, Rocky Hill, N.J.) for 6 days to generate MDDCs. Cells were >95% MDDCs as determined by CD11c staining.

Viability Assays.

The cytotoxic activity of Dox MPs against human tumor cells was determined using the Annexin V/propidium iodide assay. Raji and EBV-transformed B cells were plated at 1×10$^5$ cells/mL and incubated for 3 days with increasing concentrations of either soluble Dox or Dox MPs (13 μg/mg). Cells were transferred to FACs tubes and an equal number of beads (CaliBRITE PerCP beads, BD Biosciences) were added to each tube. Cells were stained with Annexin V-FITC (BD Biosciences) and propidium iodide (PI) (Sigma-Aldrich, St. Louis, Mo.) and analyzed by flow cytometry using a FACScan (BD Biosciences). Data was analyzed using FlowJo software (version 8.8.6; Tree Star, Stanford, Calif.) and expressed as the number of viable cells (Annexin V$^-$ PI$^-$) normalized to the number of beads.

Phagocytosis Assay.

Phagocytosis of EBV-transformed B cells was quantified using a simultaneous incubation system where MDDCs and autologous EBV-transformed B cells were simultaneously incubated and treated together. Briefly, EBV-transformed B cells were labeled with CFSE (Invitrogen, Carlsbad, Calif.) then co-cultured with MDDCs at a 1:1 ratio and either soluble Dox or Dox MPs (100 ng/mL) for 22.5 hours. Media or blank MPs (equivalent weight) were used as controls. Cells were stained with CD11c-PE-Cy5 (BD Biosciences) and visualized by flow cytometry on a FACScan. Data was analyzed using FlowJo software. Note that at the very low Dox concentrations used in human cell lines, Dox and CFSE fluorescence could be distinguishable and were therefore compatible.

Confocal Microscopy.

To visualize phagocytosis of A20 cells by DCs, A20 were labeled with Vybrant DiO (Molecular Probes, Eugene, Oreg.). Labeled cells were cultured with no treatment or with blank MPs (equivalent weight), soluble Dox or Dox MPs at a final Dox concentration of 9 μg/mL for 24 h. After washing, A20s were co-incubated with DCs (1:1) in dishes with cover slide bottoms for 3 h. DCs were rendered visible by staining for CD11c.

For EBV-transformed B cells, CFSE-labeled cells were treated with soluble Dox, blank or Dox MPs at a final Dox concentration of 50 ng/mL or left untreated for 48 h. After washing, cells were co-incubated with MDDCs (1:1) for two hours to allow for phagocytosis, followed by staining with CD11c-PE-Cy5. Cells were then fixed in 2% paraformaldehyde, cytospun (4000 rpm for 10 min), mounted on Vectashield, and visualized by confocal microscopy.

Tumor Histology.

Freshly harvested tumors were frozen in OCT. Frozen samples were sectioned on a cryostat at 10 µm and stained with hematoxylin and eosin. A necrosis score was assigned to each tumor sample based on the following scoring system: 1, <25% of tumor mass is necrotic; 2, 25%-75% of tumor mass is necrotic; and 3, >75% of tumor mass is necrotic.

Examination of Tumor-Specific T Cell Responses.

Mice were inoculated with A20 tumors and treated as detailed. Treatments consisted of PBS, PBS+Ab, Dox MP, or Dox MP+Ab. On Day 7 post therapy, spleens and draining lymph nodes of both injected and contralateral tumors were harvested separately and made into single-cell suspensions. Red blood cells in splenic samples were lysed. A20 cells were irradiated with a dose of 150 Gy (25 Gy/min dose rate) using a $^{137}$Cs source (JL Shepherd, San Fernando, Calif.). Radiation was performed at the Radiation and Free Radical Research Core of the University of Iowa.

A total of $1\times10^6$ splenocytes or lymph node cells were cocultured with $2\times10^5$ irradiated A20 cells (150 Gy) for 24 hours at 37° C. and 5% $CO_2$. Brefeldin A (Sigma) was added during the last 6 hours of culture at 1 µg/mL. Afterward, cells were washed and surface stained for CD3 and CD8. Intracellular IFN-γ expression was assessed using BD Cytofix/Cytoperm kit (BD Biosciences) per instructions.

EL4 Tumor Model.

C57BL/6 mice were subcutaneously inoculated with EL4 at a dose of one million cells in 100 µL sterile PBS in the right flank. On Day 4 post-inoculation, Dox MPs (25 µg Dox) in 100 µL PBS were injected into the tumor site (n=10). PBS (100 µL) was given to control mice (n=5). Antibodies were administered as detailed for the A20 tumor model. Mice were treated and monitored as before.

Results

Dox MPs Provide Sustained Release of Dox.

Figure 15:
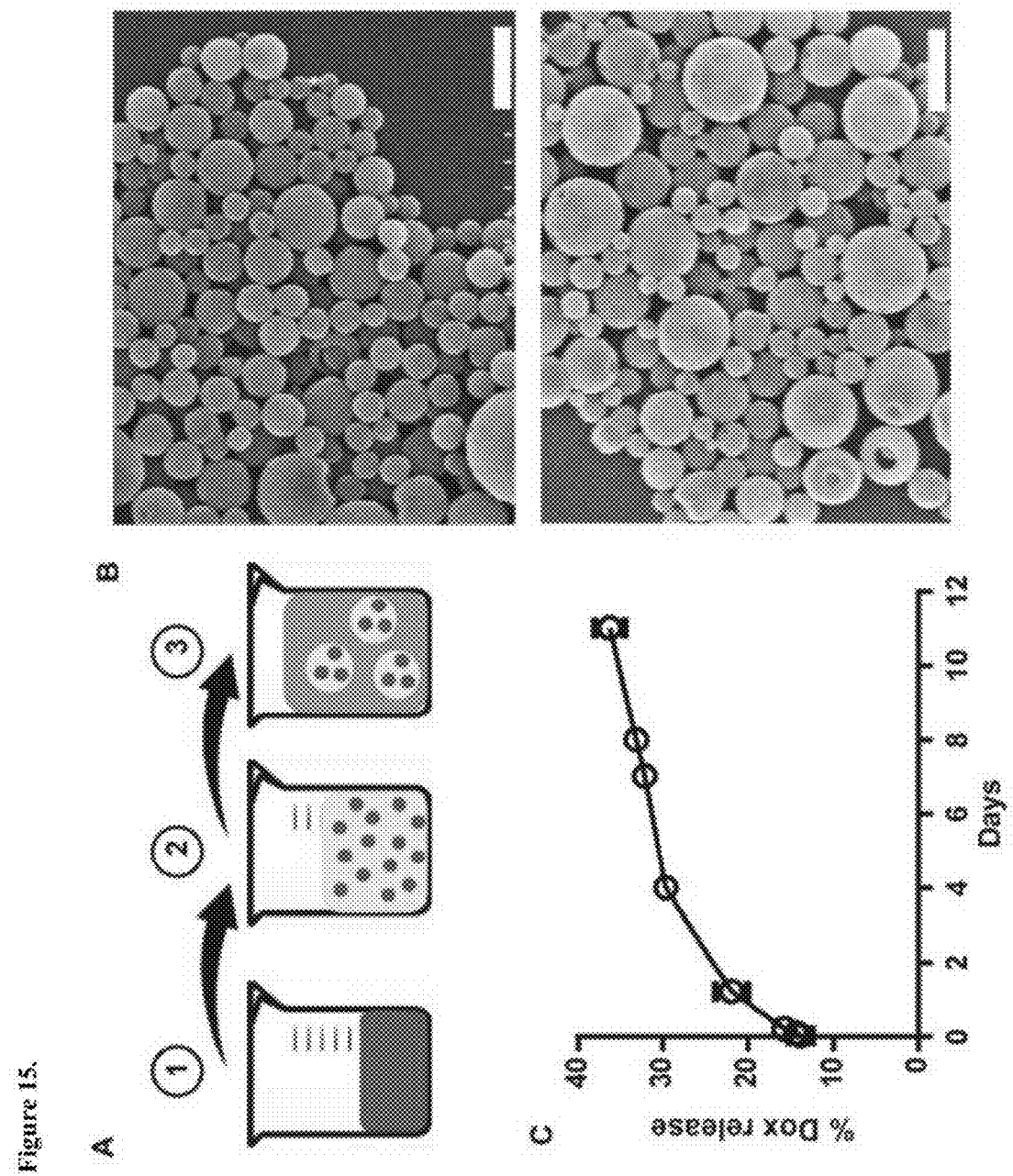
FIG. 15. Synthesis and characterization of Dox MPs. S1A. Double emulsion solvent evaporation method for the preparation of Dox loaded PLGA particles. Dox is dissolved in 1% PVA solution in water (1) which is emulsified in PLGA solution in DCM (2). This emulsion is again emulsified into 1% PVA solution (3) which is allowed to stir in a hood for evaporation of DCM, leaving a suspension of PLGA particles. The particles are then collected by centrifugation. S1B. Scanning electron microscopy (SEM) microphotographs of blank MPs (top panel) and Dox MPs (lower panel). The scale bar on the lower right represents 2 μm length. S1C. Release kinetics of Dox from PLGA particles. Dox MPs were added to PBS (pH 7.4) at 37° C. in an incubator shaker. Samples of released Dox were collected at regular intervals to estimate time-dependent release. Results are mean±SEM (n=3).

Dox MPs were prepared by the double emulsion solvent evaporation method (22) (FIG. 15A). The target particle size was 1 µm based on ability to promote inflammasome activation in DCs (19). Scanning electron microscopy revealed a smooth morphology and spherical shape (FIG. 15B). Particle size was 1.2±0.4 µm, which is comparable to the size of blank MPs (empty MPs) of 1.4±0.3 µm. Kinetic release studies showed 13% burst release of Dox within one hour followed by sustained release as the polymer underwent degradation (FIG. 15C).

Dox MPs Kill Tumor Cells More Slowly than Soluble Dox and are Less Cytotoxic to DCs.

Dox MPs and soluble Dox were compared for their ability to kill A20 lymphoma cells. Increasing concentrations of soluble Dox led to a significant decrease in A20 viability within 24 h of exposure (87% at 0.5625 µg/mL versus 46% at 1.125 µg/mL on Day 1; p<0.0001) (FIG. 8A). A less pronounced decrease in A20 viability was seen with Dox MPs (97% at 0.5625 µg/mL versus 84% at 1.125 µg/mL Dox on Day 1; not statistically significant). This was confirmed when comparing Dox MPs to soluble Dox (46% with soluble Dox versus 84% with Dox MPs at 1.125 µg/mL; p<0.0001) and also after 48 h exposure (5% with soluble Dox versus 24% with Dox MPs at 1.125 µg/mL on Day 2; p<0.0001). These data indicate that Dox MPs kill A20 cells more slowly than soluble Dox. Moreover, tumor cells had an average survival of 82% following three days of incubation with blank MPs, indicating that PLGA MPs are not toxic to tumor cells.

Upon injection into the tumor microenvironment, both tumor cells and immune cells would be exposed to Dox released from degrading MPs. Therefore, we evaluated the effect of Dox MPs and soluble Dox on DCs. Dox MPs were less cytotoxic to DCs than to A20 (24 h survival at 1.125 µg/mL Dox—23% for A20 versus 81% for DCs; p<0.05). On the other hand, soluble Dox was equally cytotoxic to both (26% survival for A20 versus 19% for DCs; not statistically significant) (FIG. 8B). By 72 h, lower concentrations of Dox MPs were still significantly more cytotoxic to A20 than to DCs (0% survival for A20 versus 74% for DCs at 0.28125 µg/mL; p<0.001), while higher concentrations were cytotoxic to both (0% survival for A20 versus 10% for DCs at 2.25 µg/mL; not statistically significant). This suggests careful titration of Dox MP doses will be important to identify the window where Dox MPs are toxic to malignant cells but not to DCs in the tumor.

Dox MPs are Cytotoxic Despite Limited Internalization.

Figure 9:
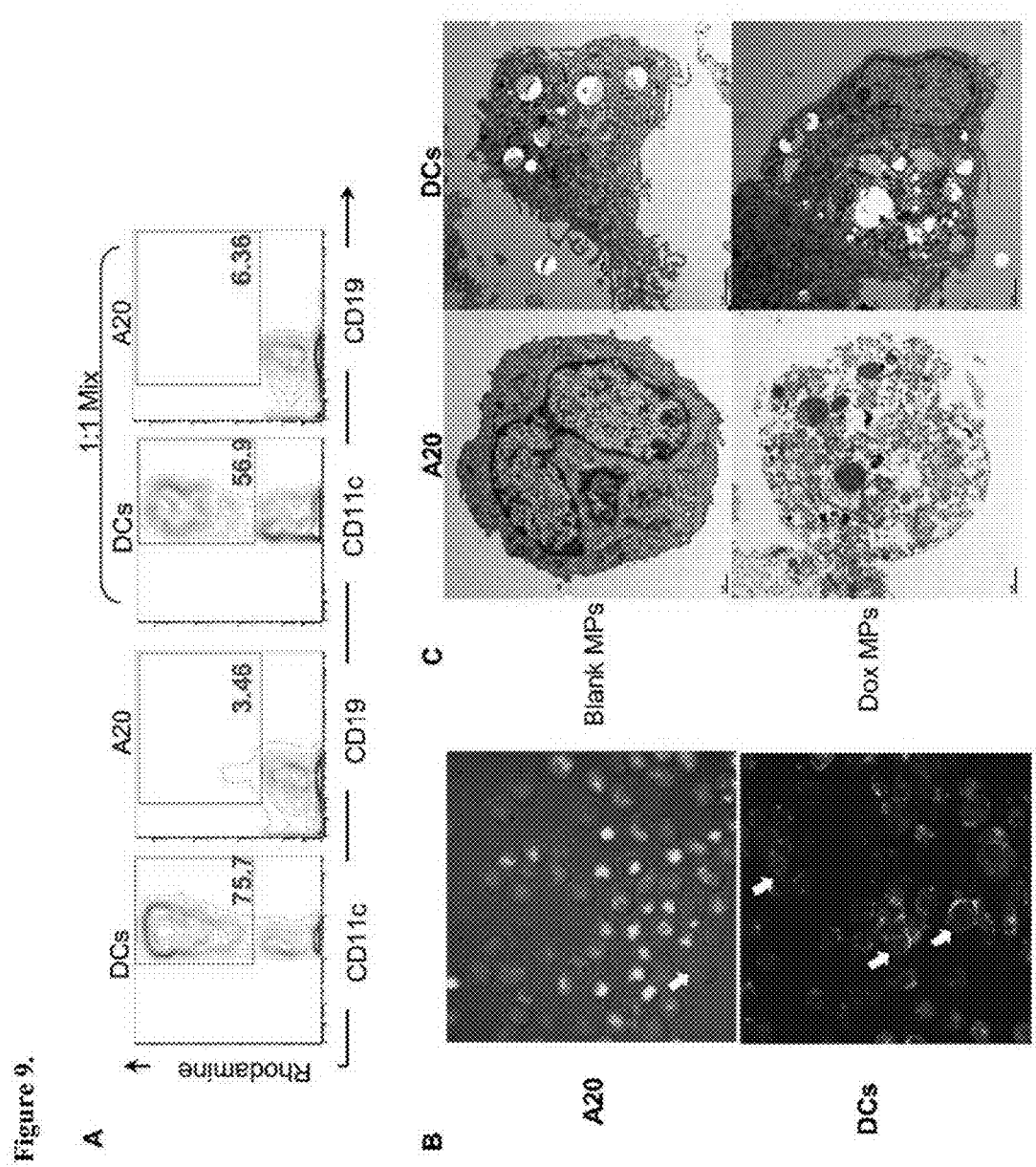
FIG. 9. Dox MPs do not require internalization by tumor cells for their cytotoxic activity. 2A. A20 and DCs were cultured alone or in a 1:1 mix with rhodamine-loaded MPs for 24 h. Uptake was assessed by flow cytometry by gating on Rhodamine+ BMDCs (CD11c+) and A20 (CD19+). Representative flow plots are shown. 2B. A20 were cultured for 24 h with no treatment or with Dox MPs at a final Dox concentration of 2.25 μg/mL. Cells were washed, stained with Cyto-16 (nucleic acid dye), cytospun and visualized by confocal microscopy. DCs were similarly treated, stained with Cyto-16 and anti-CD11c, and visualized. Representative images of Dox MP treatment are shown (×400). White arrows point to cells with internalized Dox MPs. 2C. A20 and DCs were cultured for 24 h with no treatment or with blank MPs (equivalent weight) or Dox MPs at a final Dox concentration of 1 μg/mL. Cells were washed, fixed and analyzed by TEM. Representative images for blank MP and Dox MP treatments are shown. Arrows point to MPs (scale bar: 1 μm for A20 and 2 μm for DCs).

To evaluate whether MPs are internalized by cells, we utilized rhodamine-labeled MPs and tracked their uptake by tumor cells and DCs by flow cytometry (FIG. 9A). A20 tumor cells did not internalize MPs, which is in agreement with published reports (23). In contrast, DCs readily took up the particles even when cocultured with tumor cells. Similar results were found with Dox MPs taking advantage of the natural fluorescence of Dox (24) (FIG. 9B).

Internalization and cytotoxicity were not strongly linked. A20 tumor cells incubated with Dox MPs showed signs of cytotoxicity (dissolution of cellular organelles, increased chromatin clumping and nuclear fragmentation, and blebbing of nuclear and plasma membranes) despite limited internalization while DCs readily took up MPs (red arrows) but showed little toxicity (FIG. 9C). Collectively, these data show that Dox MPs do not require internalization for their cytotoxic activity but rather release the encapsulated drug locally, which is then taken up by tumor cells. In addition, various cells in the tumor microenvironment can have different levels of sensitivity to the slow release of Dox by the MPs.

Dox MPs Enhance Phagocytosis of Tumor Cells by DCs.

Figure 10:
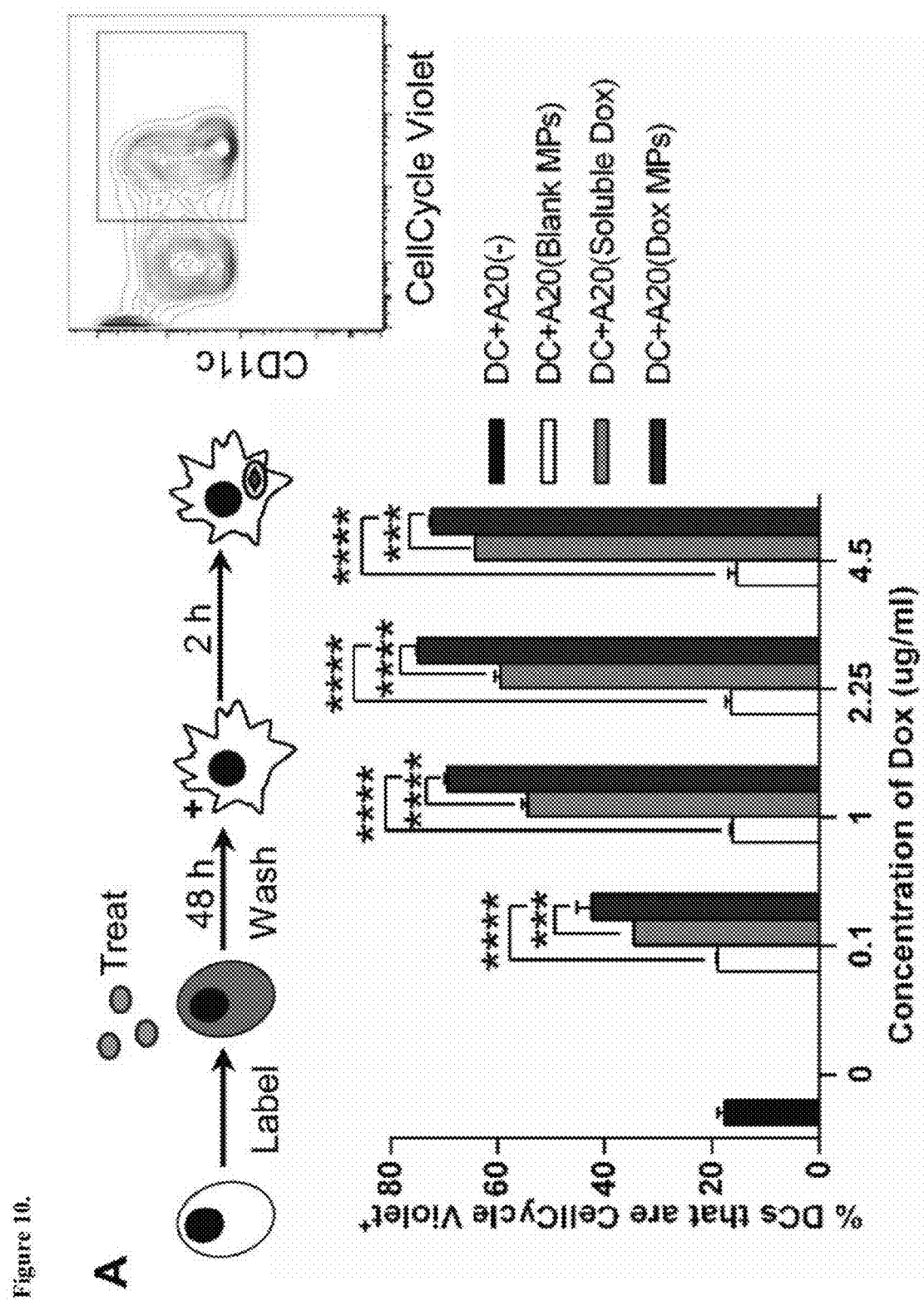
FIG. 10. Dox MPs enhance phagocytosis of tumor cells by DCs. A20 were labeled with CellCycle Violet then left untreated or treated with soluble Dox, blank MPs or Dox MPs for 48 h. Cells were washed, co-incubated with DCs (1:1 ratio) for 2 h, stained for CD11c and evaluated by flow cytometry. Cells were gated on CD11c+ CellCycle Violet+. Results are mean±SEM (n=2). *p<0.001; **p<0.0001.
Figure 16:
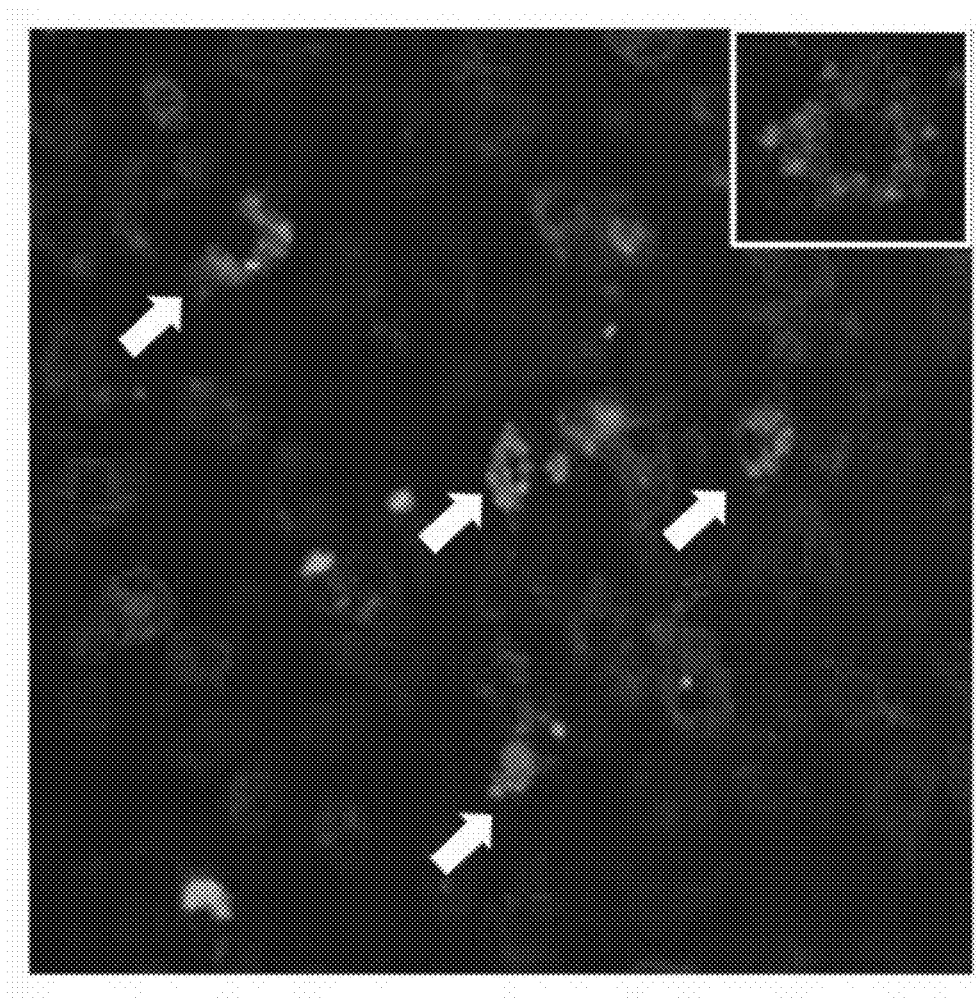
FIG. 16. Dox MPs enhance phagocytosis of A20 by DCs. A20 were labeled with DiO then cultured with no treatment or with blank MPs (equivalent weight), soluble Dox or Dox MPs at a final Dox concentration of 9 μg/mL for 24 h. Cells were washed, co-incubated with DCs (1:1) for 3 h, stained for CD11c and evaluated by confocal microscopy. Representative image of Dox MP treatment is shown (×400). White arrows point to DCs that have phagocytosed tumor cells. Inset: Higher magnification of a DC (×630).

We next evaluated whether Dox MPs enhance phagocytosis of tumor cells by DCs in a manner similar to that seen with soluble Dox (7). Increasing concentrations of Dox enhanced phagocytosis of A20 cells treated with both soluble Dox and Dox MPs. However, Dox MPs were superior to soluble Dox at all concentrations tested (p<0.001) (FIG. 10A). Phagocytosis was also visualized by confocal microscopy (FIG. 16). Together, these results show that Dox MPs are superior to soluble Dox in inducing phagocytosis of tumor cells by DCs.

Dox MPs Exert Similar Effects to Soluble Dox in Human Cell Lines.

Figure 17:
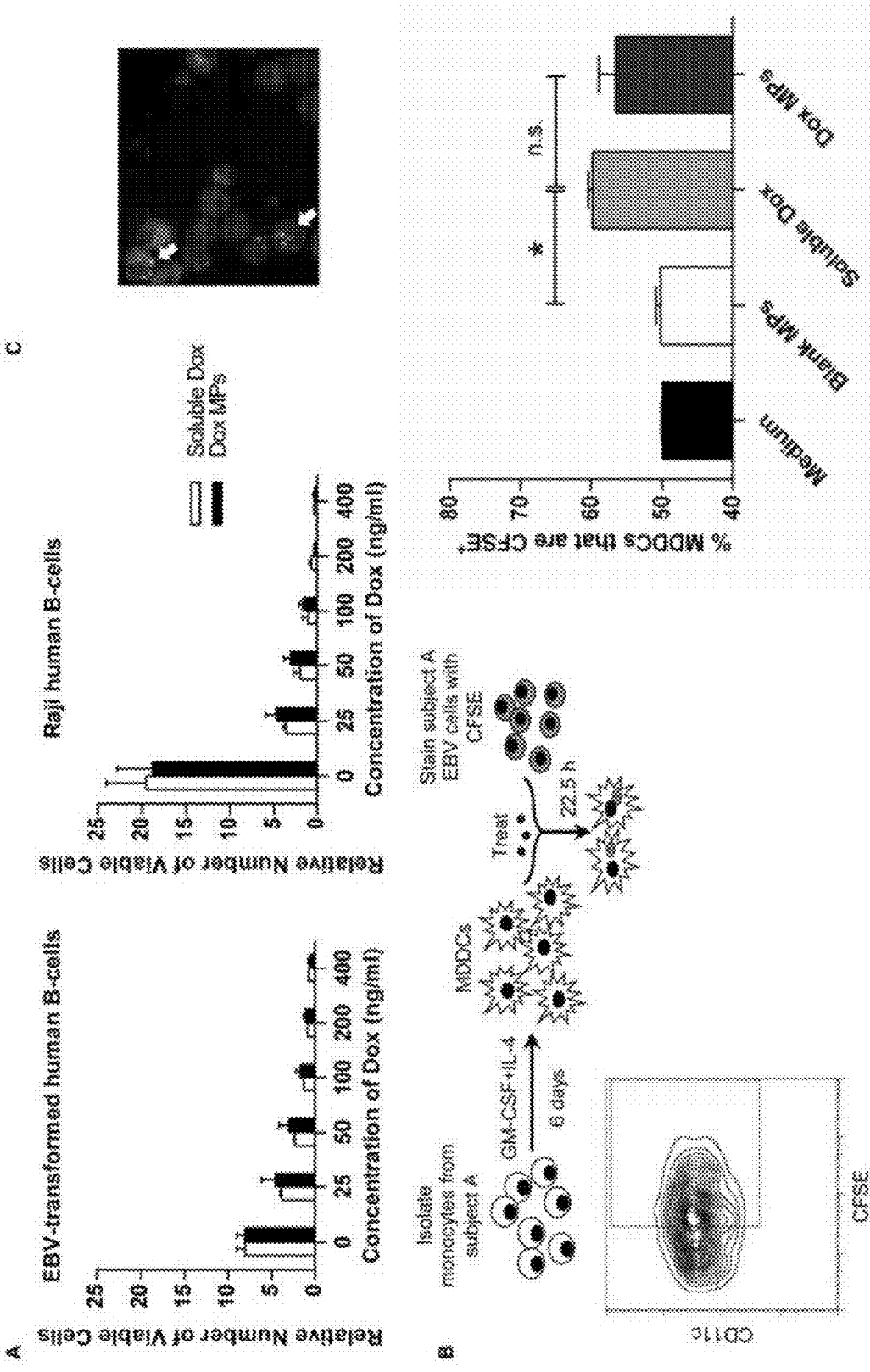
FIG. 17. Dox MPs exert similar effects to soluble Dox in human cell lines. S3A. Human EBV-transformed and Raji B cells were incubated for 3 days with increasing concentrations of either soluble Dox or Dox MPs. Media or blank MPs (equivalent weight) were used as controls. Viability was assessed by Annexin V and propidium iodide staining and is expressed as the relative number of viable cells (normalized to calibration beads). Data shown are pooled from two independent experiments. Results are mean±SEM (n=4). S3B. Myeloid-derived dendritic cells (MDDCs) were prepared from freshly isolated human monocytes by culturing for 6 days with GM-CSF and IL-4. MDDCs were simultaneously incubated with autologous CFSE-labeled EBV-transformed B cells (1:1 ratio) and either soluble Dox or Dox MPs (100 ng/mL) for 22.5 hours. Media or blank MPs (equivalent weight) were used as controls. Cells were stained for CD11c and evaluated by flow cytometry. Cells were gated on CD11c$^+$ CFSE$^+$. Results are mean±SEM (n=2). *p<0.05; n.s. not significant. S3C. EBV-transformed B cells were labeled with CFSE then left untreated or treated with soluble Dox or blank or Dox MPs at a final Dox concentration of 50 ng/mL for 48 h. After washing, cells were co-incubated with MDDCs (1:1) for 2 h, stained for CD11c, cytospun and visualized by confocal microscopy. Representative image of Dox MP treatment is shown (×400). White arrows point to DCs that have phagocytosed tumor cells.

We also evaluated the effect of Dox MPs on human cell lines using Dox concentrations comparable to peak plasma concentrations achieved in lymphoma patients (278 ng/mL at 30 mg/m$^2$ Dox) (25). Dox MPs were similar to soluble Dox in their killing efficiency of EBV-transformed and Raji B cells (FIG. 17A). Dox MPs were also similar to soluble Dox at inducing the phagocytosis of EBV-transformed B cells by autologous myeloid-derived dendritic cells (MDDC) when EBV-transformed B cells and MDDCs were simultaneously incubated with Dox or Dox MPs (FIG. 17B, C).

Three-Step Therapy Eradicates Distant Tumors and Enhances Survival.

To examine the induction of systemic immune responses, we utilized a two-tumor lymphoma model similar to that established by Houot and colleagues (13). Mice were inoculated subcutaneously with A20 cells on both flanks, with one site used for in situ immunization (injection of Dox MPs)

and the contralateral site observed to assess the systemic antitumor response. In this model, regression of the contralateral tumor can only be due to systemic immune responses.

Figure 11:
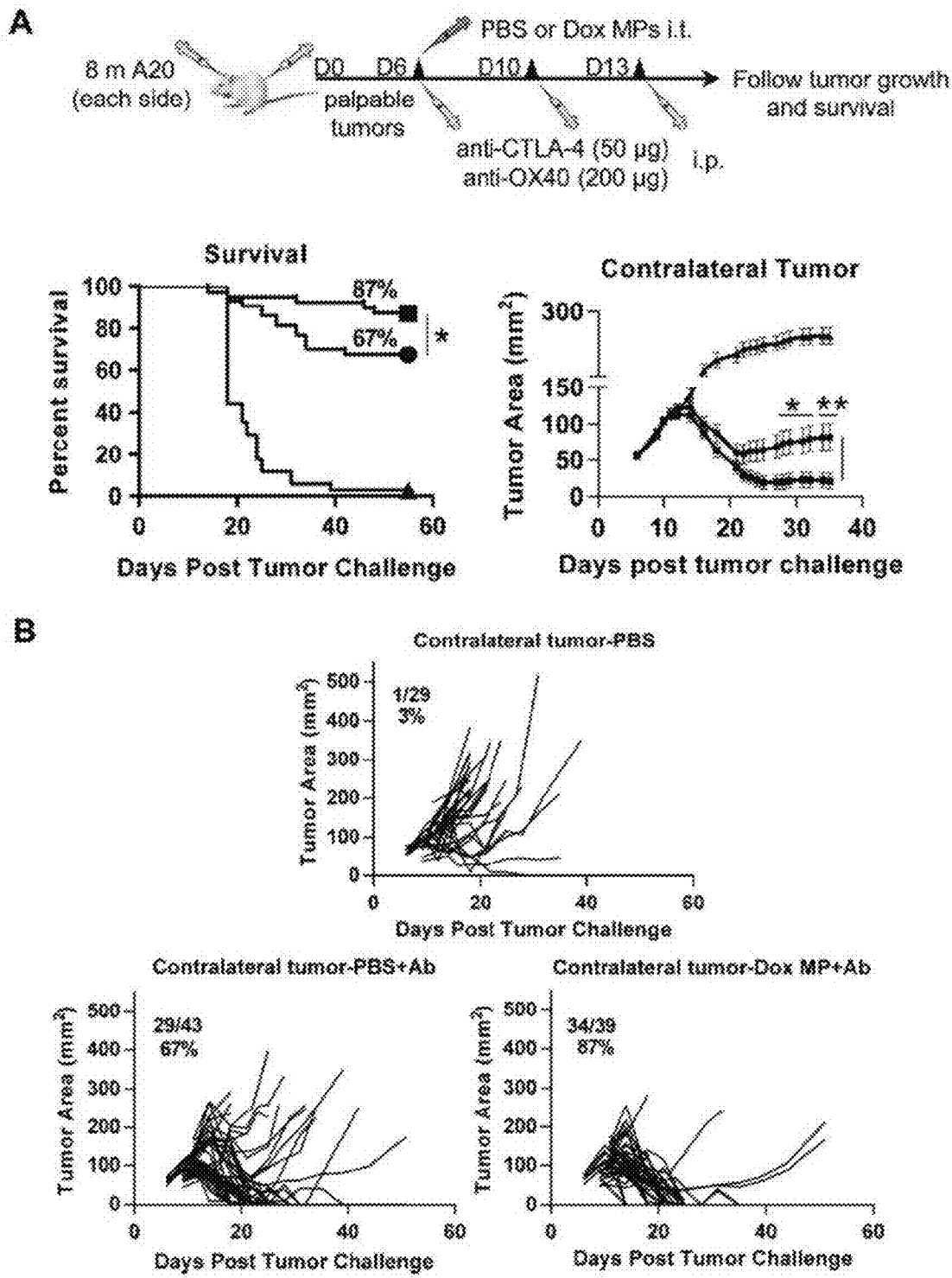
FIG. 11. Three-step therapy eradicates distant tumors and enhances survival. 4A. Eight million A20 cells were injected subcutaneously into each flank of BALB/c mice (6-12/group). Treatment began when tumors reached 5-7 mm in largest diameter (typically between days 6 and 11). Left-side tumors were injected with PBS or Dox MPs (2 μg Dox). Mice also received three intraperitoneal injections of anti-CTLA-4 (50 μg) and anti-OX40 (200 μg) over 10 days (collectively referred to as Ab). The systemic antitumor immune response was assessed by measuring the size of the contralateral tumor and disease-free survival. Tumor areas are mean±SEM. Data shown are pooled from four independent experiments. *p<0.05; **p<0.01. 4B. Spider plots representing tumor size for individual mice per group. Fractions and percentages represent mice that were tumor-free at Day 55 post tumor challenge. Symbols: Triangle (PBS); circle (PBS+Ab); and square (Dox MP+Ab).

We first evaluated the effect of Dox MP alone. No mice receiving Dox MPs showed any signs of skin ulceration/necrosis even at doses as high as 100 µg Dox, confirming that the sustained release properties of the MPs protect mice from the vesicant effect of Dox. While local tumors regressed following treatment with intratumoral Dox MPs, no systemic antitumor response was observed (as measured by regression of contralateral tumors). We then evaluated the combination of Dox MPs plus antibody therapy. Mice received a single intratumoral injection of Dox MPs and three systemic injections of anti-CTLA-4 and anti-OX40 (collectively referred to as Ab). Control group mice received intratumoral PBS with or without Ab. Initial studies revealed that systemic immune responses were not generated when Dox MPs were used at a dose of 100 µg Dox. Dose titration revealed systemic antitumor responses were generated with a lower dose of Dox MPs (2 µg) (FIG. 11), in agreement with our in vitro data demonstrating high doses of Dox MPs are detrimental to both tumor cells and DCs. These data also demonstrate that the systemic antitumor response is not due to systemic release of Dox into the circulation, which would have resulted in a greater therapeutic effect on the contralateral tumor with higher doses of Dox MPs.

Mice treated with the optimized dose of Dox MPs (2 µg Dox) combined with Ab had significantly enhanced tumor-free survival as compared to mice receiving Ab therapy only (87% versus 67%; p<0.05) (FIG. 11A). This therapy generated a potent systemic immune response that eradicated most of the contralateral tumors (FIG. 11A, B). Mice that received Dox MP+Ab and became tumor-free were re-challenged with 10 million A20 tumor cells implanted subcutaneously at a different site from the MP-injected tumor at Day 51 post tumor-challenge (n=5). These mice remained tumor-free demonstrating a long-term memory response (data not shown).

Three-Step Therapy Induces CD4- and CD8-Dependent Immune Responses and Requires all Therapy Components for Maximum Efficiency.

Figure 12:
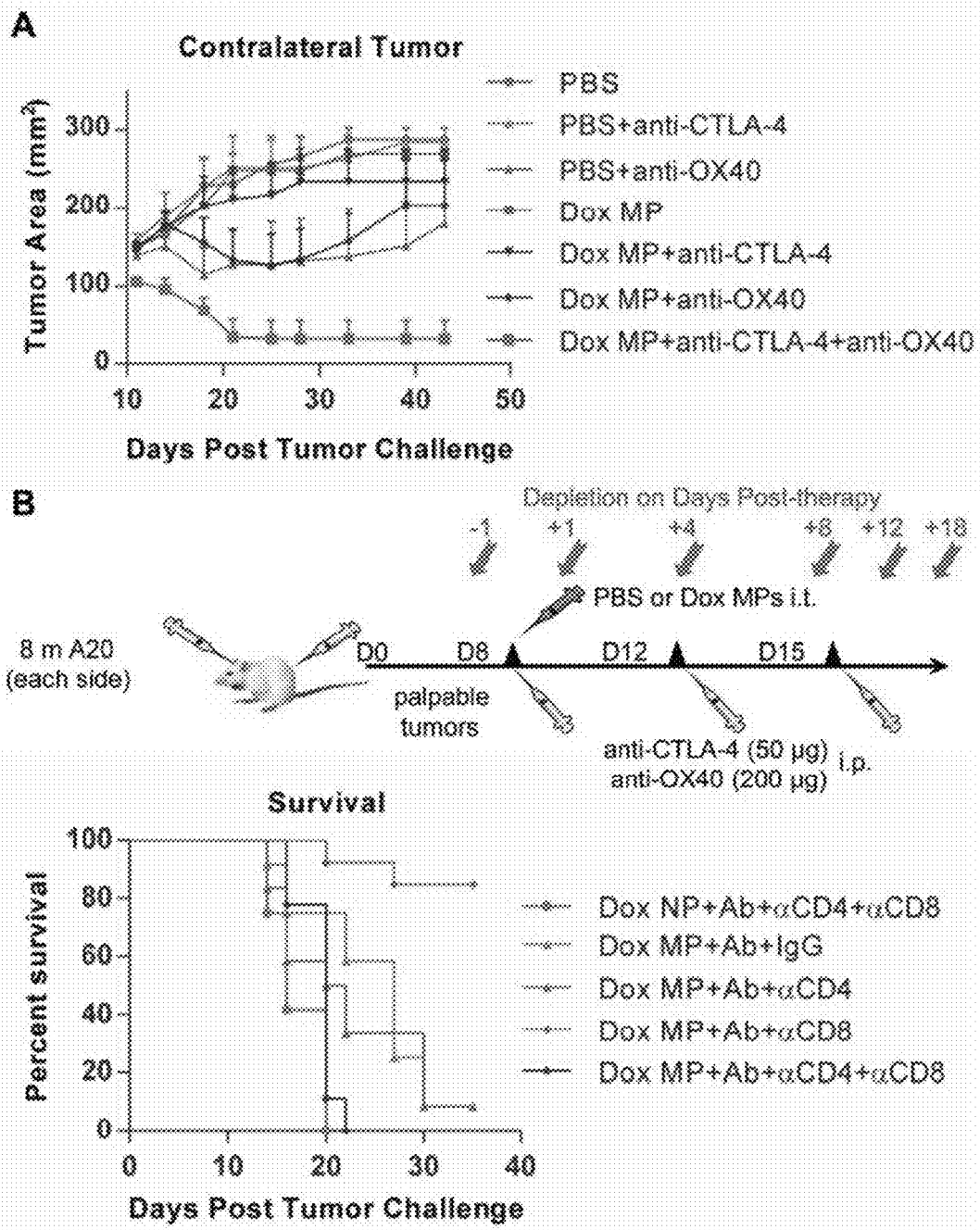
FIG. 12. Three-step therapy induces CD4- and CD8-dependent immune responses and requires all therapy components for maximum efficiency. A. Mice (7-8/group) were treated and observed similarly to that described for FIG. 11 except that different combinations among the three therapy components were used to observe the contribution of each. Tumor areas are mean+SEM. B. Mice (9-13/group) were treated and observed as before. Treatments consisted of PBS as control or Dox MP+Ab. Mice receiving three-step therapy additionally received multiple injections of either anti-CD4, anti-CD8, or both according to the schematic shown.
Figure 18:
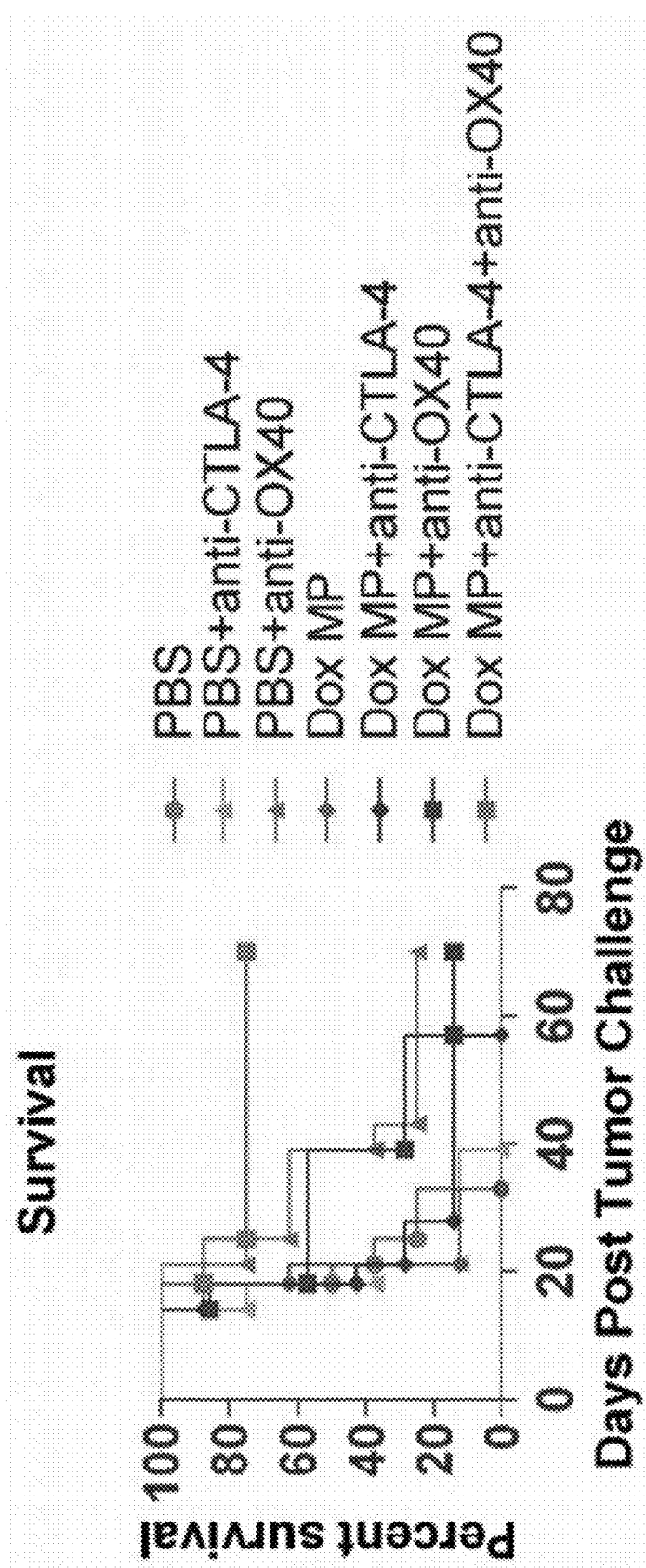
FIG. 18. All therapy components are required for maximum efficacy. Mice (7-8/group) were treated and observed as illustrated in FIG. 12A then monitored for tumor growth and survival. Survival data is shown up to Day 70 post tumor challenge.

We next evaluated the contributions of the various components of therapy. Dox MPs alone were incapable of inducing efficient immune responses, as indicated by unrestrained growth of contralateral tumors (FIG. 12A) and poor survival (FIG. 18). Similarly, anti-CTLA-4 alone or in combination with Dox MPs was insufficient to cure contralateral tumors. While anti-OX40 alone initially delayed tumor growth, tumors progressed with time and survival was not enhanced beyond 30% even when combined with Dox MPs (p>0.05; FIG. 18). In contrast, all three components significantly reduced tumor growth as compared to all other groups (6 out of 8 mice became tumor-free) (FIG. 12A), confirming all components are needed for maximum efficacy.

Figure 19:
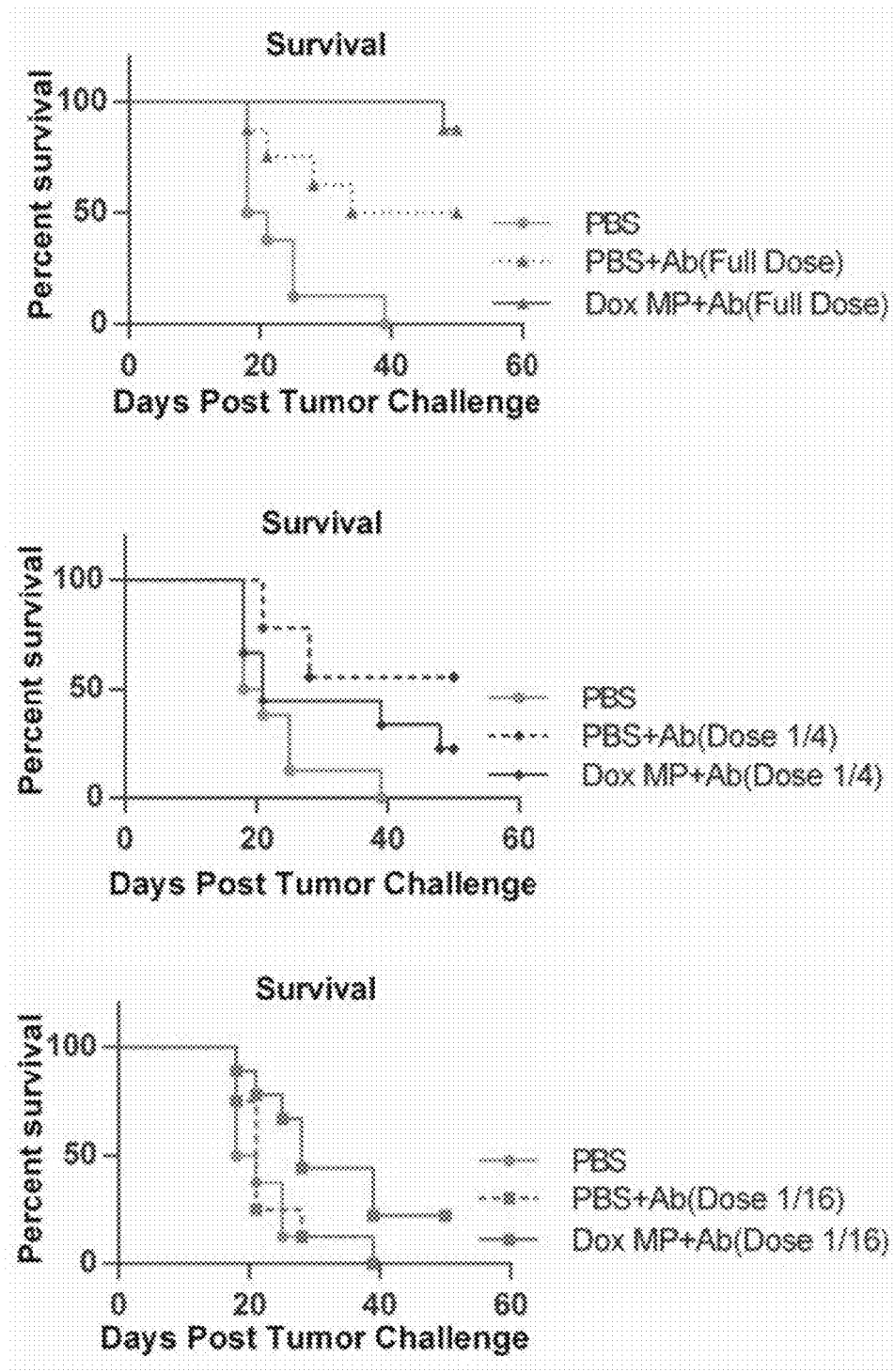
FIG. 19. Ab dose used is optimal. Mice (8-9/group) were treated and observed as before. Treatments consisted of PBS as control, PBS+Ab or Dox MP+Ab at three Ab doses: Full dose (50 μg anti-CTLA-4 and 200 μg anti-OX40), Dose ¼ (12.5 μg anti-CTLA-4 and 50 μg anti-OX40) and Dose 1/16 (3.125 μg anti-CTLA-4 and 12.5 μg anti-OX40).

We further examined the dose of Ab used in three-step therapy (referred to as Full Dose) by comparing it to Ab doses that were $1/4^{th}$ and $1/16^{th}$ the established dose (FIG. 19). Efficacy was reduced with both lower doses, confirming that our established Ab dose (which is 50% of the reported dose (13)) was optimal in this model.

To confirm the role of T-cell subsets in the therapeutic response, CD4 or CD8 T cells were depleted. Depletion of either CD4 or CD8 T cells abolished the therapeutic effect (FIG. 12B), confirming that the systemic antitumor effect was T cell-mediated.

Three-Step Therapy Enhances T-Cell Infiltration into Contralateral Tumors.

Figure 20:
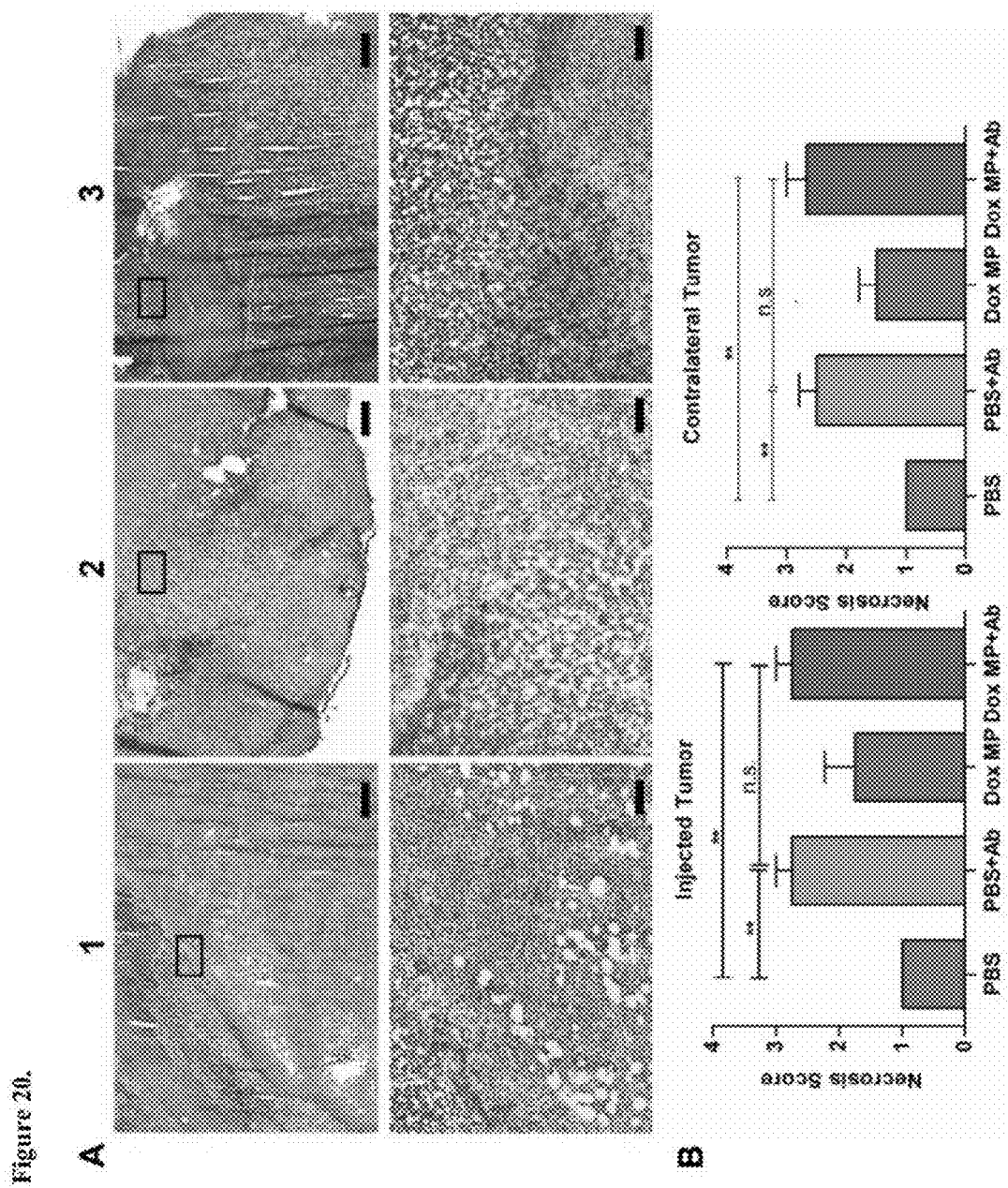
FIG. 20. Three-step therapy and Ab therapy induce comparable tumor necrosis. Mice (4/group) were treated as before. Treatments consisted of PBS as control, PBS+Ab, Dox MP, or Dox MP+Ab. Injected and contralateral tumors were harvested and frozen in OCT on Day 5 post therapy. Frozen samples were sectioned and stained with hematoxylin and eosin. Neoplastic round cells with large nuclei and 1-2 prominent nucleoli, often extending into the underlying muscle were found in all samples.6A. Representative histology images demonstrate necrosis score; 1, <20% of tumor mass is necrotic; 2, 25%-75% of tumor mass is necrotic; 3, >75% of tumor mass is necrotic. Boxed regions are shown as higher magnification images in the lower panel. Bar=100 μm (top panel), 200 μm (bottom panel). Necrosis scores are quantified in 6B.

We next evaluated the tumor microenvironment histologically five days after initiation of therapy (FIG. 20). While all tumors showed necrosis, mice that received Ab therapy had significantly more tumor necrosis than PBS control mice. Dox MP+Ab therapy and Ab therapy alone induced comparable necrosis, suggesting that the necrosis seen was due to antibody therapy rather than Dox MPs.

Figure 13:
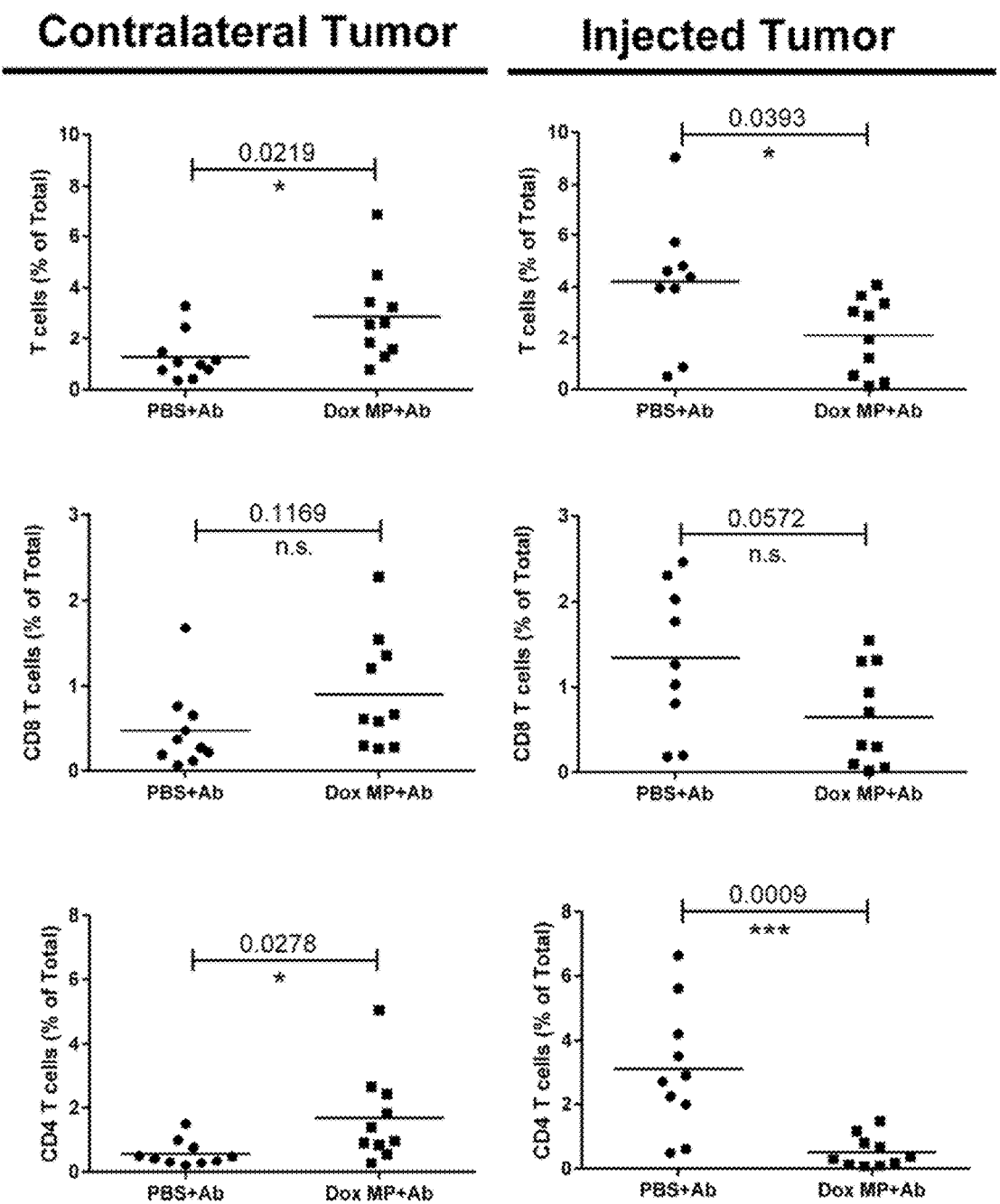
FIG. 13. Three-step therapy enhances T-cell infiltration into contralateral tumors. Mice (5/group) were treated as before. Treatments consisted of PBS+Ab or Dox MP+Ab. On Day 5 post therapy, injected and contralateral tumors were harvested and T-cell infiltrates were analyzed by flow cytometry. Results are presented as percentages of total tumor cells. Data shown are pooled from two independent experiments. *p<0.05; ***p<0.001. n.s. not statistically significant.

While Dox MP+Ab had no detectable effect on necrosis in the contralateral tumor, it did impact on T-cell infiltration (FIG. 13). Mice treated with Dox MP+Ab had an increased percent of T cells infiltrating contralateral tumors. While CD4 T-cell infiltration was significantly enhanced, CD8 T cells showed a trend towards enhancement. These data are in agreement with T-cell depletion data indicating a therapeutic response is T cell-dependent. A lower percentage of T cells was seen in the injected tumors, suggesting that Dox MPs could be cytotoxic to T cells and eliminated them locally. Alternatively, the low percent of T cells in the injected tumor could be due to systemic trafficking.

Figure 21:
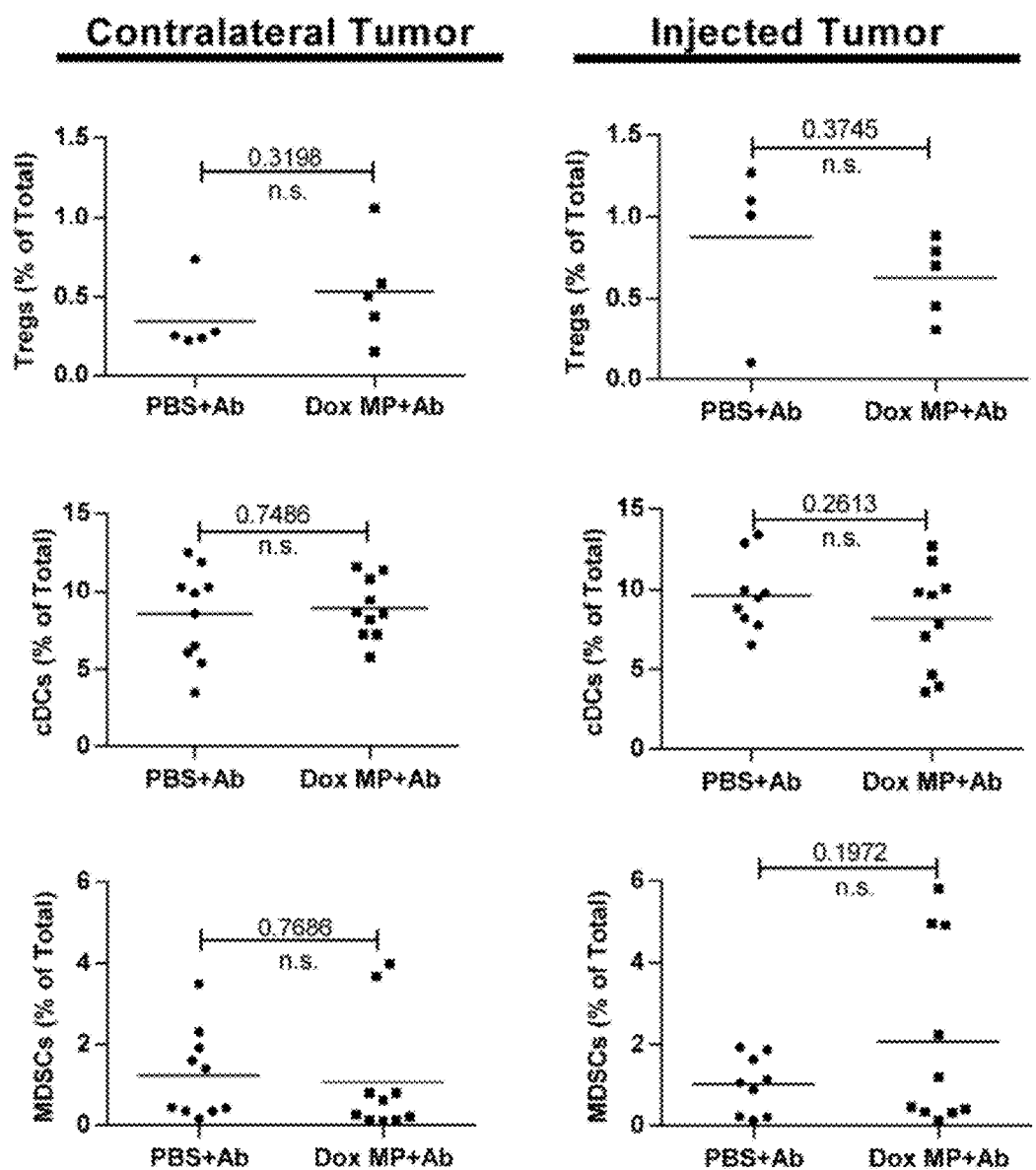
FIG. 21. Three-step therapy induces comparable Treg, cDC and MDSC infiltration into tumors. Mice (5/group) were treated as in FIG. 13. On Day 5 post therapy, injected and contralateral tumors were harvested. Regulatory T cells (Tregs; CD3$^+$CD4$^+$Foxp3$^+$), conventional DCs (cDCs; CD11b$^-$CD11c$^+$) and myeloid-derived suppressor cells (MDSC; CD11c$^-$CD11b$^+$Gr-1$^{hi}$) were analyzed by flow cytometry. Results are presented as percentages of total tumor cells. Data are pooled from 2 independent experiments except for Treg data. n.s. not significant.
Figure 22:
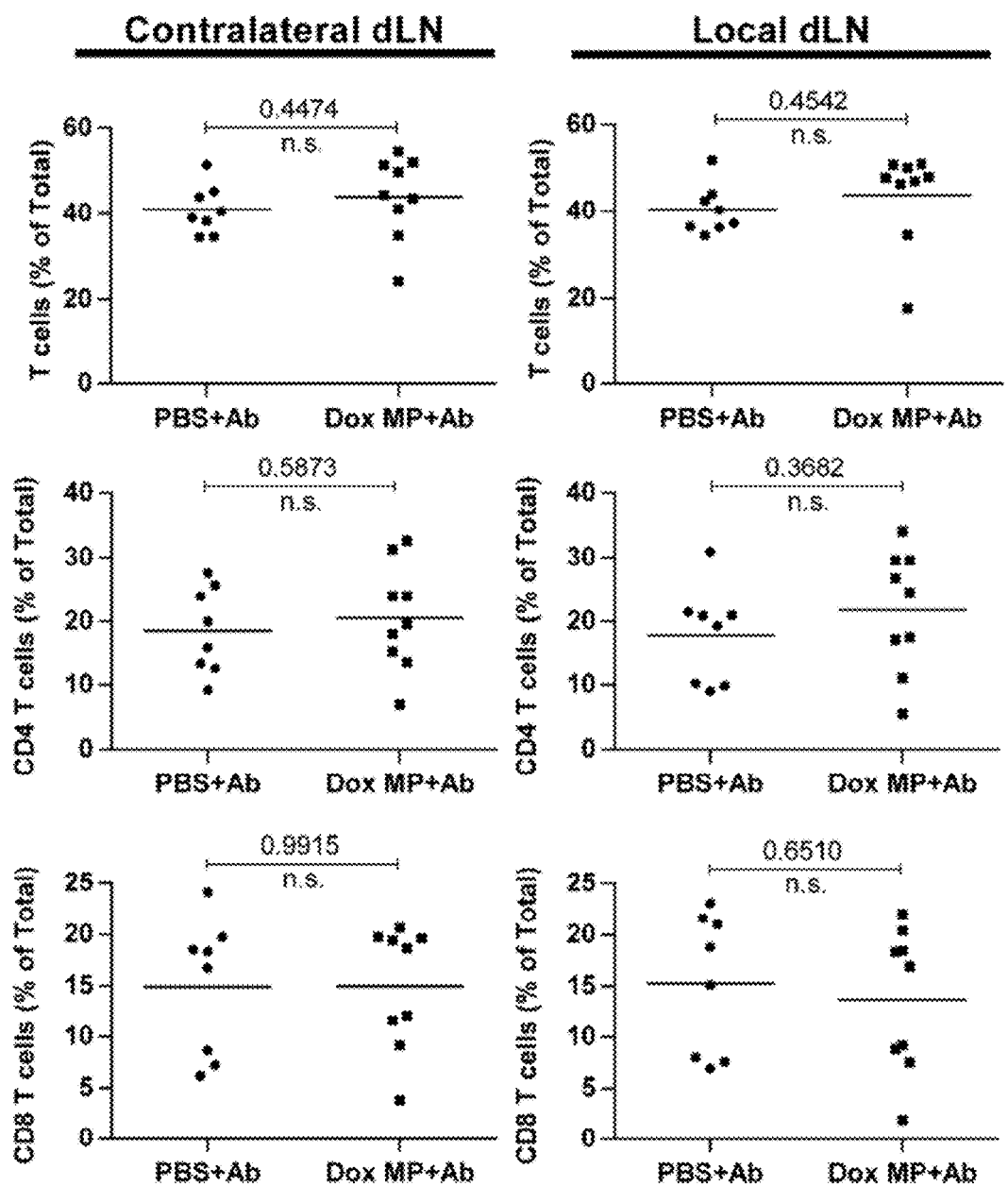
FIG. 22. No differences in T cells were seen in draining lymph nodes. Mice (5/group) were treated as in FIG. 13. On Day 7 post therapy, injected (local) and contralateral draining lymph nodes (dLNs) were harvested and T cell infiltrates were analyzed by flow cytometry. Results are presented as percentages of total lymph node cells. Data shown are pooled from 2 independent experiments. n.s. not significant.
Figure 23:
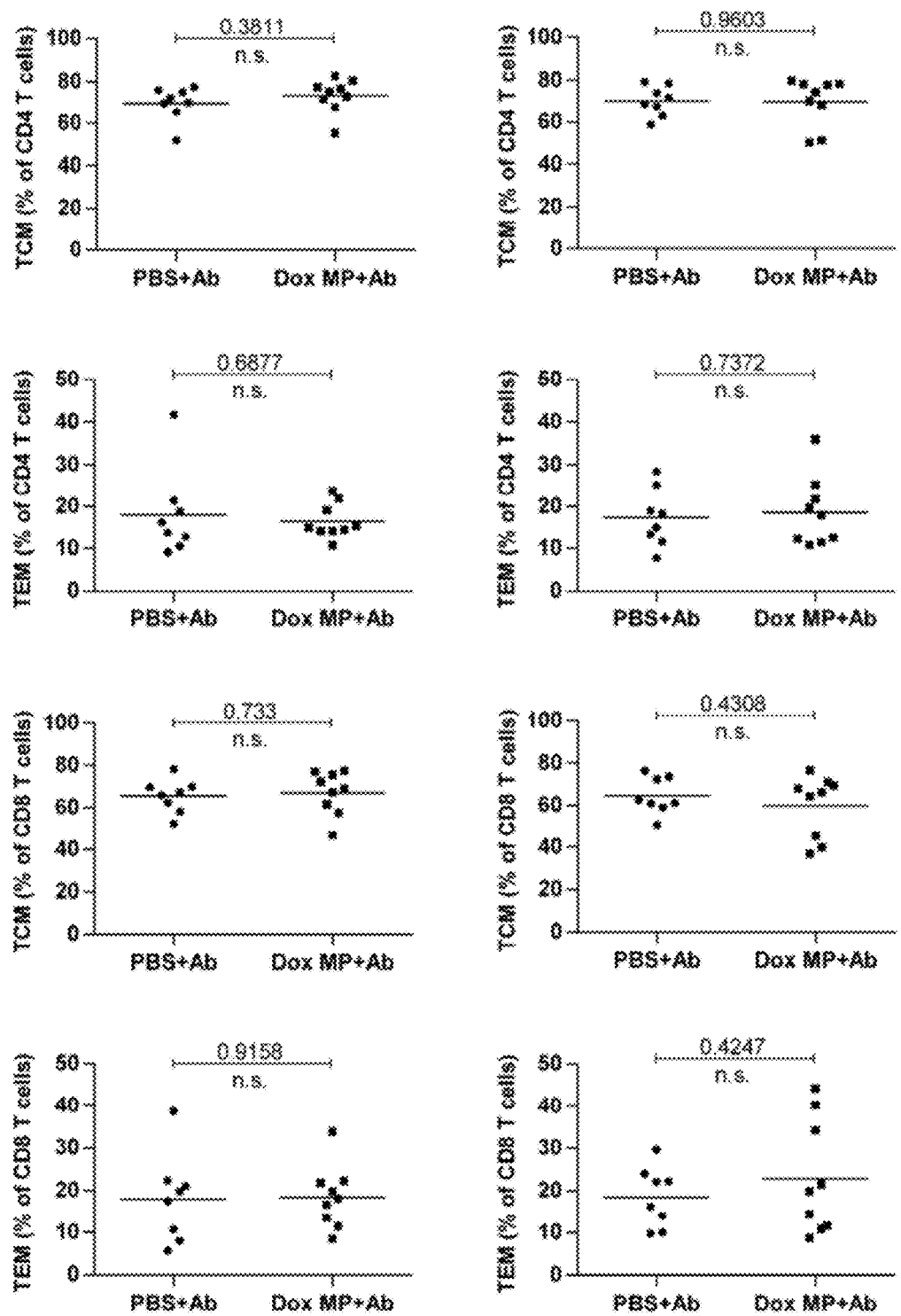
FIG. 23. No differences in T cell activation phenotype were seen in draining lymph nodes. Mice (5/group) were treated as in FIG. 13. On Day 7 post therapy, injected (local) and contralateral draining lymph nodes (dLNs) were harvested and T cell activation phenotype (CD44 and CD62L expression) was analyzed by flow cytometry. Two populations were examined: central memory T cells (TCM; CD44$^+$CD62L$^+$) and effector memory T cells (TEM; CD44$^+$CD62L$^-$). Results are presented as percentages of CD4 or CD8 T cells. Data shown are pooled from two independent experiments. n.s. not significant.

We also examined Tregs, DCs, and myeloid-derived suppressor cells within tumors and found no differences between three-step therapy and Ab therapy (FIG. 21). Evaluation of T cells and their activation phenotype (CD44 and CD62L expression) in draining lymph nodes of both local and contralateral tumors on Day 7 post therapy similarly revealed no significant differences between the two groups (FIGS. 22 and 23).

Figure 8:
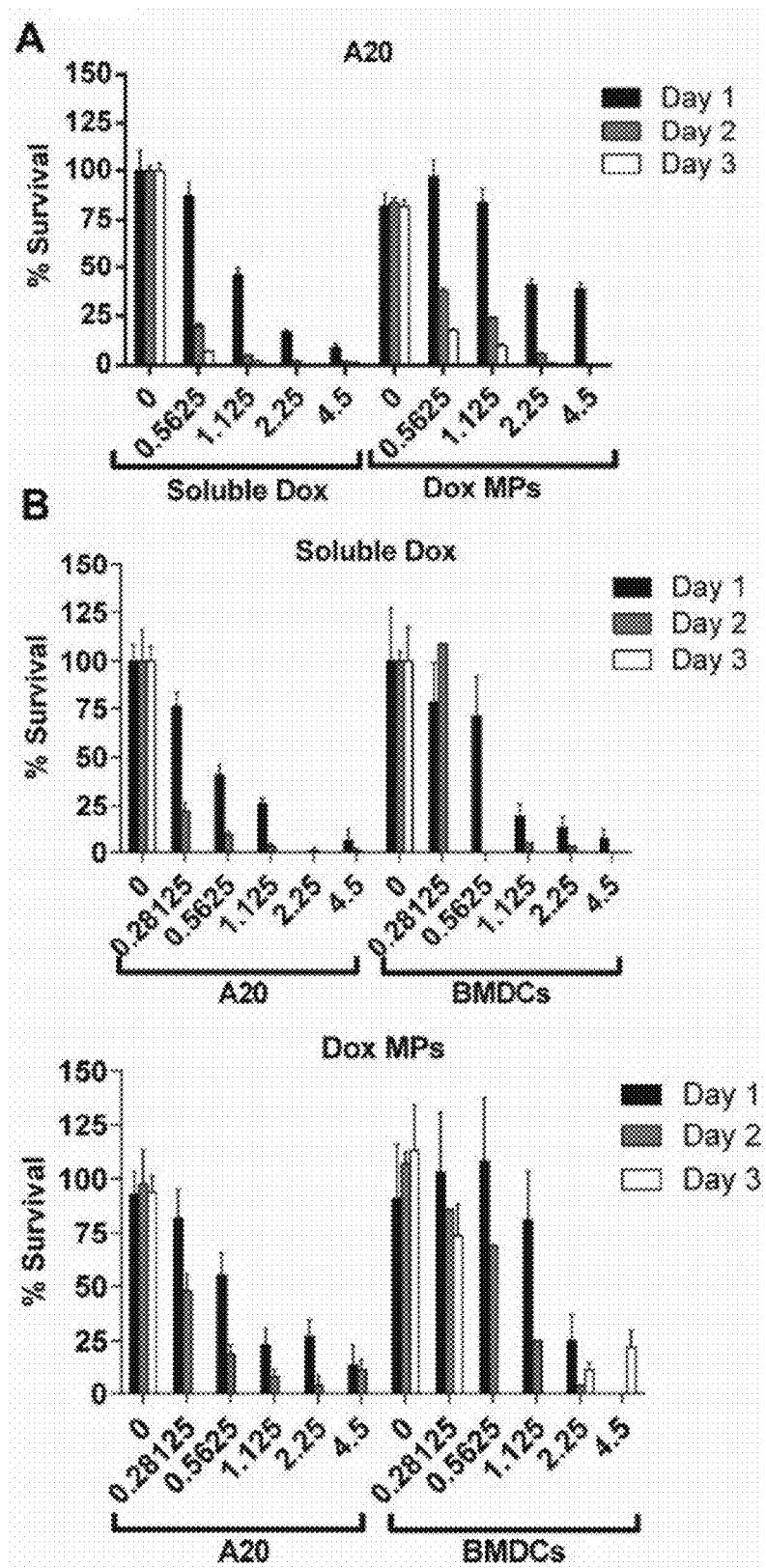
FIG. 8. Dox MPs kill tumor cells more slowly than soluble Dox and are less cytotoxic to DCs. A20 B lymphoma tumor cells (1A and 1B) and DCs (1B) were cultured for 24, 48 and 72 h with increasing concentrations (μg/mL) of soluble Dox or Dox MPs. Media or blank MPs (equivalent weight) were used as controls. Viability was assayed by MTS. Percent survival was expressed as the ratio of absorbance of treated cells relative to that of untreated cells (after subtracting the absorbance of the blank from each) multiplied by 100. Wells with equivalent MP concentrations in absence of cells were used as blanks. Results are mean±SEM (n=4).

As illustrated in FIG. 8, DC viability dropped after 3 days of incubation in vitro with Dox MPs. Many factors, including retention of Dox in the media, could have impacted on this. We therefore evaluated the effect of Dox MPs on DC viability in situ, and found that it was not affected as indicated by the similar percentages of DCs infiltrating Dox MP-injected tumors and contralateral tumors (FIG. 21).

Figure 24:
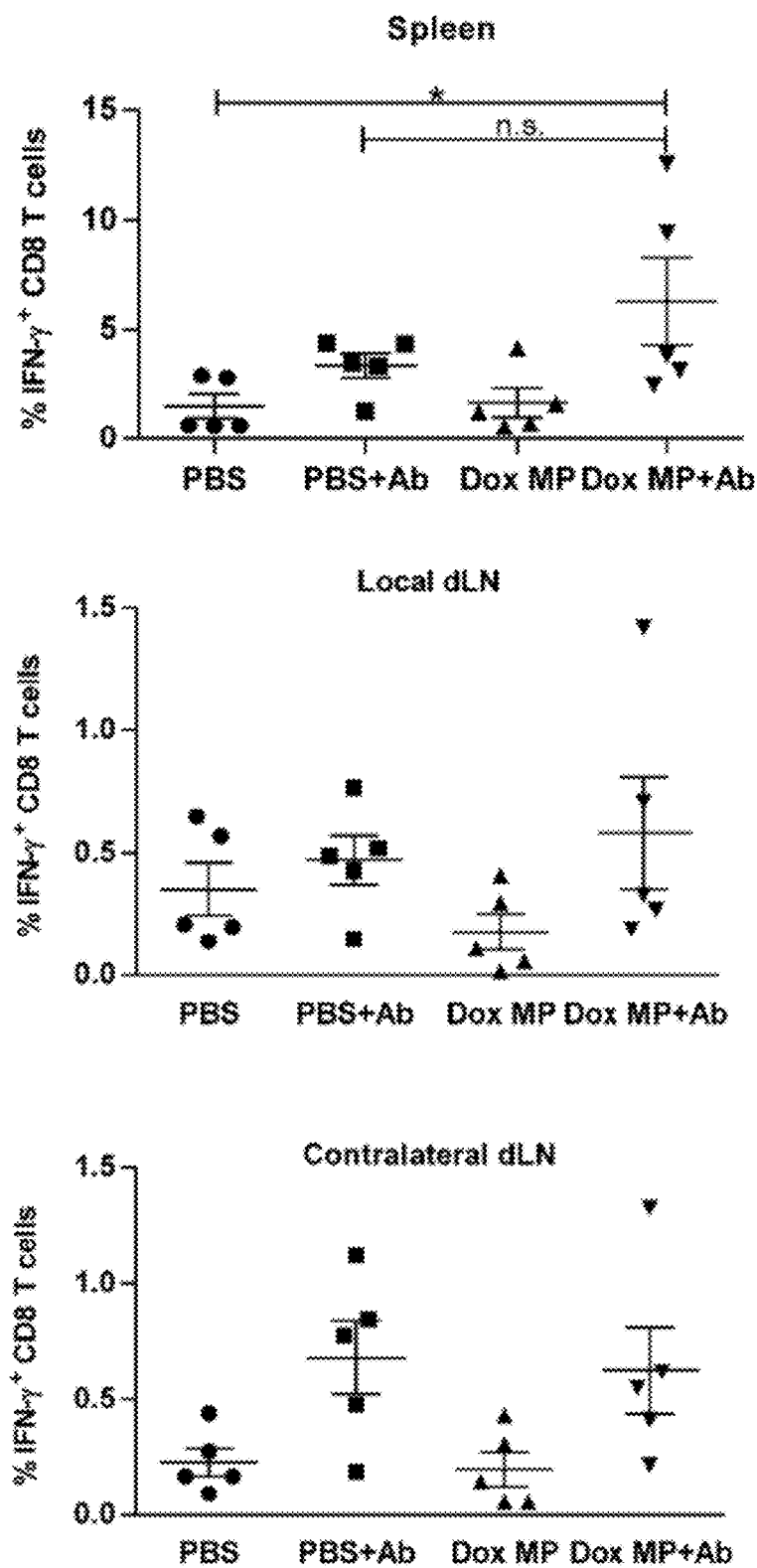
FIG. 24. No differences in antigen-specific responses were seen in lymphoid tissues. Mice (5/group) were inoculated with A20 tumors and treated as detailed. Treatments consisted of PBS, PBS+Ab, Dox MP, or Dox MP+Ab. On Day 7 post therapy, spleens and draining lymph nodes (dLNs) for both injected (local) and contralateral tumors were harvested separately and made into single-cell suspensions. Splenocytes and lymph node cells were cocultured in vitro in the presence of irradiated A20 tumor cells for 24 hours. CD8 T cells were assayed for intracellular IFN-γ expression by flow cytometry. n.s. not significant.

Various approaches to evaluating the cytotoxic T-cell response were assessed, including interferon gamma (IFNγ) assays by ELISpot and flow cytometry, CD107a surface expression, and IL2 production. Evaluation of IFN γ responses by flow cytometry proved most reproducible. Antigen-specific T-cell responses were examined by flow cytometry in the spleens and draining lymph nodes on Day 7 post therapy by incubating cell suspensions overnight with irradiated A20 tumor cells. The percentage of IFNγ-producing CD8 T cells was similar with three-step therapy and Ab therapy (FIG. 24).

Three-Step Therapy is Effective in a Murine EL4 Lymphoma Tumor Model.

Figure 25:
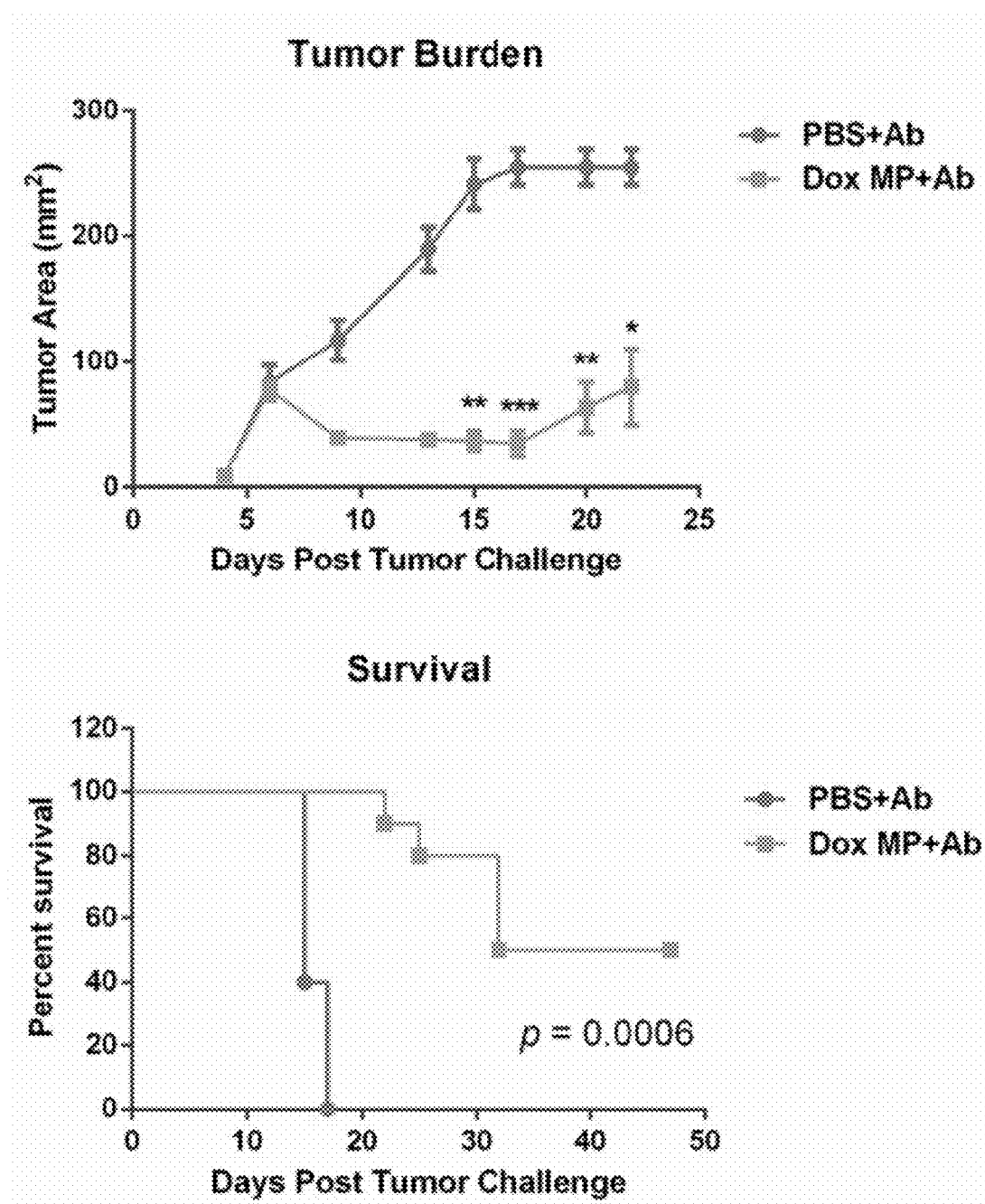
FIG. 25. Three-step therapy is efficient at reducing EL4 tumor burdens. C57BL/6 mice (5-10 mice/group) were subcutaneously inoculated with EL4 at a dose of one million cells in the right flank. On Day 4 post-inoculation, Dox MPs (2 μg Dox) were injected into the tumor site. PBS was given to control groups. Anti-CTLA4 (50 μg) and anti-OX40 (200 μg) (collectively referred to as Ab) were administered by intraperitoneal injections of three doses given every 3-4 days, starting from Day 1 of treatment. Mice were monitored for tumor growth and survival. Tumor areas are mean±SEM. *p<0.05; p<0.01; *p<0.001.

The ability of Dox MPs to enhance the effect of Ab therapy was also evaluated in the EL4 T-cell lymphoma model. Our prior studies demonstrated MPs containing higher doses of Dox are needed to effectively treat EL4, and that EL4 grows too rapidly for a two-sided model to be valuable (26). We therefore evaluated the effect of three-step therapy on EL4 by treating a single tumor with Dox MPs at a dose of 25 µg Dox. Using this approach, Dox MP+Ab significantly reduced EL4 tumor burdens and resulted in 50% long-term survival. None of the mice receiving Ab therapy alone survived (FIG. 25).

Discussion

With the growth of scientific insight into pathways that regulate the immune system and cancer, we can now more intelligently design and combine immunotherapies that work in different ways to overcome deficiencies of single therapies (27). One attractive approach is to use in situ therapy with MPs to manipulate the tumor microenvironment in a manner that breaks tolerance and allows development of a robust immune response. The number of variables that needs to be evaluated when trying to optimize the promise of such a multistep approach is considerable. Here, we address many of these variables, and demonstrate this approach has promising immunologic and therapeutic effects.

An ideal in situ immunization approach would deliver localized and effective drug concentrations into the tumor with low systemic toxicity (23). Given its long history of FDA-approved use for biomedical applications and its biocompatibility (28), PLGA was seen as an excellent candidate polymeric vehicle for controlled release of Dox from MPs into the tumor.

We first optimized formulation parameters affecting particle size, loading, and release. 1-μm PLGA MPs have been shown to be more effective than 200 nm, 500 nm, and 5-μm particles as vaccine adjuvants (29). The relatively low dose of Dox MPs, coupled with their sustained release, proved to be a safe combination for DCs that survived well in vitro and in situ despite internalizing the particles.

A20 tumor cells were killed more slowly by Dox MPs than by soluble Dox, as previously seen with chemotherapy-loaded PLGA particles (23). However, Dox MPs resulted in more efficient phagocytosis. Dox MPs and soluble Dox were compared based on equivalent total amounts of Dox. However, at any given time point and at equivalent "doses", the amount of Dox released by Dox MPs was likely lower than that of soluble Dox. As such, one explanation for why Dox MPs were superior to soluble Dox is that the exposure of malignant cells to a lower Dox concentration enhanced the expression of calreticulin as compared to the bolus dose of soluble Dox (30). Because of technical difficulties associated with Dox MPs adhering to tumor cells, we were unable to demonstrate that Dox MPs calreticulin expression by tumor cells. Shurin and colleagues have shown that ultra-low concentrations of Dox regulate the activity of small Rho GTPases that control the endocytic activity of DCs (31). Thus, it is also possible that Dox MPs adherent to Dox MP-treated A20 cells may be contributing to the enhanced phagocytosis by exposing DCs to very low concentrations of Dox.

Three-step therapy was superior to Ab therapy in inducing curative immune responses. The depletion of CD4 and CD8 T cells abrogated the therapeutic immune response, indicating that it was T cell-mediated. Several studies have confirmed the role of CD8 T cells in Dox-mediated antitumor immune responses (32, 33) and of both CD4 and CD8 T cells in anti-CTLA-4- and anti-OX40-mediated immune responses (13, 34, 35). Thus, the finding that both CD4 and CD8 cells are needed for an optimal antitumor effect in our studies was not surprising.

To investigate how the addition of Dox MPs to Ab therapy is modulating the intratumoral T-cell response, we examined the Treg population and found no effect of three-step therapy on the percent of Tregs. On the other hand, we found enhanced CD4 T-cell infiltration in contralateral but not injected tumors. These results suggest changes induced by therapy enhanced the ability of CD4 T cells to contribute to the immune response and overcome effects of Tregs.

The combination of Dox MPs, anti-CTLA-4 and anti-OX40 was required for the most efficient immune response. Given that Dox MPs alone were incapable of generating immune responses and the combination of anti-CTLA-4 and anti-OX40 without Dox MPs was not as efficient at reducing tumor burden as three-step therapy, it is likely that anti-OX40 is amplifying the primed T-cell response generated with Dox MPs and that anti-CTLA4 is allowing for that response to be maintained. This contention is supported by enhanced T-cell infiltration in tumors following the three components as compared to Ab therapy.

The increase in pathologically-detectable destruction of established tumors, as reflected by tumor necrosis, was seen with both the three-step therapy and Ab therapy. Quantifying necrosis within a tumor sample is difficult, and it was not possible to determine definitively whether three-step therapy enhanced necrosis, however the improved overall outcome suggests this is the case. Similar responses were seen in tumor samples from patients receiving immunotherapy, and may thus be reflective of the ongoing antitumor immune response (36).

We also validated the efficiency of three-step therapy in the EL4 tumor model. There are clear differences between mouse models of malignancy such as A20 or EL4 and human tumors. An example is potential retroviral contamination of cell lines that could serve as target antigens. Irrespective of the target antigen or immunogenicity of the model, our studies demonstrate that in situ treatment with Dox MPs can enhance the immunotherapy effects of immunostimulatory and checkpoint blockade Abs. Further studies will be needed to assess the efficacy of our design in other tumor models in mice, and eventually in clinical trials.

The three-step design is complex, and the number of agents that could be evaluated for each step is extensive. Other approaches, such as local radiation, can be used to induce local immunogenic cell death (37). Anti-OX40 can be substituted with other immunostimulatory antibodies targeting TNFR co-stimulatory molecules, including CD40 and CD137 or TLR agonists such as CpG (37). Anti-CTLA-4 can be substituted with other antibodies that mediate checkpoint blockade such as anti-PD-1 (38). Alternatives related to the dosing and timing of how these agents could be used together leads to an almost endless number of possible combinations. The studies reported here highlight the value of the three-step approach rather than demonstrate that the specific agents or regimen used is superior to other regimens.

Indeed, given that Dox MPs are not clinically approved, a faster translation to the clinic could require approximation of our design using readily-available reagents such as liposomal Dox (Doxil®)). In preliminary studies, we found Dox MPs were more effective than liposomal Dox in inducing systemic immune responses in mice (data not shown) which is why they were used. PLGA particles were shown to be superior to liposomal formulations in inducing cellular immune responses, which was attributed to their sustained release rather than an adjuvant effect of the synthesizing material (39). Indeed, liposomal Dox is currently under consideration for a clinical trial exploring a combination similar to that outlined in this report. While liposomal Dox would provide a more direct path toward clinical evaluation, studies comparing Dox MPs to liposomal Dox in human cell lines would also be informative.

Figure 14:
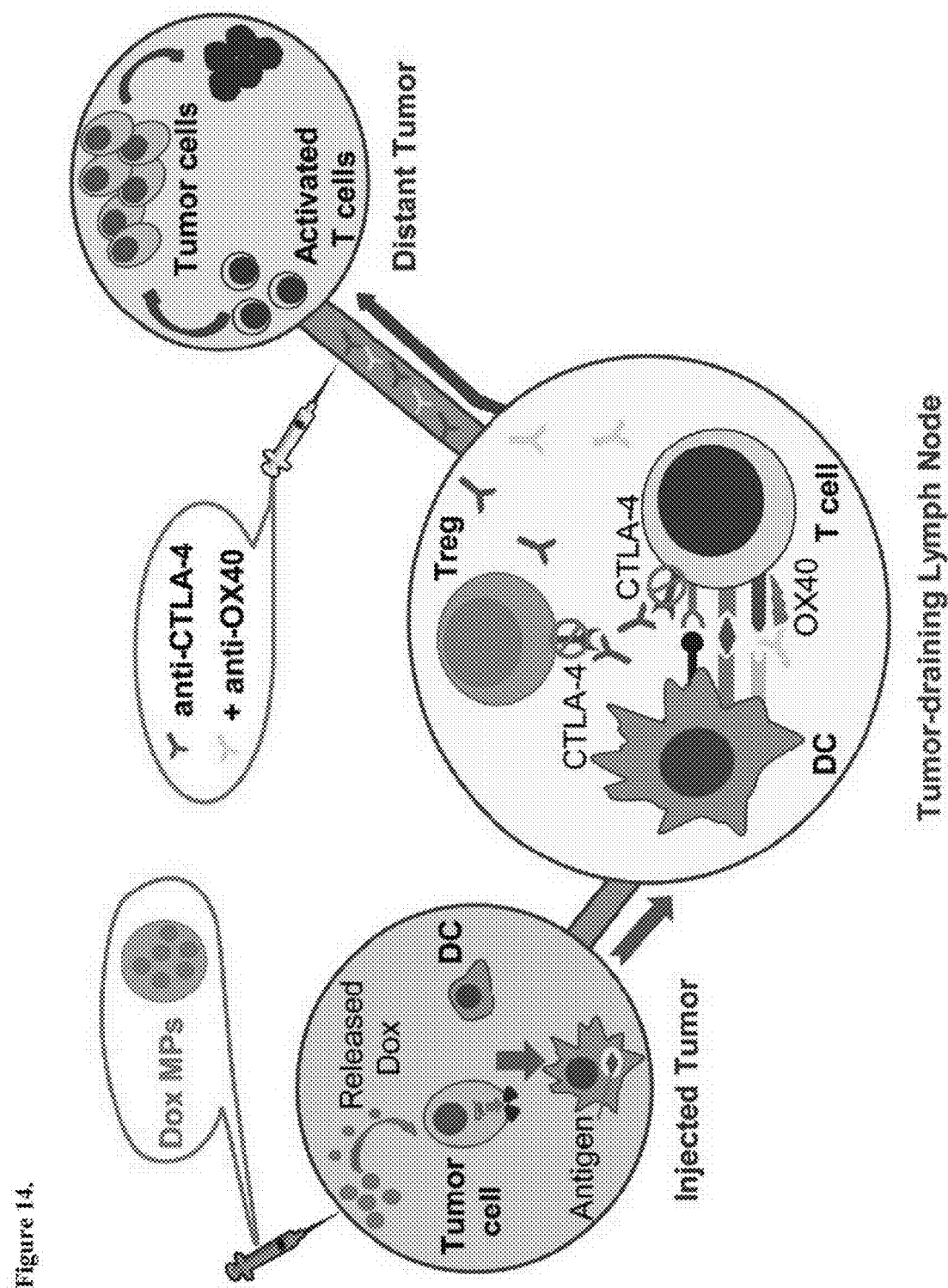
FIG. 14. systemic immune response is generated through local tumor manipulation—a proposed schematic. Dox MPs injected intratumorally upregulate surface calreticulin expression on dying tumor cells, enhancing their phagocytosis by DCs which migrate to draining lymph nodes and present tumor antigen to antigen-specific T cells. Anti-OX40 enhances T-cell activation while anti-CTLA-4 blocks immunosuppression imposed by CTLA-4, thus allowing tumor-specific T cells to proceed unrestrained to distant tumor sites.

In conclusion, recent advances in our understanding of cancer immunotherapy suggest rational combined approaches will be keys to enhancing efficacy. We evaluated a three-step approach to in situ immunization using biodegradable Dox MPs, anti-CTLA-4 and anti-OX40 (FIG. 14). Further preclinical evaluation of this promising therapeutic strategy in other types of cancer is ongoing, as are plans to translate these findings to the clinics.

REFERENCES

1. Topalian S L, Weiner G J, Pardoll D M. Cancer immunotherapy comes of age. *J Clin Oncol.* 2011; 29(36):4828-4836.
2. Mellman I, Coukos G, Dranoff G. Cancer immunotherapy comes of age. *Nature.* 2011; 480(7378):480-489.
3. Crittenden M R, Thanarajasingam U, Vile R G, Gough M J. Intratumoral immunotherapy: Using the tumour against itself. *Immunology.* 2005; 114(1):11-22.
4. Visani G, Isidori A. Doxorubicin variants for hematological malignancies. *Nanomedicine (Lond).* 2011; 6(2):303-306.
5. Vacchelli E, Galluzzi L, Fridman W H, et al. Trial watch: Chemotherapy with immunogenic cell death inducers. *Oncoimmunology.* 2012; 1(2):179-188.
6. Locher C, Conforti R, Aymeric L, et al. Desirable cell death during anticancer chemotherapy. *Ann N Y Acad Sci.* 2010; 1209:99-108.
7. Obeid M, Tesniere A, Ghiringhelli F, et al. Calreticulin exposure dictates the immunogenicity of cancer cell death. *Nat Med.* 2007; 13(1):54-61.
8. Aguilar L K, Guzik B W, Aguilar-Cordova E. Cytotoxic immunotherapy strategies for cancer: Mechanisms and clinical development. *J Cell Biochem.* 2011; 112(8):1969-1977.
9. Hollander N. Immunotherapy for B-cell lymphoma: Current status and prospective advances. *Front Immunol.* 2012; 3:3.
10. Wolchok J D, Yang A S, Weber J S. Immune regulatory antibodies: are they the next advance? *Cancer J.* 2010; 16(4):311-317.
11. Grosso J F, Jure-Kunkel M N. CTLA-4 blockade in tumor models: An overview of preclinical and translational research. *Cancer Immun.* 2013; 13:5.
12. Pardoll D M. The blockade of immune checkpoints in cancer immunotherapy. *Nat Rev Cancer.* 2012; 12(4):252-264.
13. Houot R, Levy R. T-cell modulation combined with intratumoral CpG cures lymphoma in a mouse model without the need for chemotherapy. *Blood.* 2009; 113(15):3546-3552.
14. Conde-Estevez D, Mateu-de Antonio J. Treatment of anthracycline extravasations using dexrazoxane. *Clin Transl Oncol.* 2014; 16(1):11-17.
15. Waeckerle-Men Y, Groettrup M. PLGA microspheres for improved antigen delivery to dendritic cells as cellular vaccines. *Adv Drug Deliv Rev.* 2005; 57(3):475-482.
16. Sharp F A, Ruane D, Claass B, et al. Uptake of particulate vaccine adjuvants by dendritic cells activates the NALP3 inflammasome. *Proc Natl Acad Sci USA.* 2009; 106(3):870-875.
17. Benichou A, Garti N. Double emulsions for controlled-release applications-progress and trends. In: CRC Press; 2001:409-442. http://dx.doi.org.proxy.lib.uiowa.edu/10.1201/9781420029581.ch17. doi:10.1201/9781420029581.ch17.
18. Chakravarthi S S, De S, Miller D W, Robinson D H. Comparison of anti-tumor efficacy of paclitaxel delivered in nano- and microparticles. *Int J Pharm.* 2010; 383(1-2):37-44.
19. Yoo H S, Lee K H, Oh J E, Park T G. In vitro and in vivo anti-tumor activities of nanoparticles based on doxorubicin-PLGA conjugates. *J Control Release.* 2000; 68(3):419-431.
20. Hempel G, Flege S, Wurthwein G, Boos J. Peak plasma concentrations of doxorubicin in children with acute lymphoblastic leukemia or non-hodgkin lymphoma. *Cancer Chemother Pharmacol.* 2002; 49(2):133-141.
21. AACR Cancer Progress Report Writing Committee, Sawyers C L, Abate-Shen C, et al. AACR cancer progress report 2013. *Clin Cancer Res.* 2013; 19(20 Suppl):54-98.
22. Belcaid Z, Phallen J A, Zeng J, et al. Focal radiation therapy combined with 4-1BB activation and CTLA-4 blockade yields long-term survival and a protective antigen-specific memory response in a murine glioma model. *PLoS One.* 2014; 9(7):e101764.
23. Yoo H S, Lee K H, Oh J E, Park T G. In vitro and in vivo anti-tumor activities of nanoparticles based on doxorubicin-PLGA conjugates. *J Control Release.* 2000; 68(3):419-431.
24. Silva J M, Videira M, Gaspar R, Preat V, Florindo H F. Immune system targeting by biodegradable nanoparticles for cancer vaccines. *J Control Release.* 2013; 168(2):179-199.
25. Oyewumi M O, Kumar A, Cui Z. Nano-microparticles as immune adjuvants: Correlating particle sizes and the resultant immune responses. *Expert Rev Vaccines.* 2010; 9(9):1095-1107.
26. Farazuddin M, Dua B, Zia Q, Khan A A, Joshi B, Owais M. Chemotherapeutic potential of curcumin-bearing microcells against hepatocellular carcinoma in model animals. *Int J Nanomedicine.* 2014; 9:1139-1152.
27. Sheng Sow H, Mattarollo S R. Combining low-dose or metronomic chemotherapy with anticancer vaccines: A therapeutic opportunity for lymphomas. *Oncoimmunology.* 2013; 2(12):e27058.
28. Sheng Sow H, Mattarollo S R. Combining low-dose or metronomic chemotherapy with anticancer vaccines: A therapeutic opportunity for lymphomas. *Oncoimmunology.* 2013; 2(12):e27058.
29. Shurin G V, Tourkova I L, Shurin M R. Low-dose chemotherapeutic agents regulate small rho GTPase activity in dendritic cells. *J Immunother.* 2008; 31(5):491-499.
30. Casares N, Pequignot M O, Tesniere A, et al. Caspase-dependent immunogenicity of doxorubicin-induced tumor cell death. *J Exp Med.* 2005; 202(12):1691-1701.
31. Ghiringhelli F, Apetoh L, Tesniere A, et al. Activation of the NLRP3 inflammasome in dendritic cells induces IL-1beta-dependent adaptive immunity against tumors. *Nat Med.* 2009; 15(10):1170-1178.
32. Timar J, Ladanyi A, Forster-Horvath C, et al. Neoadjuvant immunotherapy of oral squamous cell carcinoma modulates intratumoral CD4/CD8 ratio and tumor microenvironment: A multicenter phase II clinical trial. *J Clin Oncol.* 2005; 23(15):3421-3432.
33. Jahrsdorfer B, Blackwell S E, Wooldridge J E, et al. B-chronic lymphocytic leukemia cells and other B cells can produce granzyme B and gain cytotoxic potential after interleukin-21-based activation. *Blood.* 2006; 108 (8):2712-2719.
34. Tosato G, Cohen J I. Generation of epstein-barr virus (EBV)-immortalized B cell lines. *Curr Protoc Immunol.* 2007; Chapter 7:Unit 7.22.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a tumor in a subject in need thereof, the method comprising injecting the tumor in situ with cytotoxic particles, the cytotoxic particles comprising a biodegradable polymer and a cytotoxic agent which is a member of the anthracycline family of DNA-intercalating agents that induces immunogenic tumor cell death and the particles having an average effective diameter of 0.5-10 microns, the method further comprising administering to the subject an immune checkpoint inhibitor after the tumor is injected with the cytotoxic particles, and the method further comprising administering to the subject a T-cell stimulatory agent after the tumor is injected with the cytotoxic particles.

2. The method of claim 1, wherein the cytotoxic agent is selected from a group consisting of Daunorubicin Hydrochloride, Doxorubicin Hydrochloride, Epirubicin Hydrochloride, and Idarubicin Hydrochloride.

3. The method of claim 1, wherein the immune checkpoint inhibitor is selected from the group consisting of an anti CTLA-4 antibody, an anti PD-1 antibody, an anti PD-L1 antibody, an anti IDO-1 antibody, and anti IDO-2 antibody, an anti KIR antibody, an anti CD70 antibody, an anti LAG-3 antibody, an anti B7-H3 antibody, an anti B7-H4 antibody, an anti TIM3 antibody, and combinations thereof.

4. The method of claim 1, wherein the T-cell stimulatory agent targets a TNFR costimulatory molecule and is selected from a group consisting of an anti OX40 agonist antibody, an anti CD40 agonist antibody, and an anti CD137 agonist antibody.

5. The method of claim 1, wherein the T-cell stimulatory agent is a TLR agonist and is selected from the group consisting of unmethylated CpG dinucleotide (CpG-ODN), polyribosinic:polyribocytidic acid (Poly I:C), polyadenosine-polyruridylilc acid (poly AU), polyinosinic-polycytidylic acid stabilized with poly-L-lysine and carboxymethylcellulose (Poly-ICLC), bacterial lipopolysaccharides, MUC1 mucin, and imidazoquinolines.

6. The method of claim 1, wherein the biodegradable polymer of the cytotoxic particles comprises carbohydrate monomers.

7. The method of claim 6, wherein the carbohydrate monomers comprise lactic acid, glycolic acid, or a mixture thereof.

8. The method of claim 1, wherein the cytotoxic particles are formulated as a suspension.

9. The method of claim 1, wherein the method stimulates an immune response against the tumor.

10. The method of claim 9, wherein the immune response is a T-cell response.

11. The method of claim 1, wherein the tumor is selected from the group consisting of adenocarcinoma, lymphoma, melanoma, sarcoma, teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

12. The method of claim 1, wherein the cytotoxic agent is Doxorubicin or Doxorubicin Hydrochloride.

13. A method for treating a tumor in a subject in need thereof, the method comprising injecting the tumor in situ with cytotoxic particles, the cytotoxic particles comprising (i) a biodegradable polymer, (ii) a cytotoxic agent which is a member of the anthracycline family of DNA-intercalating agents that induces immunogenic tumor cell death, and (iii) a T-cell stimulatory agent, and the particles having an average effective diameter of 0.5-10 microns, the method further comprising administering to the subject an immune checkpoint inhibitor after the tumor is injected with the cytotoxic particles.

14. The method of claim 13, wherein the immune checkpoint inhibitor is selected from the group consisting of an anti CTLA-4 antibody, an anti PD-1 antibody, an anti PD-L1 antibody, an anti IDO-1 antibody, and anti IDO-2 antibody, an anti KIR antibody, an anti CD70 antibody, an anti LAG-3 antibody, an anti B7-H3 antibody, an anti B7-H4 antibody, an anti TIM3 antibody, and combinations thereof.

15. The method of claim 13, wherein the T-cell stimulatory agent is a TLR agonist and is selected from the group consisting of unmethylated CpG dinucleotide (CpG-ODN), polyribosinic:polyribocytidic acid (Poly I:C), polyadenosine-polyruridylilc acid (poly AU), polyinosinic-polycytidylic acid stabilized with poly-L-lysine and carboxymethylcellulose (Poly-ICLC), bacterial lipopolysaccharides, MUC1 mucin, and imidazoquinolines.

16. The method of claim 13, wherein the tumor is selected from the group consisting of adenocarcinoma, lymphoma, melanoma, sarcoma, teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

17. A method for treating a lymphoma tumor in a subject in need thereof, the method comprising injecting the lymphoma tumor in situ with cytotoxic particles, the cytotoxic particles comprising a biodegradable polymer and Doxorubicin or Doxorubicin Hydrochloride and the particles having an average effective diameter of 0.5-10 microns, the method further comprising administering to the subject an immune checkpoint inhibitor after the tumor is injected with the cytotoxic particles, and the method further comprising administering to the subject a T-cell stimulatory agent after the tumor is injected with the cytotoxic particles.

18. The method of claim 17, wherein the immune checkpoint inhibitor is selected from the group consisting of an anti CTLA-4 antibody, an anti PD-1 antibody, an anti PD-L1 antibody, an anti IDO-1 antibody, and anti IDO-2 antibody, an anti KIR antibody, an anti CD70 antibody, an anti LAG-3 antibody, an anti B7-H3 antibody, an anti B7-H4 antibody, an anti TIM3 antibody, and combinations thereof.

19. The method of claim 17, wherein the T-cell stimulatory agent targets a TNFR costimulatory molecule and is selected from a group consisting of an anti OX40 agonist antibody, an anti CD40 agonist antibody, and an anti CD137 agonist antibody.

20. The method of claim 17, wherein the T-cell stimulatory agent is a TLR agonist and is selected from the group consisting of unmethylated CpG dinucleotide (CpG-ODN), polyribosinic:polyribocytidic acid (Poly I:C), polyadenosine-polyruridylilc acid (poly AU), polyinosinic-polycytidylic acid stabilized with poly-L-lysine and carboxymethylcellulose (Poly-ICLC), bacterial lipopolysaccharides, MUC1 mucin, and imidazoquinolines.

* * * * *